US010308629B2

(12) United States Patent
Graham et al.

(10) Patent No.: US 10,308,629 B2
(45) Date of Patent: Jun. 4, 2019

(54) 1H-PYRROL-3-AMINES

(71) Applicant: BAYER PHARMA AKTIENGESELLSCHAFT, Berlin (DE)

(72) Inventors: Keith Graham, Berlin (DE); Ulrich Klar, Berlin (DE); Hans Briem, Berlin (DE); Gerhard Siemeister, Berlin (DE); Ursula Mönning, Woltersdorf (DE)

(73) Assignee: BAYER PHARMA AKTIENGESELLSCHAFT, Berlin (DE)

( * ) Notice: Subject to any disclaimer, the term of this patent is extended or adjusted under 35 U.S.C. 154(b) by 0 days.

(21) Appl. No.: 15/750,103

(22) PCT Filed: Aug. 1, 2016

(86) PCT No.: PCT/EP2016/068279
§ 371 (c)(1),
(2) Date: Feb. 2, 2018

(87) PCT Pub. No.: WO2017/021348
PCT Pub. Date: Feb. 9, 2017

(65) Prior Publication Data

US 2018/0222881 A1 Aug. 9, 2018

(30) Foreign Application Priority Data

Aug. 5, 2015 (EP) .................................... 15179859
Dec. 16, 2015 (EP) .................................... 15200620

(51) Int. Cl.

| | |
|---|---|
| ***A61K 31/403*** | (2006.01) |
| ***A61K 31/407*** | (2006.01) |
| ***A61K 31/4439*** | (2006.01) |
| ***A61P 35/00*** | (2006.01) |
| ***C07D 401/04*** | (2006.01) |
| ***C07D 401/14*** | (2006.01) |
| ***C07D 487/14*** | (2006.01) |
| ***C07D 405/14*** | (2006.01) |
| ***C07D 403/04*** | (2006.01) |
| ***C07D 409/14*** | (2006.01) |
| ***C07D 417/14*** | (2006.01) |
| ***C07D 471/04*** | (2006.01) |
| ***C07D 491/056*** | (2006.01) |
| ***C07D 487/04*** | (2006.01) |
| ***A61K 45/06*** | (2006.01) |

(52) U.S. Cl.
CPC ........ *C07D 401/04* (2013.01); *A61K 31/4439* (2013.01); *A61K 45/06* (2013.01); *C07D 401/14* (2013.01); *C07D 403/04* (2013.01); *C07D 405/14* (2013.01); *C07D 409/14* (2013.01); *C07D 417/14* (2013.01); *C07D 471/04* (2013.01); *C07D 487/04* (2013.01); *C07D 491/056* (2013.01)

(58) Field of Classification Search
CPC ................ A61K 31/403; A61K 31/407; A61K 31/4439; C07D 401/04; C07D 401/14; C07D 487/14
USPC ............... 514/333, 338, 339; 546/256, 276.7
See application file for complete search history.

(56) References Cited

FOREIGN PATENT DOCUMENTS

| | | | |
|---|---|---|---|
| WO | WO-2010145998 | A1 | 12/2010 |
| WO | WO-2013167698 | A1 | 11/2013 |
| WO | WO-2015022073 | A1 | 2/2015 |
| WO | WO-2015193339 | A1 | 12/2015 |
| WO | WO-2016120196 | A1 | 8/2016 |

OTHER PUBLICATIONS

International Search Report dated Oct. 13, 2016, for PCT Application No. PCT/EP2016/068279, filed on Aug. 1, 2016, five pages.
Written Opinion dated Oct. 13, 2016, for PCT Application No. PCT/EP2016/068279, filed on Aug. 1, 2016, six pages.

*Primary Examiner* — Brenda L Coleman
(74) *Attorney, Agent, or Firm* — Morrison & Foerster LLP

(57) ABSTRACT

Compounds of formula (I) as described herein, processes for their production and their use as pharmaceuticals.

(I)

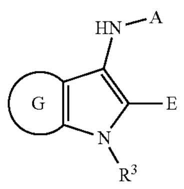

8 Claims, No Drawings

Specification includes a Sequence Listing.

1H-PYRROL-3-AMINES

CROSS REFERENCE TO RELATED APPLICATIONS

This application is the national stage of International Application No. PCT/EP2016/068279, filed internationally on Aug. 1, 2016, which claims the benefit of European Application Nos. 15179859.2, filed Aug. 5, 2015 and 15200620.1, filed Dec. 16, 2015.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 777052019500SEQLIST.txt, date recorded: Feb. 1, 2018, size: 1 KB).

FIELD OF APPLICATION OF THE INVENTION

The invention relates to substituted 1H-pyrrol-3-amine compounds, a process for their production and the use thereof.

BACKGROUND OF THE INVENTION

One of the most fundamental characteristics of cancer cells is their ability to sustain chronic proliferation whereas in normal tissues the entry into and progression through the cell divison cycle is tightly controlled to ensure a homeostasis of cell number and maintenance of normal tissue function. Loss of proliferation control was emphasized as one of the six hallmarks of cancer [Hanahan D and Weinberg R A, Cell 100, 57, 2000; Hanahan D and Weinberg R A, Cell 144, 646, 2011].

The eukaryotic cell division cycle (or cell cycle) ensures the duplication of the genome and its distribution to the daughter cells by passing through a coordinated and regulated sequence of events. The cell cycle is divided into four successive phases:

1. The G1 phase represents the time before the DNA replication, in which the cell grows and is sensitive to external stimuli.
2. In the S phase the cell replicates its DNA, and
3. in the G2 phase preparations are made for entry into mitosis.
4. In mitosis (M phase), the duplicated chromosomes get separated supported by a spindle device built from microtubules, and cell division into two daughter cells is completed.

To ensure the extraordinary high fidelity required for an accurate distribution of the chromosomes to the daughter cells, the passage through the cell cycle is strictly regulated and controlled. The enzymes that are necessary for the progression through the cycle must be activated at the correct time and are also turned off again as soon as the corresponding phase is passed. Corresponding control points ("checkpoints") stop or delay the progression through the cell cycle if DNA damage is detected, or the DNA replication or the creation of the spindle device is not yet completed. The mitotic checkpoint (also known as spindle checkpoint or spindle assembly checkpoint) controls the accurate attachment of mircrotubules of the spindle device to the kinetochors (the attachment site for microtubules) of the duplicated chromosomes. The mitotic checkpoint is active as long as unattached kinetochores are present and generates a wait-signal to give the dividing cell the time to ensure that each kinetochore is attached to a spindle pole, and to correct attachment errors. Thus the mitotic checkpoint prevents a mitotic cell from completing cell division with unattached or erroneously attached chromosomes [Suijkerbuijk S J and Kops G J, Biochem. Biophys. Acta 1786, 24, 2008; Musacchio A and Salmon E D, Nat. Rev. Mol. Cell. Biol. 8, 379, 2007]. Once all kinetochores are attached with the mitotic spindle poles in a correct bipolar (amphitelic) fashion, the checkpoint is satisfied and the cell enters anaphase and proceeds through mitosis.

The mitotic checkpoint is established by a complex network of a number of essential proteins, including members of the MAD (mitotic arrest deficient, MAD 1-3) and Bub (Budding uninhibited by benzimidazole, Bub 1-3) families, Mps1 kinase, cdc20, as well as other components [reviewed in Bolanos-Garcia V M and Blundell T L, Trends Biochem. Sci. 36, 141, 2010], many of these being over-expressed in proliferating cells (e.g. cancer cells) and tissues [Yuan B et al., Clin. Cancer Res. 12, 405, 2006]. The major function of an unsatisfied mitotic checkpoint is to keep the anaphase-promoting complex/cyclosome (APC/C) in an inactive state. As soon as the checkpoint gets satisfied the APC/C ubiquitin-ligase targets cyclin B and securin for proteolytic degradation leading to separation of the paired chromosomes and exit from mitosis.

Inactive mutations of the Ser/Thr kinase Bub1 prevented the delay in progression through mitosis upon treatment of cells of the yeast *S. cerevisiae* with microtubule-destabilizing drugs, which led to the identification of Bub1 as a mitotic checkpoint protein [Roberts B T et al., Mol. Cell Biol., 14, 8282, 1994]. A number of recent publications provide evidence that Bub1 plays multiple roles during mitosis which have been reviewed by Elowe [Elowe S, Mol. Cell. Biol. 31, 3085, 2011]. In particular, Bub1 is one of the first mitotic checkpoint proteins that binds to the kinetochores of duplicated chromosomes and probably acts as a scaffolding protein to constitute the mitotic checkpoint complex. Furthermore, via phosphorylation of histone H2A, Bub1 localizes the protein shugoshin to the centromeric region of the chromosomes to prevent premature segregation of the paired chromosomes [Kawashima et al. Science 327, 172, 2010]. In addition, together with a Thr-3 phosphorylated Histone H3 the shugoshin protein functions as a binding site for the chromosomal passenger complex which includes the proteins survivin, borealin, INCENP and Aurora B. The chromosomal passenger complex is seen as a tension sensor within the mitotic checkpoint mechanism, which dissolves erroneously formed microtubule-kinetochor attachments such as syntelic (both sister kinetochors are attached to one spindle pole) or merotelic (one kinetochor is attached to two spindle poles) attachments [Watanabe Y, Cold Spring Harb. Symp. Quant. Biol. 75, 419, 2010]. Recent data suggest that the phosphorylation of histone H2A at Thr 121 by Bub1 kinase is sufficient to localize AuroraB kinase to fulfill the attachment error correction checkpoint [Ricke et al. J. Cell Biol. 199, 931-949, 2012].

Incomplete mitotic checkpoint function has been linked with aneuploidy and tumourigenesis [Weaver B A and Cleveland D W, Cancer Res. 67, 10103, 2007; King R W, Biochim Biophys Acta 1786, 4, 2008]. In contrast, complete inhibition of the mitotic checkpoint has been recognised to result in severe chromosome missegregation and induction of apoptosis in tumour cells [Kops G J et al., Nature Rev. Cancer 5, 773, 2005; Schmidt M and Medema R H, Cell Cycle 5, 159, 2006; Schmidt M and Bastians H, Drug Res.

Updates 10, 162, 2007]. Thus, mitotic checkpoint abrogation through pharmacological inhibition of components of the mitotic checkpoint, such as Bub1 kinase, represents a new approach for the treatment of proliferative disorders, including solid tumours such as carcinomas, sarcomas, leukaemias and lymphoid malignancies or other disorders, associated with uncontrolled cellular proliferation.

The present invention relates to chemical compounds that inhibit Bub1 kinase.

Established anti-mitotic drugs such as vinca alkaloids, taxanes or epothilones activate the mitotic checkpoint, inducing a mitotic arrest either by stabilising or destabilising microtubule dynamics. This arrest prevents separation of the duplicated chromosomes to form the two daughter cells. Prolonged arrest in mitosis forces a cell either into mitotic exit without cytokinesis (mitotic slippage or adaption) or into mitotic catastrophe leading to cell death [Rieder C L and Maiato H, Dev. Cell 7, 637, 2004]. In contrast, inhibitors of Bub1 prevent the establishment and/or functionality of the mitotic checkpoint and interfere with spindle attachment error correction, which finally results in severe chromosomal missegregation, induction of apoptosis and cell death.

These findings suggest that Bub1 inhibitors should be of therapeutic value for the treatment of proliferative disorders associated with enhanced uncontrolled proliferative cellular processes such as, for example, cancer, inflammation, arthritis, viral diseases, cardiovascular diseases, or fungal diseases in a warm-blooded animal such as man. WO 2013/050438, WO 2013/092512, WO 2013/167698, WO 2014/147203, WO 2014/147204, WO2014202590, WO2014202588, WO2014202584, WO2014202583 WO2015/063003, disclose substituted indazoles, substituted pyrazoles, and substituted cycloalkylpyrazoles, which are Bub1 kinase inhibitors.

Due to the fact that especially cancer disease as being expressed by uncontrolled proliferative cellular processes in tissues of different organs of the human- or animal body still is not considered to be a controlled disease in that sufficient drug therapies already exist, there is a strong need to provide further new therapeutically useful drugs, preferably inhibiting new targets and providing new therapeutic options (e.g. drugs with improved pharmacological properties).

DESCRIPTION OF THE INVENTION

Therefore, inhibitors of Bub1 represent valuable compounds that should complement therapeutic options either as single agents or in combination with other drugs.

In accordance with a first aspect, the invention relates to a compound of formula (I), (I)

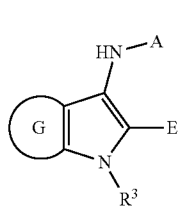

in which:

G represents a group selected from:

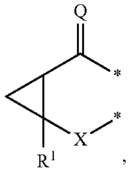 , 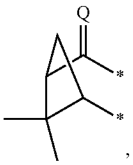 , 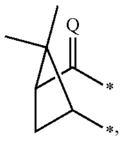 , 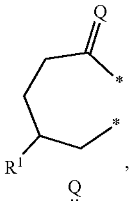 ,

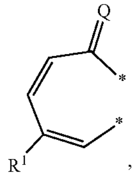 , 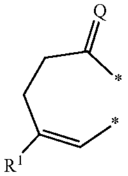 and 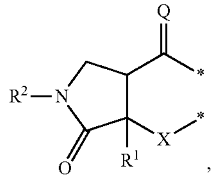 , wherein * indicates the points of attachment of said group with the rest of the molecule;

X represents $CH_2$, $CHOR^x$, or C═O;

$R^x$ represents hydrogen or $C_1$-$C_6$-alkyl;

$R^1$ represents hydrogen or $C_1$-$C_6$-alkyl;

$R^2$ represents hydrogen, $C_1$-$C_6$-alkyl, $R^{10}$—O—C(O)— or $R^7R^8$N—C(O)—;

$R^3$ represents hydrogen or $C_1$-$C_6$-alkyl;

A represents a group selected from:

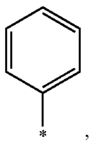 , 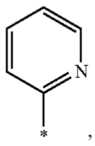 , 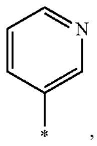 , wherein * indicates the point of attachment of said group with the rest of the molecule and said group is optionally substituted, one or more times, independently from each other, with $R^4$;

$R^4$ represents halogen, hydroxy, nitro, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-hydroxyalkyl, $C_1$-$C_4$-alkyl-C(O)—, $R^{10}$—O—C(O)—, $R^7R^8$N—C(O)—, $C_1$-$C_4$-alkyl-C(O)—NH—, $R^7R^8$N—, or $R^7R^8$N—$SO_2$—;

E represents a group

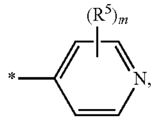

wherein * indicates the point of attachment of said group with the rest of the molecule;

$R^5$ represents, independently from each other, halogen, hydroxy, nitro, cyano, $R^9R^{10}$N—, ($R^{13}$—C(O)—)($R^{14}$—C(O)—)N—, $C_1$-$C_4$-alkyl, $C_3$-$C_6$-cycloalkyl, $C_1$-$C_6$-alkoxy, $C_1$-$C_4$-haloalkyl, $C_1$-$C_6$-haloalkoxy, $R^6$—C(O)—$NR^9$—, $R^6$—O—C(O)—$NR^9$—, $R^6$—$SO_2$—$NR^9$— or $R^7R^8$N—C(O)—$NR^9$—, Q represents O or N—OH;

$R^6$ represents, independently from each other, $C_1$-$C_6$-alkyl, $C_3$-$C_6$-cycloalkyl, 4- to 6-membered heterocycloalkyl, phenyl or heteroaryl, wherein said $C_1$-$C_6$-alkyl is optionally substituted, one or more times, independently from each other, with halogen, hydroxy, nitro, cyano, $C_1$-$C_4$-alkoxy, $C_1$-$C_4$-haloalkoxy, $C_3$-$C_6$-cycloalkyl, $R^7R^8N$— or phenyl optionally substituted, one or more times, independently from each other, with $R^4$, wherein said $C_3$-$C_6$-cycloalkyl, 4- to 6-membered heterocycloalkyl, phenyl or heteroaryl groups are optionally substituted, one or more times, independently from each other, with halogen, hydroxy, nitro, cyano, $C_1$-$C_6$-alkyl, $C_1$-$C_4$-alkoxy, $C_1$-$C_4$-haloalkyl, $R^{10}$—O—C(O)— or $C_1$-$C_4$-haloalkoxy;

$R^7$, $R^8$ represent, independently from each other, hydrogen, $C_1$-$C_6$-alkyl, $C_3$-$C_6$-cycloalkyl, $R^{10}$—O—C(O)— or phenyl, wherein said $C_1$-$C_6$-alkyl is optionally substituted, one or more times, independently from each other, with halogen, hydroxy, $C_1$-$C_4$-alkoxy, $C_1$-$C_4$-haloalkoxy, $C_3$-$C_6$-cycloalkyl optionally substituted one time with hydroxy, 4- to 6-membered heterocycloalkyl, heteroaryl, or $R^9R^{10}N$—, wherein said phenyl group is optionally substituted, one or more times, independently from each other, with $R^4$;

or, $R^7$ and $R^8$ together with the nitrogen atom to which they are attached form a 4- to 7-membered nitrogen containing heterocyclic ring, optionally containing one additional heteroatom selected from O, $NR^9$ and S, and which may be optionally substituted one or more times, independently from each other, with $R^{12}$;

whereby when two $R^{12}$ substituents are attached to the same ring carbon atom, together with the carbon atom to which they are attached, can be linked to one another in such a way that they jointly form a cyclobutane, azetidine, or oxetane group;

said azetidine being optionally substituted one time with $C_1$-$C_3$-alkyl, or, $R^7$ and $R^8$ together with the nitrogen atom to which they are attached form a group selected from:

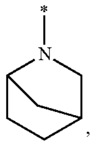,
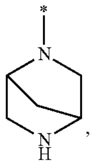,
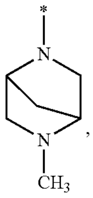,
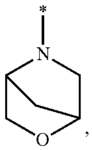, wherein * indicates the point of attachment of said group with the rest of the molecule, $R^9$ represents hydrogen, or $C_1$-$C_6$-alkyl;

$R^{10}$ represents hydrogen, $C_1$-$C_6$-alkyl or $C_3$-$C_6$-cycloalkyl;

$R^{12}$ represents halogen, hydroxy, $C_1$-$C_4$-alkyl, $C_1$-$C_4$-alkoxy, $C_1$-$C_4$-haloalkyl, $C_1$-$C_4$-haloalkoxy, or $R^9R^{10}N$—;

$R^{13}$, $R^{14}$ represent, independently from each other, $C_1$-$C_4$-alkyl, or $C_3$-$C_6$-cycloalkyl, wherein said $C_3$-$C_6$-cycloalkyl is optionally substituted, one or more times, independently from each other, with halogen;

m represents 0, 1 or 2;

or an N-oxide, a salt, a tautomer or a stereoisomer of said compound, or a salt of said N-oxide, tautomer or stereoisomer.

In a second aspect, the invention relates to compounds of formula (I) as described supra, wherein:

G represents a group selected from:

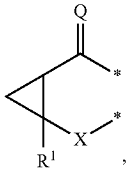,
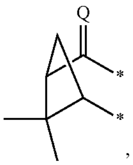,
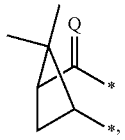,
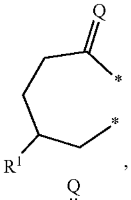,
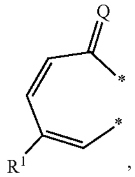,
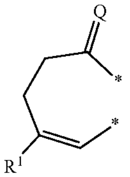
and
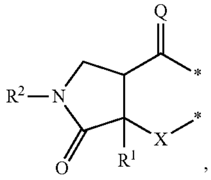, wherein * indicates the points of attachment of said group with the rest of the molecule;

X represents $CH_2$, or C═O;

$R^1$ represents hydrogen or $C_1$-$C_4$-alkyl;

$R^2$ represents hydrogen, $C_1$-$C_4$-alkyl, $R^{10}$—O—C(O)— or $R^7R^8N$—C(O)—;

$R^3$ represents hydrogen or $C_1$-$C_4$-alkyl;

A represents a group selected from:

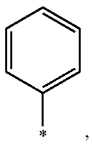,
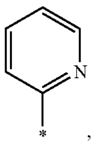,
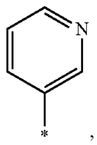, wherein * indicates the point of attachment of said group with the rest of the molecule and said group is optionally substituted, one or more times, independently from each other, with $R^4$;

$R^4$ represents halogen, hydroxy, nitro, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-hydroxyalkyl, $C_1$-$C_4$-alkyl-C(O)—, or $R^{10}$—O—C(O)—;

E represents a group

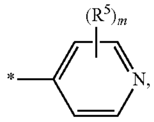, wherein * indicates the point of attachment of said group with the rest of the molecule;

$R^5$ represents, independently from each other, halogen, hydroxy, nitro, cyano, $R^9R^{10}N$—, ($R^{13}$—C(O)—)($R^{14}$—C(O)—)N—, $C_1$-$C_3$-alkyl, $C_3$-$C_4$-cycloalkyl, $C_1$-$C_3$-alkoxy, $C_1$-$C_3$-haloalkyl, $C_1$-$C_3$-haloalkoxy, $R^6$—C(O)—$NR^9$—, $R^6$—O—C(O)—$NR^9$—, $R^6$—$SO_2$—$NR^9$— or $R^7R^8N$—C(O)—$NR^9$—, Q represents O;

$R^6$ represents, independently from each other, $C_1$-$C_6$-alkyl, $C_3$-$C_6$-cycloalkyl, 4- to 6-membered heterocycloalkyl, phenyl or heteroaryl, wherein said $C_1$-$C_6$-alkyl is optionally substituted, one or more times, independently from each other, with halogen, hydroxy, nitro, cyano, $C_1$-$C_4$-alkoxy, $C_1$-$C_4$-haloalkoxy, $C_3$-$C_6$-cycloalkyl, $R^7R^8N$— or phenyl optionally substituted, one or more times, independently from each other, with $R^4$, wherein said $C_3$-$C_6$-cycloalkyl, 4- to 6-membered heterocycloalkyl, phenyl or heteroaryl groups are optionally substituted, one or more times, independently from each other, with halogen, hydroxy, nitro, cyano, $C_1$-$C_6$-alkyl, $C_1$-$C_4$-alkoxy, $C_1$-$C_4$-haloalkyl, $R^{10}$—O—C(O)— or $C_1$-$C_4$-haloalkoxy;

$R^7$, $R^8$ represent, independently from each other, hydrogen, $C_1$-$C_6$-alkyl, $C_3$-$C_6$-cycloalkyl, $R^{10}$—O—C(O)— or phenyl, wherein said $C_1$-$C_6$-alkyl is optionally substituted, one or more times, independently from each other, with halogen, hydroxy, $C_1$-$C_4$-alkoxy, $C_1$-$C_4$-haloalkoxy, $C_3$-$C_6$-cycloalkyl optionally substituted one time with hydroxy, 4- to 6-membered heterocycloalkyl, heteroaryl, or $R^9R^{10}N$—, wherein said phenyl group is optionally substituted, one or more times, independently from each other, with $R^4$;

or, $R^7$ and $R^8$ together with the nitrogen atom to which they are attached form a 5- to 6-membered nitrogen containing heterocyclic ring, optionally containing one additional heteroatom selected from O, and $NR^9$;

$R^9$ represents hydrogen, or $C_1$-$C_4$-alkyl;

$R^{10}$ represents hydrogen, $C_1$-$C_4$-alkyl or $C_3$-$C_4$-cycloalkyl;

$R^{13}$, $R^{14}$ represent, independently from each other, $C_1$-$C_3$-alkyl, or $C_3$-$C_4$-cycloalkyl, wherein said $C_3$-$C_4$-cycloalkyl is optionally substituted, one or more times, independently from each other, with halogen;

m represents 0, 1 or 2;

or an N-oxide, a salt, a tautomer or a stereoisomer of said compound, or a salt of said N-oxide, tautomer or stereoisomer.

In a third aspect, the invention relates to compounds of formula (I) as described supra, wherein:

G represents a group selected from:

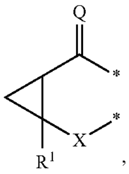 , 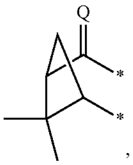 , 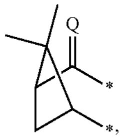 , 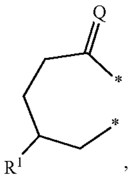 ,

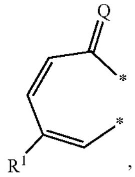 , 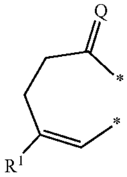 and 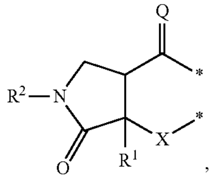 , wherein * indicates the points of attachment of said group with the rest of the molecule;

X represents $CH_2$, or C=O;

$R^1$ represents hydrogen or $C_1$-$C_4$-alkyl;

$R^2$ represents hydrogen, or $C_1$-$C_3$-alkyl;

$R^3$ represents hydrogen or $C_1$-$C_2$-alkyl;

A represents a group selected from:

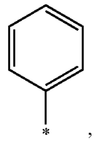 , 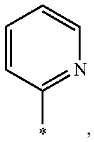 , 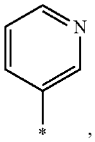 , wherein * indicates the point of attachment of said group with the rest of the molecule and said group is optionally substituted, one or more times, independently from each other, with $R^4$;

$R^4$ represents halogen, hydroxy, nitro, cyano, $C_1$-$C_2$-alkyl, $C_1$-$C_2$-alkoxy, $C_1$-$C_2$-haloalkyl, $C_1$-$C_2$-haloalkoxy, $C_1$-$C_2$-hydroxyalkyl;

E represents a group

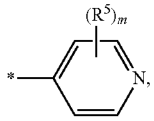

wherein * indicates the point of attachment of said group with the rest of the molecule;

$R^5$ represents, independently from each other, halogen, hydroxy, nitro, cyano, $R^9R^{10}N$—, $C_1$-alkyl, $C_3$-cycloalkyl, $C_1$-alkoxy, $C_1$-haloalkyl, $C_1$-haloalkoxy, $R^6$—C(O)—$NR^9$—, $R^6$—O—C(O)—$NR^9$—, $R^6$—$SO_2$—$NR^9$— or $R^7R^8N$—C(O)—$NR^9$—, Q represents O;

$R^6$ represents, independently from each other, $C_1$-$C_4$-alkyl, $C_3$-$C_4$-cycloalkyl, 5- to 6-membered heterocycloalkyl, phenyl or heteroaryl, wherein said $C_1$-$C_4$-alkyl is optionally substituted, one or more times, independently from each other, with halogen, hydroxy, $C_1$-alkoxy, $C_1$-haloalkoxy, wherein said $C_3$-$C_4$-cycloalkyl, 5- to 6-membered heterocycloalkyl, phenyl or heteroaryl groups are optionally substituted, one or more times, independently from each other, with halogen, hydroxy, $C_1$-alkyl, $C_1$-alkoxy, or $C_1$-haloalkyl;

$R^7$, $R^8$ represent, independently from each other, hydrogen, $C_1$-$C_4$-alkyl, $C_3$-$C_4$-cycloalkyl, wherein said $C_1$-$C_4$-alkyl is optionally substituted, one or more times, independently from each other, with halogen, hydroxy, $C_1$-alkoxy, $C_1$-haloalkoxy, $C_3$-$C_4$-cycloalkyl optionally substituted one time with hydroxy, 5- to 6-membered heterocycloalkyl, heteroaryl, or $R^9R^{10}N$—, $R^9$ represents hydrogen, or $C_1$-alkyl;

$R^{10}$ represents hydrogen, or $C_1$-alkyl;

m represents 0, or 1;

or an N-oxide, a salt, a tautomer or a stereoisomer of said compound, or a salt of said N-oxide, tautomer or stereoisomer.

In a fourth aspect, the invention relates to compounds of formula (I) as described supra, wherein:

G represents a group selected from:

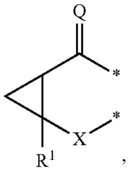,
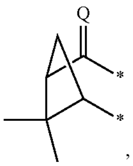,
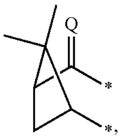,
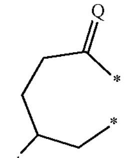,
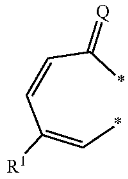
and
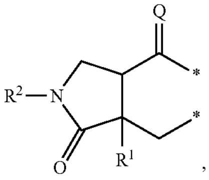, wherein * indicates the points of attachment of said group with the rest of the molecule;

X represents $CH_2$, or C═O;

$R^1$ represents hydrogen or $C_1$-alkyl;

$R^2$ represents $C_1$-alkyl;

$R^3$ represents hydrogen;

A represents a group selected from:

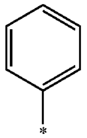 [SMILES: *c1ccccc1]

wherein * indicates the point of attachment of said group with the rest of the molecule;

E represents a group

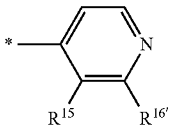

wherein * indicates the point of attachment of said group with the rest of the molecule;

Q represents O;

$R^6$ represents, independently from each other, $C_1$-$C_3$-alkyl, $C_3$-cycloalkyl, phenyl or heteroaryl, wherein said $C_1$-$C_3$-alkyl is optionally substituted, one or more times, with fluoro, wherein said $C_3$-cycloalkyl, phenyl or heteroaryl groups are optionally substituted, one or two times, independently from each other, with fluoro, $C_1$-alkyl, $C_1$-alkoxy;

$R^7$, $R^8$ represent, independently from each other, hydrogen, $C_1$-$C_2$-alkyl, or $C_3$-cycloalkyl;

$R^9$ represents hydrogen;

$R^{10}$ represents hydrogen;

$R^{15}$ represents a hydrogen or a fluorine atom;

$R^{16}$ represents hydrogen, $R^9R^{10}N$—, $R^6$—C(O)—$NR^9$—, $R^6$—O—C(O)—$NR^9$—, $R^6$—$SO_2$—$NR^9$— or $R^7R^8N$—C(O)—$NR^9$—;

or an N-oxide, a salt, a tautomer or a stereoisomer of said compound, or a salt of said N-oxide, tautomer or stereoisomer.

The invention further relates to a compound of formula (I),

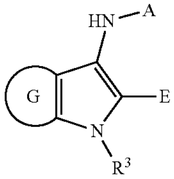

(I)

in which:

G represents a group selected from:

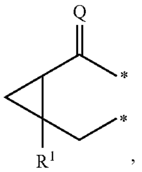,
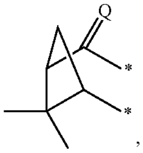,
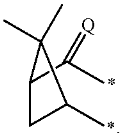,
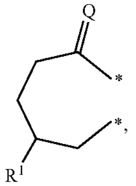,
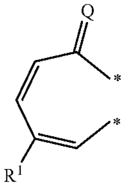
or
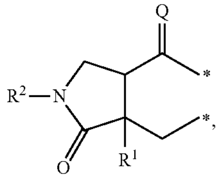, wherein * indicates the point of attachment of said group with the rest of the molecule;

$R^1$ represents hydrogen or $C_1$-$C_6$-alkyl;

$R^2$ represents hydrogen, $C_1$-$C_6$-alkyl, $R^{10}$—O—C(O)— or $R^7R^8N$—C(O)—;

$R^3$ represents hydrogen or $C_1$-$C_6$-alkyl;

A represents a group selected from:

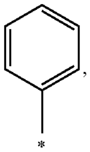,
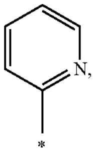
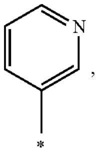, wherein * indicates the point of attachment of said group with the rest of the molecule and said group is optionally substituted, one or more times, independently from each other, with $R^4$;

$R^4$ represents halogen, hydroxy, nitro, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-hydroxyalkyl, $C_1$-$C_4$-alkyl-C(O)—, $R^{10}$—O—C(O)—, $R^7R^8N$—C(O)—, $C_1$-$C_4$-alkyl-C(O)—NH—, $R^7R^8N$—, or $R^7R^8N$—$SO_2$—;

E represents a group

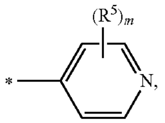

wherein * indicates the point of attachment of said group with the rest of the molecule;

$R^5$ represents, independently from each other, halogen, hydroxy, nitro, cyano, $R^9R^{10}N$—, ($R^{13}$—C(O)—)($R^{14}$—C(O)—)N—, $C_1$-$C_4$-alkyl, $C_3$-$C_6$-cycloalkyl, $C_1$-$C_6$-alkoxy, $C_1$-$C_4$-haloalkyl, $C_1$-$C_6$-haloalkoxy, $R^6$—C(O)—$NR^9$—, $R^6$—O—C(O)—$NR^9$—, $R^6$—$SO_2$—$NR^9$— or $R^7R^8N$—C(O)—$NR^9$—, Q represents O or N—OH;

$R^6$ represents, independently from each other, $C_1$-$C_6$-alkyl, $C_3$-$C_6$-cycloalkyl, 4- to 6-membered heterocycloalkyl, phenyl or heteroaryl, wherein said $C_1$-$C_6$-alkyl is optionally substituted, one or more times, independently from each other, with halogen, hydroxy, nitro, cyano, $C_1$-$C_4$-alkoxy, $C_1$-$C_4$-haloalkoxy, $C_3$-$C_6$-cycloalkyl, $R^7R^8N$— or phenyl optionally substituted, one or more times, independently from each other, with $R^4$, wherein said $C_3$-$C_6$-cycloalkyl, 4- to 6-membered heterocycloalkyl, phenyl or heteroaryl groups are optionally substituted, one or more times, independently from each other, with halogen, hydroxy, nitro, cyano, $C_1$-$C_6$-alkyl, $C_1$-$C_4$-alkoxy, $C_1$-$C_4$-haloalkyl, $R^{10}$—O—C(O)— or $C_1$-$C_4$-haloalkoxy;

$R^7$, $R^8$ represent, independently from each other, hydrogen, $C_1$-$C_6$-alkyl, $C_3$-$C_6$-cycloalkyl, $R^{10}$—O—C(O)— or phenyl, wherein said $C_1$-$C_6$-alkyl is optionally substituted, one or more times, independently from each other, with halogen, hydroxy, $C_1$-$C_4$-alkoxy, $C_1$-$C_4$-haloalkoxy, $C_3$-$C_6$-cycloalkyl optionally substituted one time with hydroxy, 4- to 6-membered heterocycloalkyl, heteroaryl, or $R^9R^{10}N$—, wherein said phenyl group is optionally substituted, one or more times, independently from each other, with $R^4$;

or, $R^7$ and $R^8$ together with the nitrogen atom to which they are attached form a 4- to 7-membered nitrogen containing heterocyclic ring, optionally containing one additional heteroatom selected from O, $NR^9$ and S, and which may be optionally substituted, one or more times, independently from each other, with $R^{12}$;

whereby when two $R^{12}$ substituents are attached to the same ring carbon atom, together with the carbon atom to which they are attached, can be linked to one another in such a way that they jointly form a cyclobutane, azetidine, or oxetane group;

said azetidine being optionally substituted one time with $C_1$-$C_3$-alkyl, or, $R^7$ and $R^8$ together with the nitrogen atom to which they are attached form a group selected from:

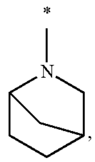,
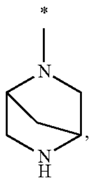,
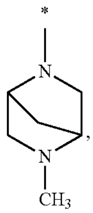,
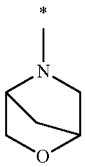

wherein * indicates the point of attachment of said group with the rest of the molecule, $R^9$ represents hydrogen, or $C_1$-$C_6$-alkyl;

$R^{10}$ represents hydrogen, $C_1$-$C_6$-alkyl or $C_3$-$C_6$-cycloalkyl;

$R^{11}$ represents hydroxy, nitro, cyano, $C_3$-$C_6$-cycloalkyl, 4- to 6-membered heterocycloalkyl, $C_1$-$C_4$-alkyl-C(O)—, $R^{10}$—O—C(O)—, $R^7R^8N$—C(O)—, $C_1$-$C_4$-alkoxy, $C_1$-$C_4$-haloalkoxy, $R^7R^8N$—, $N_3$—, $R^6$—C(O)—$NR^9$—, $R^6$—O—C(O)—$NR^9$—, $R^7R^8N$—C(O)—$NR^9$—, $R^6$—$SO_2$—$NR^9$—, $R^6$—S—, $R^6$—SO—, $R^6$—$SO_2$—, $R^7R^8N$—$SO_2$—;

wherein said $C_3$-$C_6$-cycloalkyl or 4- to 6-membered heterocycloalkyl groups are optionally substituted, one or more times, independently from each other, with halogen, hydroxy, cyano, $C_1$-$C_4$-alkyl, $C_1$-$C_4$-alkoxy, $C_1$-$C_4$-haloalkyl or $C_1$-$C_4$-haloalkoxy, wherein said $C_1$-$C_4$-alkoxy is optionally substituted with phenyl, wherein said phenyl group is optionally substituted, one or more times, independently from each other, with $R^4$, $R^{12}$ represents halogen, hydroxy, $C_1$-$C_4$-alkyl, $C_1$-$C_4$-alkoxy, $C_1$-$C_4$-haloalkyl, $C_1$-$C_4$-haloalkoxy, or $R^9R^{10}N$—;

$R^{13}$, $R^{14}$ represent, independently from each other, $C_1$-$C_4$-alkyl, or $C_3$-$C_6$-cycloalkyl, wherein said $C_3$-$C_6$-cycloalkyl is optionally substituted, one or more times, independently from each other, with halogen;

m represents 0, 1 or 2;

or an N-oxide, a salt, a tautomer or a stereoisomer of said compound, or a salt of said N-oxide, tautomer or stereoisomer.

In accordance with another aspect, the invention relates to a compound of formula (I), which is selected from the group consisting of:

rel-(5R,7S)-6,6-dimethyl-3-(phenylamino)-2-(pyridin-4-yl)-1,5,6,7-tetrahydro-4H-5,7-methanoindol-4-one, rel-(5R,7S)-2-(2-aminopyridin-4-yl)-6,6-dimethyl-3-(phenylamino)-1,5,6,7-tetrahydro-4H-5,7-methanoindol-4-one, (5R,7S or 5S,7R)-2-(2-aminopyridin-4-yl)-6,6-dimethyl-3-(phenylamino)-1,5,6,7-tetrahydro-4H-5,7-methanoindol-4-one, (5S,7R or 5R,7S)-2-(2-aminopyridin-4-yl)-6,6-dimethyl-3-(phenylamino)-1,5,6,7-tetrahydro-4H-5,7-methanoindol-4-one, N-4-[rel-(5R,7S)-6,6-dimethyl-4-oxo-3-(phenylamino)-4,5,6,7-tetrahydro-1H-5,7-methanoindol-2-yl]pyridin-2-ylacetamide, N-4-[rel-(5R,7S)-6,6-dimethyl-4-oxo-3-(phenylamino)-4,5,6,7-tetrahydro-1H-5,7-methanoindol-2-yl]pyridin-2-yl-cyclopropanecarboxamide, methyl 4-[rel-(5R,7S)-6,6-dimethyl-4-oxo-3-(phenylamino)-4,5,6,7-tetrahydro-1H-5,7-methanoindol-2-yl]pyridin-2-ylcarbamate, 1-4-[rel-(5R,7S)-6,6-dimethyl-4-oxo-3-(phenylamino)-4,5,6,7-tetrahydro-1H-5,7-methanoindol-2-yl]pyridin-2-yl-3-ethylurea, 1-cyclopropyl-3-4-[rel-(5R,7S)-6,6-dimethyl-4-oxo-3-(phenylamino)-4,5,6,7-tetrahydro-1H-5,7-methanoindol-2-yl]pyridin-2-ylurea, rel-(5R,7S)-2-(3-fluoropyridin-4-yl)-6,6-dimethyl-3-(phenylamino)-1,5,6,7-tetrahydro-4H-5,7-methanoindol-4-one, rel-(4aR,7aS)-6-methyl-3-(phenylamino)-2-(pyridin-4-yl)-1,4a,5,6,7a,8-hexahydropyrrolo[3,4-f]indole-4,7-dione, rel-(4aR,5aR)-3-(phenylamino)-2-(pyridin-4-yl)-4a,5,5a,6-tetrahydrocyclopropa[f]indol-4(1H)-one, (4aR,5aR or 4aS,5aS)-3-(phenylamino)-2-(pyridin-4-yl)-4a,5,5a,6-tetrahydrocyclopropa[f]indol-4(1H)-one, (4aS,5aS or 4aR,5aR)-3-(phenylamino)-2-(pyridin-4-yl)-4a,5,5a,6-tetrahydrocyclopropa[f]indol-4(1H)-one, rel-(4aR,5aR)-N-4-[4-oxo-3-(phenylamino)-1,4,4a,5,5a,6-hexahydrocyclopropa[f]indol-2-yl]pyridin-2-ylacetamide, rel-(4aR,5aR)-5a-methyl-3-(phenylamino)-2-(pyridin-4-yl)-4a,5,5a,6-tetrahydrocyclopropa[f]indol-4(1H)-one, (4aR,5aR or 4aS,5aS)-5a-methyl-3-(phenylamino)-2-(pyridin-4-yl)-4a,5,5a,6-tetrahydrocyclopropa[f]indol-4(1H)-one, (4aS,5aS or 4aR,5aR)-5a-methyl-3-(phenylamino)-2-(pyridin-4-yl)-4a,5,5a,6-tetrahydrocyclopropa[f]indol-4(1H)-one, N-4-[(4aR,5aR or 4aS,5aS)-5a-methyl-4-oxo-3-(phenylamino)-1,4,4a,5,5a,6-hexahydrocyclopropa[f]indol-2-yl]pyridin-2-ylacetamide, N-4-[(4aS,5aS or 4aR,5aR)-5a-methyl-4-oxo-3-(phenylamino)-1,4,4a,5,5a,6-hexahydrocyclopropa[f]indol-2-yl]pyridin-2-ylacetamide, 3-(phenylamino)-2-(pyridin-4-yl)cyclohepta[b]pyrrol-4(1H)-one, 3-(phenylamino)-2-(pyridin-4-yl)-5,6,7,8-tetrahydrocyclohepta[b]pyrrol-4(1H)-one, 2-(2-aminopyridin-4-yl)-7-methyl-3-(phenylamino)cyclohepta[b]pyrrol-4(1H)-one, (7RS)-2-(2-aminopyridin-4-yl)-7-methyl-3-(phenylamino)-5,6,7,8-tetrahydrocyclohepta[b]pyrrol-4(1H)-one, N-{4-[(7RS)-3-anilino-7-methyl-4-oxo-1,4,5,6,7,8-hexahydrocyclohepta[b]pyrrol-2-yl]pyridin-2-yl}acetamide, rel-(4aR,5aR)-2-(2-aminopyridin-4-yl)-3-anilino-5a-methyl-4a,5,5a,6-tetrahydrocyclopropa[f]indol-4(1H)-one, N-{4-[rel-(4aR,5aR)-3-anilino-5a-methyl-4-oxo-1,4,4a,5,5a,6-hexahydrocyclopropa[f]indol-2-yl]pyridin-2-yl}methanesulfonamide, N-[4-(3-anilino-7-methyl-4-oxo-1,4-dihydrocyclohepta[b]pyrrol-2-yl)pyridin-2-yl]methanesulfonamide, 1-fluoro-N-4-[rel-(4aS,5aR)-5a-methyl-4,6-dioxo-3-(phenylamino)-1,4,4a,5,5a,6-hexahydrocyclopropa[f]indol-2-yl]pyridin-2-ylcyclopropanecarboxamide, 1-fluoro-N-4-[(4aS,5aS)-5a-methyl-4-oxo-3-(phenylamino)-1,4,4a,5,5a,6-hexahydrocyclopropa[f]indol-2-yl]pyridin-2-ylcyclopropanecarboxamide, 1-fluoro-N-4-[(4aR,5aR)-5a-methyl-4-oxo-3-(phenylamino)-1,4,4a,5,5a,6-hexahydrocyclopropa[f]indol-2-yl]pyridin-2-ylcyclopropanecarboxamide, N-4-[rel-(4aS,5aR)-5a-methyl-4,6-dioxo-3-(phenylamino)-1,4,4a,5,5a,6-hexahydrocyclopropa[f]indol-2-yl]pyridin-2-ylcyclopropanecarboxamide, N-{4-[rel-(4aR,5aS)-3-Anilino-5a-methyl-4,6-dioxo-1,4,4a,5,5a,6-hexahydrocyclopropa[f]indol-2-yl]pyridin-2-yl}-1-methylcyclopropanecarboxamide, 1-methyl-N-4-[rel-(4aS,5aR)-5a-methyl-4,6-dioxo-3-(phenylamino)-1,4,4a,5,5a,6-hexahydrocyclopropa[f]indol-2-yl]pyridin-2-yl-1H-pyrazole-3-carboxamide, 4-fluoro-3-methoxy-N-4-[rel-(4aS,5aR)-5a-methyl-4,6-dioxo-3-(phenylamino)-1,4,4a,5,5a,6-hexahydrocyclopropa[f]indol-2-yl]pyridin-2-ylbenzamide, (1S,2S)-2-fluoro-N-4-[(4aS,5aS)-5a-methyl-4-oxo-3-(phenylamino)-1,4,4a,5,5a,6-hexahydrocyclopropa[f]indol-2-yl]pyridin-2-ylcyclopropanecarboxamide, (1S,2S)-2-fluoro-N-4-[(4aR,5aR)-5a-methyl-4-oxo-3-(phenylamino)-1,4,4a,5,5a,6-hexahydrocyclopropa[f]indol-2-yl]pyridin-2-ylcyclopropanecarboxamide, N-4-[(7S)-7-methyl-4-oxo-3-(phenylamino)-1,4,5,6,7,8-hexahydrocyclohepta[b]pyrrol-2-yl]pyridin-2-ylacetamide, N-4-[(7R)-7-methyl-4-oxo-3-(phenylamino)-1,4,5,6,7,8-hexahydrocyclohepta[b]pyrrol-2-yl]pyridin-2-ylacetamide, 2-fluoro-2-methyl-N-4-[(4aS,5aS)-5a-methyl-4-oxo-3-(phenylamino)-1,4,4a,5,5a,6-hexahydrocyclopropa[f]indol-2-yl]pyridin-2-ylpropanamide, 2-fluoro-2-methyl-N-4-[(4aR,5aR)-5a-methyl-4-oxo-3-(phenylamino)-1,4,4a,5,5a,6-hexahydrocyclopropa[f]indol-2-yl]pyridin-2-ylpropanamide, 1-methyl-N-4-[(4aS,5aS)-5a-methyl-4-oxo-3-(phenylamino)-1,4,4a,5,5a,6-hexahydrocyclopropa[f]indol-2-yl]pyridin-2-yl-1H-pyrazole-5-carboxamide, 1-methyl-N-4-[(4aR,5aR)-5a-methyl-4-oxo-3-(phenylamino)-1,4,4a,5,5a,6-hexahydrocyclopropa[f]indol-2-yl]pyridin-2-yl-1H-pyrazole-5-carboxamide, N-4-[(4aS,5aS)-5a-methyl-4-oxo-3-(phenylamino)-1,4,4a,5,5a,6-hexahydrocyclopropa[f]indol-2-yl]pyridin-2-yl-1H-pyrazole-3-carboxamide, N-4-[(4aR,5aR)-5a-methyl-4-oxo-3-(phenylamino)-1,4,4a,5,5a,6-hexahydrocyclopropa[f]indol-2-yl]pyridin-2-yl-1H-pyrazole-3-carboxamide, N-{4-[(4aR,5aR)-3-anilino-5a-methyl-4-oxo-1,4,4a,5,5a,6-hexahydrocyclopropa[f]indol-2-yl]pyridin-2-yl}-2,6-difluorobenzamide, N-{4-[(4aS,5aS)-3-anilino-5a-methyl-4-oxo-1,4,4a,5,5a,6-hexahydrocyclopropa[f]indol-2-yl]pyridin-2-yl}-2,6-difluorobenzamide N-{4-[(4aR,5aR)-3-anilino-5a-methyl-4-oxo-1,4,4a,5,5a,6-hexahydrocyclopropa[f]indol-2-yl]pyridin-2-yl}-4-fluoro-2-methylbenzamide N-{4-[(4aS,5aS)-3-anilino-5a-methyl-4-oxo-1,4,4a,5,5a,6-hexahydrocyclopropa[f]indol-2-yl]pyridin-2-yl}-4-fluoro-2-methylbenzamide N-{4-[(4aR,5aR)-3-anilino-5a-methyl-4-oxo-1,4,4a,5,5a,6-hexahydrocyclopropa[f]indol-2-yl]pyridin-2-yl}-3-fluoro-4-methoxybenzamide N-{4-[(4aS,5aS)-3-anilino-5a-methyl-4-oxo-1,4,4a,5,5a,6-hexahydrocyclopropa[f]indol-2-yl]pyridin-2-yl}-3-fluoro-4-methoxybenzamide or an N-oxide, a salt, a tautomer or a stereoisomer of said compound, or a salt of said N-oxide, tautomer or stereoisomer.

Another aspect of the invention relates to any of the intermediates described herein and their use for preparing a compound of formula (I) as defined herein or an N-oxide, a salt, a tautomer or a stereoisomer of said compound, or a salt of said N-oxide, tautomer or stereoisomer.

In a further embodiment of the above-mentioned aspects, the invention relates to compounds of formula (I), wherein:

G represents a group selected from:

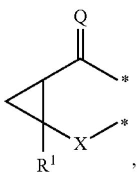 , 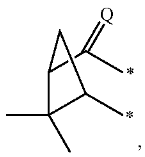 , 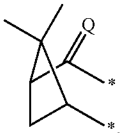 ,

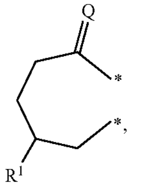 , 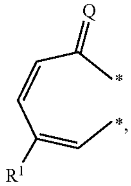 , 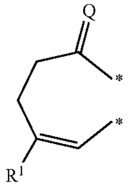 and

-continued

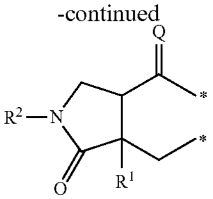

wherein * indicates the points of attachment of said group with the rest of the molecule.

In a further embodiment of the above-mentioned aspects, the invention relates to compounds of formula (I), wherein: G represents a group selected from:

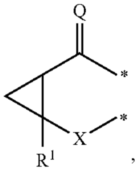,
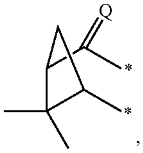,
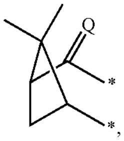
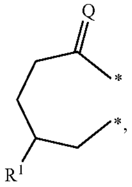
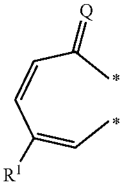
and
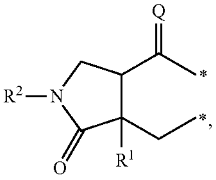

wherein * indicates the points of attachment of said group with the rest of the molecule.

In a further embodiment of the above-mentioned aspects, the invention relates to compounds of formula (I), wherein: X represents $CH_2$, $CHOR^x$, or C═O.

In a further embodiment of the above-mentioned aspects, the invention relates to compounds of formula (I), wherein: X represents $CH_2$, or C═O.

In a further embodiment of the above-mentioned aspects, the invention relates to compounds of formula (I), wherein: X represents $CH_2$.

In a further embodiment of the above-mentioned aspects, the invention relates to compounds of formula (I), wherein: X represents C═O.

In a further embodiment of the above-mentioned aspects, the invention relates to compounds of formula (I), wherein: $R^x$ represents hydrogen or $C_1$-$C_6$-alkyl.

In a further embodiment of the above-mentioned aspects, the invention relates to compounds of formula (I), wherein: $R^x$ represents hydrogen or $C_1$-$C_3$-alkyl.

In a further embodiment of the above-mentioned aspects, the invention relates to compounds of formula (I), wherein: $R^1$ represents hydrogen or $C_1$-$C_6$-alkyl.

In a further embodiment of the above-mentioned aspects, the invention relates to compounds of formula (I), wherein: $R^1$ represents hydrogen or $C_1$-$C_4$-alkyl.

In a further embodiment of the above-mentioned aspects, the invention relates to compounds of formula (I), wherein: $R^1$ represents hydrogen or $C_1$-alkyl.

In a further embodiment of the above-mentioned aspects, the invention relates to compounds of formula (I), wherein: $R^2$ represents hydrogen, $C_1$-$C_6$-alkyl, $R^{10}$—O—C(O)— or $R^7R^8N$—C(O)—.

In a further embodiment of the above-mentioned aspects, the invention relates to compounds of formula (I), wherein:

$R^2$ represents hydrogen, $C_1$-$C_4$-alkyl, $R^{10}$—O—C(O)— or $R^7R^8N$—C(O)—.

In a further embodiment of the above-mentioned aspects, the invention relates to compounds of formula (I), wherein: $R^2$ represents hydrogen, or $C_1$-$C_3$-alkyl.

In a further embodiment of the above-mentioned aspects, the invention relates to compounds of formula (I), wherein: $R^2$ represents $C_1$-alkyl.

In a further embodiment of the above-mentioned aspects, the invention relates to compounds of formula (I), wherein: $R^3$ represents hydrogen or $C_1$-$C_6$-alkyl.

In a further embodiment of the above-mentioned aspects, the invention relates to compounds of formula (I), wherein: $R^3$ represents hydrogen or $C_1$-$C_2$-alkyl.

In a further embodiment of the above-mentioned aspects, the invention relates to compounds of formula (I), wherein: $R^3$ represents hydrogen or $C_1$-$C_4$-alkyl.

In a further embodiment of the above-mentioned aspects, the invention relates to compounds of formula (I), wherein: $R^3$ represents hydrogen.

In a further embodiment of the above-mentioned aspects, the invention relates to compounds of formula (I), wherein: A represents a group selected from:

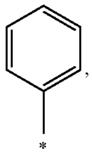,
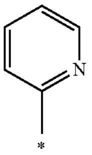
and
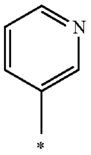

wherein * indicates the point of attachment of said group with the rest of the molecule and said group is optionally substituted, one or more times, independently from each other, with $R^4$.

In a further embodiment of the above-mentioned aspects, the invention relates to compounds of formula (I), wherein: A represents a group selected from:

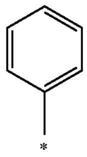

wherein * indicates the point of attachment of said group with the rest of the molecule.

In a further embodiment of the above-mentioned aspects, the invention relates to compounds of formula (I), wherein: $R^4$ represents halogen, hydroxy, nitro, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-hydroxyalkyl, $C_1$-$C_4$-alkyl-C(O)—, $R^{10}$—O—C(O)—, $R^7R^8N$—C(O)—, $C_1$-$C_4$-alkyl-C(O)—NH—, $R^7R^8N$—, or $R^7R^8N$—$SO_2$—.

In a further embodiment of the above-mentioned aspects, the invention relates to compounds of formula (I), wherein: $R^4$ represents halogen, hydroxy, nitro, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-hydroxyalkyl, $C_1$-$C_4$-alkyl-C(O)—, or $R^{10}$—O—C(O)—.

In a further embodiment of the above-mentioned aspects, the invention relates to compounds of formula (I), wherein:

$R^4$ represents halogen, hydroxy, nitro, cyano, $C_1$-$C_2$-alkyl, $C_1$-$C_2$-alkoxy, $C_1$-$C_2$-haloalkyl, $C_1$-$C_2$-haloalkoxy, $C_1$-$C_2$-hydroxyalkyl.

In a further embodiment of the above-mentioned aspects, the invention relates to compounds of formula (I), wherein:

E represents a group

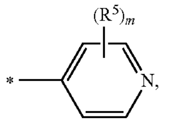

wherein * indicates the point of attachment of said group with the rest of the molecule.

In a further embodiment of the above-mentioned aspects, the invention relates to compounds of formula (I), wherein:

E represents a group

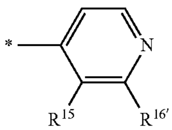

wherein * indicates the point of attachment of said group with the rest of the molecule.

In a further embodiment of the above-mentioned aspects, the invention relates to compounds of formula (I), wherein:

E represents a group

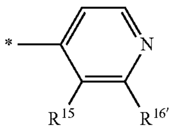

wherein * indicates the point of attachment of said group with the rest of the molecule;

$R^{15}$ represents a hydrogen or a fluorine atom;

$R^{16}$ represents hydrogen, $R^9R^{10}N$—, $R^6$—C(O)—$NR^9$—, $R^6$—O—C(O)—$NR^9$—, $R^6$—$SO_2$—$NR^9$— or $R^7R^8N$—C(O)—$NR^9$—.

In a further embodiment of the above-mentioned aspects, the invention relates to compounds of formula (I), wherein:

$R^5$ represents, independently from each other, halogen, hydroxy, nitro, cyano, $R^9R^{10}N$—, ($R^{13}$—C(O)—)($R^{14}$—C(O)—)N—, $C_1$-$C_4$-alkyl, $C_3$-$C_6$-cycloalkyl, $C_1$-$C_6$-alkoxy, $C_1$-$C_4$-haloalkyl, $C_1$-$C_6$-haloalkoxy, $R^6$—C(O)—$NR^9$—, $R^6$—O—C(O)—$NR^9$—, $R^6$—$SO_2$—$NR^9$— or $R^7R^8N$—C(O)—$NR^9$—.

In a further embodiment of the above-mentioned aspects, the invention relates to compounds of formula (I), wherein:

$R^5$ represents, independently from each other, halogen, hydroxy, nitro, cyano, $R^9R^{10}N$—, ($R^{13}$—C(O)—)($R^{14}$—C(O)—)N—, $C_1$-$C_3$-alkyl, $C_3$-$C_4$-cycloalkyl, $C_1$-$C_3$-alkoxy, $C_1$-$C_3$-haloalkyl, $C_1$-$C_3$-haloalkoxy, $R^6$—C(O)—$NR^9$—, $R^6$—O—C(O)—$NR^9$—, $R^6$—$SO_2$—$NR^9$— or $R^7R^8N$—C(O)—$NR^9$—.

In a further embodiment of the above-mentioned aspects, the invention relates to compounds of formula (I), wherein:

$R^5$ represents, independently from each other, halogen, hydroxy, nitro, cyano, $R^9R^{10}N$—, $C_1$-alkyl, $C_3$-cycloalkyl, $C_1$-alkoxy, $C_1$-haloalkyl, $C_1$-haloalkoxy, $R^6$—C(O)—$NR^9$—, $R^6$—O—C(O)—$NR^9$—, $R^6$—$SO_2$—$NR^9$— or $R^7R^8N$—C(O)—$NR^9$—.

In a further embodiment of the above-mentioned aspects, the invention relates to compounds of formula (I), wherein:

Q represents O or N—OH.

In a further embodiment of the above-mentioned aspects, the invention relates to compounds of formula (I), wherein:

Q represents O.

In a further embodiment of the above-mentioned aspects, the invention relates to compounds of formula (I), wherein:

$R^6$ represents, independently from each other, $C_1$-$C_6$-alkyl, $C_3$-$C_6$-cycloalkyl, 4- to 6-membered heterocycloalkyl, phenyl or heteroaryl, wherein said $C_1$-$C_6$-alkyl is optionally substituted, one or more times, independently from each other, with halogen, hydroxy, nitro, cyano, $C_1$-$C_4$-alkoxy, $C_1$-$C_4$-haloalkoxy, $C_3$-$C_6$-cycloalkyl, $R^7R^8N$— or phenyl optionally substituted, one or more times, independently from each other, with $R^4$, wherein said $C_3$-$C_6$-cycloalkyl, 4- to 6-membered heterocycloalkyl, phenyl or heteroaryl groups are optionally substituted, one or more times, independently from each other, with halogen, hydroxy, nitro, cyano, $C_1$-$C_6$-alkyl, $C_1$-$C_4$-alkoxy, $C_1$-$C_4$-haloalkyl, $R^{10}$—O—C(O)— or $C_1$-$C_4$-haloalkoxy.

In a further embodiment of the above-mentioned aspects, the invention relates to compounds of formula (I), wherein:

$R^6$ represents, independently from each other, $C_1$-$C_4$-alkyl, $C_3$-$C_4$-cycloalkyl, 5- to 6-membered heterocycloalkyl, phenyl or heteroaryl, wherein said $C_1$-$C_4$-alkyl is optionally substituted, one or more times, independently from each other, with halogen, hydroxy, $C_1$-alkoxy, $C_1$-haloalkoxy, wherein said $C_3$-$C_4$-cycloalkyl, 5- to 6-membered heterocycloalkyl, phenyl or heteroaryl groups are optionally substituted, one or more times, independently from each other, with halogen, hydroxy, $C_1$-alkyl, $C_1$-alkoxy, or $C_1$-haloalkyl.

In a further embodiment of the above-mentioned aspects, the invention relates to compounds of formula (I), wherein:

$R^6$ represents, independently from each other, $C_1$-$C_3$-alkyl, $C_3$-cycloalkyl, phenyl or heteroaryl, wherein said $C_1$-$C_3$-alkyl is optionally substituted, one or more times, with fluoro, wherein said $C_3$-cycloalkyl, phenyl or heteroaryl groups are optionally substituted, one or two times, independently from each other, with fluoro, $C_1$-alkyl, $C_1$-alkoxy;

In a further embodiment of the above-mentioned aspects, the invention relates to compounds of formula (I), wherein:

$R^7$, $R^8$ represent, independently from each other, hydrogen, $C_1$-$C_6$-alkyl, $C_3$-$C_6$-cycloalkyl, $R^{10}$—O—C(O)— or phenyl, wherein said $C_1$-$C_6$-alkyl is optionally substituted, one or more times, independently from each other, with halogen, hydroxy, $C_1$-$C_4$-alkoxy, $C_1$-$C_4$-haloalkoxy, $C_3$-$C_6$-cycloalkyl optionally substituted one time with hydroxy, 4- to 6-membered heterocycloalkyl, heteroaryl, or $R^9R^{10}N$—, wherein said phenyl group is optionally substituted, one or more times, independently from each other, with $R^4$.

In a further embodiment of the above-mentioned aspects, the invention relates to compounds of formula (I), wherein:

$R^7$ and $R^8$ together with the nitrogen atom to which they are attached form a 4- to 7-membered nitrogen containing heterocyclic ring, optionally containing one additional heteroatom selected from O, $NR^9$ and S, and which may be optionally substituted one or more times, independently from each other, with $R^{12}$.

whereby when two $R^{12}$ substituents are attached to the same ring carbon atom, together with the carbon atom to which they are attached, can be linked to one another in such a way that they jointly form a cyclobutane, azetidine, or oxetane group;

said azetidine being optionally substituted one time with $C_1$-$C_3$-alkyl.

In a further embodiment of the above-mentioned aspects, the invention relates to compounds of formula (I), wherein: $R^7$ and $R^8$ together with the nitrogen atom to which they are attached form a group selected from:

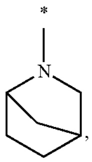, 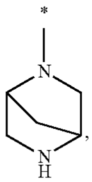, 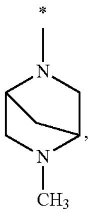, 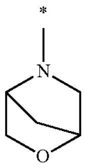

wherein * indicates the point of attachment of said group with the rest of the molecule.

In a further embodiment of the above-mentioned aspects, the invention relates to compounds of formula (I), wherein: $R^7$, $R^8$ represent, independently from each other, hydrogen, $C_1$-$C_6$-alkyl, $C_3$-$C_6$-cycloalkyl, $R^{10}$—O—C(O)— or phenyl, wherein said $C_1$-$C_6$-alkyl is optionally substituted, one or more times, independently from each other, with halogen, hydroxy, $C_1$-$C_4$-alkoxy, $C_1$-$C_4$-haloalkoxy, $C_3$-$C_6$-cycloalkyl optionally substituted one time with hydroxy, 4- to 6-membered heterocycloalkyl, heteroaryl, or $R^9R^{10}N$—, wherein said phenyl group is optionally substituted, one or more times, independently from each other, with $R^4$.

In a further embodiment of the above-mentioned aspects, the invention relates to compounds of formula (I), wherein: $R^7$ and $R^8$ together with the nitrogen atom to which they are attached form a 5- to 6-membered nitrogen containing heterocyclic ring, optionally containing one additional heteroatom selected from O , and $NR^9$.

In a further embodiment of the above-mentioned aspects, the invention relates to compounds of formula (I), wherein: $R^7$, $R^8$ represent, independently from each other, hydrogen, $C_1$-$C_4$-alkyl, $C_3$-$C_4$-cycloalkyl, wherein said $C_1$-$C_4$-alkyl is optionally substituted, one or more times, independently from each other, with halogen, hydroxy, $C_1$-alkoxy, $C_1$-haloalkoxy, $C_3$-$C_4$-cycloalkyl optionally substituted one time with hydroxy, 5- to 6-membered heterocycloalkyl, heteroaryl, or $R^9R^{10}N$—.

In a further embodiment of the above-mentioned aspects, the invention relates to compounds of formula (I), wherein: $R^7$, $R^8$ represent, independently from each other, hydrogen, $C_1$-$C_2$-alkyl, or $C_3$-cycloalkyl.

In a further embodiment of the above-mentioned aspects, the invention relates to compounds of formula (I), wherein: $R^9$ represents hydrogen, or $C_1$-$C_6$-alkyl.

In a further embodiment of the above-mentioned aspects, the invention relates to compounds of formula (I), wherein: $R^9$ represents hydrogen, or $C_1$-$C_4$-alkyl.

In a further embodiment of the above-mentioned aspects, the invention relates to compounds of formula (I), wherein: $R^9$ represents hydrogen, or $C_1$-alkyl.

In a further embodiment of the above-mentioned aspects, the invention relates to compounds of formula (I), wherein: $R^9$ represents hydrogen.

In a further embodiment of the above-mentioned aspects, the invention relates to compounds of formula (I), wherein: $R^{10}$ represents hydrogen, $C_1$-$C_6$-alkyl or $C_3$-$C_6$-cycloalkyl.

In a further embodiment of the above-mentioned aspects, the invention relates to compounds of formula (I), wherein: $R^{10}$ represents hydrogen, $C_1$-$C_4$-alkyl or $C_3$-$C_4$-cycloalkyl.

In a further embodiment of the above-mentioned aspects, the invention relates to compounds of formula (I), wherein: $R^{10}$ represents hydrogen, or $C_1$-alkyl.

In a further embodiment of the above-mentioned aspects, the invention relates to compounds of formula (I), wherein: $R^{10}$ represents hydrogen.

In a further embodiment of the above-mentioned aspects, the invention relates to compounds of formula (I), wherein: $R^{12}$ represents halogen, hydroxy, $C_1$-$C_4$-alkyl, $C_1$-$C_4$-alkoxy, $C_1$-$C_4$-haloalkyl, $C_1$-$C_4$-haloalkoxy, or $R^9R^{10}N$—.

In a further embodiment of the above-mentioned aspects, the invention relates to compounds of formula (I), wherein: $R^{13}$, $R^{14}$ represent, independently from each other, $C_1$-$C_4$-alkyl, or $C_3$-$C_6$-cycloalkyl, wherein said $C_3$-$C_6$-cycloalkyl is optionally substituted, one or more times, independently from each other, with halogen.

In a further embodiment of the above-mentioned aspects, the invention relates to compounds of formula (I), wherein: $R^{13}$, $R^{14}$ represent, independently from each other, $C_1$-$C_3$-alkyl, or $C_3$-$C_4$-cycloalkyl, wherein said $C_3$-$C_4$-cycloalkyl is optionally substituted, one or more times, independently from each other, with halogen.

In a further embodiment of the above-mentioned aspects, the invention relates to compounds of formula (I), wherein: m represents 0, 1 or 2.

In a further embodiment of the above-mentioned aspects, the invention relates to compounds of formula (I), wherein: m represents 0, or 1.

In a further embodiment of the above-mentioned aspects, the invention relates to compounds of formula (I), wherein: m represents 0.

In a further embodiment of the above-mentioned aspects, the invention relates to compounds of formula (I), wherein: m represents 1.

In a further embodiment of the above-mentioned aspects, the invention relates to compounds of formula (I), wherein: $R^{15}$ represents a hydrogen or a fluorine atom.

In a further embodiment of the above-mentioned aspects, the invention relates to compounds of formula (I), wherein: $R^{16}$ represents hydrogen, $R^9R^{10}N$—, $R^6$—C(O)—$NR^9$—, $R^6$—O—C(O)—$NR^9$—, $R^6$—$SO_2$—$NR^9$— or $R^7R^8N$—C(O)—$NR^9$—.

One aspect of the invention are compounds of formula (I) as described in the examples, as characterized by their names in the title, as claimed in claims 1 to 5, and their structures as well as the subcombinations of all residues specifically disclosed in the compounds of the examples.

Another aspect of the present invention are the intermediates as used for their synthesis.

A further aspect of the invention are compounds according to the invention, which are present as their salts.

It is to be understood that the present invention relates to any sub-combination within any embodiment or aspect of the present invention of compounds of formula (I) according to the invention, supra.

More particularly still, the present invention covers compounds of formula (I) according to the invention which are disclosed in the Example section of this text, infra.

In accordance with another aspect, the present invention covers methods of preparing compounds of formula (I) of the present invention, said methods comprising the steps as described in the Experimental Section herein.

Another embodiment of the invention are compounds according to the claims as disclosed in the Claims section wherein the definitions are limited according to the preferred or more preferred definitions as disclosed below or specifically disclosed residues of the exemplified compounds and subcombinations thereof.

Definitions

Constituents which are optionally substituted as stated herein, may be substi-tuted, unless otherwise noted, one or more times, independently from one another at any possible position. When any variable occurs more than one time in any constituent, each definition is independent. For example, when $R^1$, $R^2$, $R^3$, $R^4$, $R^5$, $R^6$, $R^7$, $R^8$, $R^9$, $R^{10}$, $R^{11}$, $R^{12}$, $R^{13}$, and/or $R^{14}$, occur more than one time in any compound of formula (I) each definition of $R^1$, $R^2$, $R^3$, $R^4$, $R^5$, $R^6$, $R^7$, $R^8$, $R^9$, $R^{10}$, $R^{11}$, $R^{12}$, $R^{13}$, and $R^{14}$ is independent.

Should a constituent be composed of more than one part, e.g. $C_1$-$C_4$-alkoxy-$C_1$-$C_4$-alkyl-, the position of a possible substituent can be at any of these parts at any suitable position.

A hyphen at the beginning or at the end of the constituent marks the point of attachment with the rest of the molecule. Should a ring be substituted the substitutent could be at any suitable position of the ring, also on a ring nitrogen atom if suitable, unless indicated otherwise.

The term "comprising" when used in the specification includes "consisting of".

If it is referred to "as mentioned above" or "mentioned above" within the description it is referred to any of the disclosures made within the specification in any of the preceding pages.

"suitable" within the sense of the invention means chemically possible to be made by methods within the knowledge of a skilled person.

The terms as mentioned in the present text have preferably the following meanings:

The term "halogen atom", "halo-" or "Hal-" is to be understood as meaning a fluorine, chlorine, bromine or iodine atom, preferably a fluorine, chlorine, bromine or iodine atom.

The term "$C_1$-$C_6$-alkyl" is to be understood as preferably meaning a linear or branched, saturated, monovalent hydrocarbon group having 1, 2, 3, 4, 5 or carbon atoms, e.g. a methyl, ethyl, propyl, butyl, pentyl, hexyl, iso-propyl, iso-butyl, sec-butyl, tert-butyl, iso-pentyl, 2-methylbutyl, 1-methylbutyl, 1-ethylpropyl, 1,2-dimethylpropyl, neo-pentyl, 1,1-dimethylpropyl, 4-methylpentyl, 3-methylpentyl, 2-methylpentyl, 1-methylpentyl, 2-ethylbutyl, 1-ethylbutyl, 3,3-dimethylbutyl, 2,2-dimethylbutyl, 1,1-dimethylbutyl, 2,3-dimethylbutyl, 1,3-dimethylbutyl or 1,2-dimethylbutyl group, or an isomer thereof, particularly 1, 2, 3 or 4 carbon atoms ("$C_1$-$C_4$-alkyl"), e.g. a methyl, ethyl, propyl, butyl, iso-propyl, iso-butyl, sec-butyl, tert-butyl group, more particularly 1, 2, or 3 carbon atoms ("$C_1$-$C_3$-alkyl") e.g. a methyl, ethyl, n-propyl- or iso-propyl group.

The term "$C_2$-$C_4$-alkenyl" is to be understood as meaning a linear or branched, monovalent hydrocarbon group, which contains one or two double bonds, and which has 2, 3 or 4 carbon atoms, particularly 2 or 3 carbon atoms ("$C_2$-$C_3$-alkenyl"), it being understood that in the case in which said alkenyl group contains more than one double bond, then said double bonds may be isolated from, or conjugated with, each other. Said alkenyl group is, for example, a vinyl, allyl, (E)-2-methylvinyl, (Z)-2-methylvinyl, homoallyl, (E)-but-2-enyl, (Z)-but-2-enyl, (E)-but-1-enyl, (Z)-but-1-enyl, iso-propenyl, 2-methylprop-2-enyl, 1-methylprop-2-enyl, 2-methylprop-1-enyl, (E)-1-methylprop-1-enyl, (Z)-1-methylprop-1-enyl, or buta-1,3-dienyl group. Particularly, said group is vinyl or allyl.

The term "$C_1$-$C_4$-haloalkyl" is to be understood as preferably meaning a linear or branched, saturated, monovalent hydrocarbon group in which the term "$C_1$-$C_4$-alkyl" is defined supra, and in which one or more hydrogen atoms is replaced by a halogen atom, in identically or differently, i.e. one halogen atom being independent from another. Particularly, said halogen atom is F. Said $C_1$-$C_4$-haloalkyl group is, for example, $—CF_3$, $—CHF_2$, $—CH_2F$, $—CF_2CF_3$, or $—CH_2CF_3$.

The term "$C_1$-$C_6$-alkoxy" is to be understood as preferably meaning a linear or branched, saturated, monovalent, hydrocarbon group of formula —O-alkyl, in which the term "alkyl" is defined supra, e.g. a methoxy, ethoxy, n-propoxy, iso-propoxy, n-butoxy, iso-butoxy, tert-butoxy or sec-butoxy group, or an isomer thereof.

The term "$C_1$-$C_6$-haloalkoxy" is to be understood as preferably meaning a linear or branched, saturated, monovalent $C_1$-$C_4$-alkoxy group, as defined supra, in which one or more of the hydrogen atoms is replaced, in identically or differently, by a halogen atom. Particularly, said halogen atom is F. Said $C_1$-$C_6$-haloalkoxy group is, for example, $—OCF_3$, $—OCHF_2$, $—OCH_2F$, $—OCF_2CF_3$, or $—OCH_2CF_3$.

The term "$C_3$-$C_6$-cycloalkyl" is to be understood as meaning a saturated, monovalent, mono-, or bicyclic hydrocarbon ring which contains 3, 4, 5 or 6 carbon atoms ("$C_3$-$C_6$-cycloalkyl"). Said $C_3$-$C_6$-cycloalkyl group is for example, a monocyclic hydrocarbon ring, e.g. a cyclopropyl, cyclobutyl, cyclopentyl or cyclohexyl, or a bicyclic hydrocarbon ring.

The term "heteroaryl" is understood as meaning a monovalent, monocyclic, aromatic ring system having 5, or 6, ring atoms (a "5- to 6-membered heteroaryl" group), which contains at least one ring heteroatom atom and optionally one, two or three further ring heteroatoms from the series N, $NR^{10}$, O and/or S, and which is bound via a ring carbon atom or, unless otherwise defined, optionally via a ring nitrogen atom (when allowed by valency). $R^{10}$ is as defined herein. Optionally, said 5- to 6-membered heteroaryl can be fused with a benzene ring (benzofused). Preferred heteroaryl benzofused groups include, but are not limited to, 1,3-Benzothiazolyl.

Said heteroaryl group can be a 5-membered heteroaryl group, such as, for example, thienyl, furanyl, pyrrolyl, oxazolyl, thiazolyl, imidazolyl, pyrazolyl, isoxazolyl, isothiazolyl, oxadiazolyl, triazolyl, thiadiazolyl or tetrazolyl; or a 6-membered heteroaryl group, such as, for example, pyridinyl, pyridazinyl, pyrimidinyl, pyrazinyl or triazinyl. In general, and unless otherwise mentioned, the heteroarylic or heteroarylenic radicals include all the possible isomeric forms thereof, e.g.: tautomers and positional isomers with respect to the point of linkage to the rest of the molecule. Thus, for some illustrative non-restricting example, the term pyridinyl includes pyridin-2-yl, pyridin-3-yl and pyridin-4-yl; or the term thienyl includes thien-2-yl and thien-3-yl.

The term “4- to 7-membered heterocycloalkyl” or “4- to 7-membered heterocyclic ring”, is to be understood as meaning a saturated or partially unsaturated, monovalent, mono- or bicyclic hydrocarbon ring which contains 3, 4, 5 or 6, carbon atoms, and one or more heteroatom-containing groups selected from O, S, S(═O), $S({=}O)_2$, and $NR^{10}$, in which $R^{10}$ is as defined herein; optionally one ring carbon atom is replaced with a C(═O) group, it being possible for said heterocycloalkyl group to be attached to the rest of the molecule via any one of the carbon atoms or, if present, the nitrogen atom.

Particularly, said 4- to 7-membered heterocycloalkyl can contain 3, 4, or 5 carbon atoms, and one or more of the above-mentioned heteroatom-containing groups (a “4- to 6-membered heterocycloalkyl”), more particularly said heterocycloalkyl can contain 4 or 5 carbon atoms, and one or more of the above-mentioned heteroatom-containing groups (a “5- to 6-membered heterocycloalkyl”).

Particularly, without being limited thereto, said heterocycloalkyl can be a 4-membered ring, such as an azetidinyl, oxetanyl, or a 5-membered ring, such as tetrahydrofuranyl, dioxolinyl, pyrrolidinyl, imidazolidinyl, pyrazolidinyl, pyrrolinyl, or a 6-membered ring, such as tetrahydropyranyl, piperidinyl, morpholinyl, dithianyl, thiomorpholinyl, piperazinyl, or trithianyl, or a 7-membered ring, such as a diazepanyl ring, for example. Optionally, said heterocycloalkyl can be benzo fused.

Said heterocyclyl can be bicyclic, such as, without being limited thereto, a 5,5-membered ring, e.g. a hexahydrocyclopenta[c]pyrrol-2(1H)-yl ring, or a 5,6-membered bicyclic ring, e.g. a hexahydropyrrolo[1,2-a]pyrazin-2(1H)-yl ring.

As mentioned supra, said nitrogen atom-containing ring can be partially unsaturated, i.e. it can contain one or more double bonds, such as, without being limited thereto, a 2,5-dihydro-1H-pyrrolyl, 4H-[1,3,4]thiadiazinyl, 4,5-dihydrooxazolyl, or 4H-[1,4]thiazinyl ring, for example, or, it may be benzo-fused, such as, without being limited thereto, a dihydroisoquinolinyl ring, for example.

The term “$C_1$-$C_6$”, as used throughout this text, e.g. in the context of the definition of “$C_1$-$C_6$-alkyl” or “$C_1$-$C_6$-alkoxy” is to be understood as meaning an alkyl group having a finite number of carbon atoms of 1 to 6, i.e. 1, 2, 3, 4, 5, or 6 carbon atoms. It is to be understood further that said term “$C_1$-$C_6$” is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$, $C_1$-$C_6$; particularly $C_1$-$C_2$, $C_1$-$C_3$, $C_1$-$C_4$, $C_1$-$C_5$, $C_1$-$C_6$; more particularly $C_1$-$C_4$; in the case of “$C_1$-$C_6$-haloalkyl” or “$C_1$-$C_6$-haloalkoxy” even more particularly $C_1$-$C_2$.

Further, as used herein, the term “$C_3$-$C_6$”, as used throughout this text, e.g. in the context of the definition of “$C_3$-$C_6$-cycloalkyl”, is to be understood as meaning a cycloalkyl group having a finite number of carbon atoms of 3 to 6, i.e. 3, 4, 5 or 6 carbon atoms. It is to be understood further that said term “$C_3$-$C_6$” is to be interpreted as any sub-range comprised therein, e.g. $C_3$-$C_6$, $C_4$-$C_5$, $C_3$-$C_5$, $C_3$-$C_4$, $C_4$-$C_6$, $C_5$-$C_6$; particularly $C_3$-$C_6$.

The term “substituted” means that one or more hydrogens on the designated atom is replaced with a selection from the indicated group, provided that the designated atom’s normal valency under the existing circumstances is not exceeded, and that the substitution results in a stable compound. Combinations of substituents and/or variables are permissible only if such combinations result in stable compounds.

The term “optionally substituted” means optional substitution with the specified groups, radicals or moieties.

Ring system substituent means a substituent attached to an aromatic or nonaromatic ring system which, for example, replaces an available hydrogen on the ring system.

As used herein, the term “one or more”, e.g. in the definition of the substituents of the compounds of the general formulae of the present invention, is understood as meaning “one, two, three, four or five, particularly one, two, three or four, more particularly one, two or three, even more particularly one or two”.

The invention also includes all suitable isotopic variations of a compound of the invention. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Certain isotopic variations of a compound of the invention, for example, those in which one or more radioactive isotopes such as $^3H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Isotopic variations of a compound of the invention can generally be prepared by conventional procedures known by a person skilled in the art such as by the illustrative methods or by the preparations described in the examples hereafter using appropriate isotopic variations of suitable reagents.

Where the plural form of the word compounds, salts, polymorphs, hydrates, solvates and the like, is used herein, this is taken to mean also a single compound, salt, polymorph, isomer, hydrate, solvate or the like.

By “stable compound” or “stable structure” is meant a compound that is sufficiently robust to survive isolation to a useful degree of purity from a reaction mixture, and formulation into an efficacious therapeutic agent.

The compounds of this invention may contain one or more asymmetric centre, depending upon the location and nature of the various substituents desired. Asymmetric carbon atoms may be present in the (R) or (S) configuration, resulting in racemic mixtures in the case of a single asymmetric centre, and diastereomeric mixtures in the case of multiple asymmetric centres. In certain instances, asymmetry may also be present due to restricted rotation about a given bond, for example, the central bond adjoining two substituted aromatic rings of the specified compounds.

Substituents on a ring may also be present in either cis or trans form. It is intended that all such configurations (including enantiomers and diastereomers), are included within the scope of the present invention.

Preferred compounds are those which produce the more desirable biological activity. Separated, pure or partially purified isomers and stereoisomers or racemic or diastereomeric mixtures of the compounds of this invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., chiral HPLC columns), with or without conventional derivatisation, optimally chosen to maximise the separation of the enantiomers. Suitable chiral HPLC columns are manufactured by Daicel, e.g., Chiracel OD and Chiracel OJ among many others, all routinely selectable. Enzymatic separations, with or without derivatisation, are also useful. The optically active compounds of this invention can likewise be obtained by chiral syntheses utilizing optically active starting materials.

In order to limit different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. R- or S-isomers, or E- or Z-isomers, in any ratio. Isolation of a single stereoisomer, e.g. a single enantiomer or a single diastereomer, of a compound of the present invention may be achieved by any suitable state of the art method, such as chromatography, especially chiral chromatography, for example.

Further, the compounds of the present invention may exist as tautomers. For example, any compound of the present invention which contains a pyrazole moiety as a heteroaryl group for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers, namely:

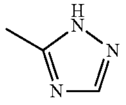

1H-tautomer

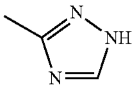

2H-tautomer

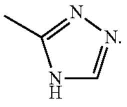

4H-tautomer

The present invention includes all possible tautomers of the compounds of the present invention as single tautomers, or as any mixture of said tautomers, in any ratio.

Further, the compounds of the present invention can exist as N-oxides, which are defined in that at least one nitrogen of the compounds of the present invention is oxidised. The present invention includes all such possible N-oxides.

The present invention also relates to useful forms of the compounds as disclosed herein, such as metabolites, hydrates, solvates, prodrugs, salts, in particular pharmaceutically acceptable salts, and co-precipitates.

The compounds of the present invention can exist as a hydrate, or as a solvate, wherein the compounds of the present invention contain polar solvents, in particular water, methanol or ethanol for example as structural element of the crystal lattice of the compounds. The amount of polar solvents, in particular water, may exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates.

Further, the compounds of the present invention can exist in free form, e.g. as a free base, or as a free acid, or as a zwitterion, or can exist in the form of a salt. Said salt may be any salt, either an organic or inorganic addition salt, particularly any pharmaceutically acceptable organic or inorganic addition salt, customarily used in pharmacy.

The term "pharmaceutically acceptable salt" refers to a relatively non-toxic, inorganic or organic acid addition salt of a compound of the present invention. For example, see S. M. Berge, et al. "Pharmaceutical Salts," J. Pharm. Sci. 1977, 66, 1-19.

A suitable pharmaceutically acceptable salt of the compounds of the present invention may be, for example, an acid-addition salt of a compound of the present invention bearing a nitrogen atom, in a chain or in a ring, for example, which is sufficiently basic, such as an acid-addition salt with an inorganic acid, such as hydrochloric, hydrobromic, hydroiodic, sulfuric, bisulfuric, phosphoric, or nitric acid, for example, or with an organic acid, such as formic, acetic, acetoacetic, pyruvic, trifluoroacetic, propionic, butyric, hexanoic, heptanoic, undecanoic, lauric, benzoic, salicylic, 2-(4-hydroxybenzoyl)-benzoic, camphoric, cinnamic, cyclopentanepropionic, digluconic, 3-hydroxy-2-naphthoic, nicotinic, pamoic, pectinic, persulfuric, 3-phenylpropionic, picric, pivalic, 2-hydroxyethanesulfonate, itaconic, sulfamic, trifluoromethanesulfonic, dodecylsulfuric, ethansulfonic, benzenesulfonic, para-toluenesulfonic, methansulfonic, 2-naphthalenesulfonic, naphthalinedisulfonic, camphorsulfonic acid, citric, tartaric, stearic, lactic, oxalic, malonic, succinic, malic, adipic, alginic, maleic, fumaric, D-gluconic, mandelic, ascorbic, glucoheptanoic, glycerophosphoric, aspartic, sulfosalicylic, hemisulfuric, or thiocyanic acid, for example.

Further, another suitably pharmaceutically acceptable salt of a compound of the present invention which is sufficiently acidic, is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, dicyclohexylamine, 1,6-hexadiamine, ethanolamine, glucosamine, sarcosine, serinol, tris-hydroxy-methyl-aminomethane, aminopropandiol, sovak-base, 1-amino-2,3,4-butantriol. Additionally, basic nitrogen containing groups may be quaternised with such agents as lower alkyl halides such as methyl, ethyl, propyl, and butyl chlorides, bromides and iodides; dialkyl sulfates like dimethyl, diethyl, and dibutyl sulfate; and diamyl sulfates, long chain halides such as decyl, lauryl, myristyl and strearyl chlorides, bromides and iodides, aralkyl halides like benzyl and phenethyl bromides and others.

Those skilled in the art will further recognise that acid addition salts of the claimed compounds may be prepared by reaction of the compounds with the appropriate inorganic or organic acid via any of a number of known methods. Alternatively, alkali and alkaline earth metal salts of acidic compounds of the invention are prepared by reacting the compounds of the invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae such as "hydrochloride", "trifluoroacetate", "sodium salt", or "x HCl", "x CF3COOH", "x Na+", for example, are to be understood as not a stoichiometric specification, but solely as a salt form.

This applies analogously to cases in which synthesis intermediates or example compounds or salts thereof have been obtained, by the preparation and/or purification processes described, as solvates, such as hydrates with (if defined) unknown stoichiometric composition.

The salts include water-insoluble and, particularly, water-soluble salts.

Furthermore, derivatives of the compounds according to the invention and the salts thereof which are converted into a compound according to the invention or a salt thereof in a biological system (bioprecursors or pro-drugs) are covered by the invention. Said biological system is e.g. a mammalian organism, particularly a human subject. The bioprecursor is, for example, converted into the compound according to the invention or a salt thereof by metabolic processes.

As used herein, the term "in vivo hydrolysable ester" is understood as meaning an in vivo hydrolysable ester of a compound of the present invention containing a carboxy or hydroxy group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention.

An in vivo hydrolysable ester of a compound of the present invention containing a hydroxy group includes inorganic esters such as phosphate esters and [alpha]-acyloxyalkyl ethers and related compounds which as a result of the in vivo hydrolysis of the ester breakdown to give the parent hydroxy group. Examples of [alpha]-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl. The present invention covers all such esters.

Furthermore, the present invention includes all possible crystalline forms, or polymorphs, of the compounds of the present invention, either as single polymorphs, or as a mixture of more than one polymorphs, in any ratio.

In the context of the properties of the compounds of the present invention the term "pharmacokinetic profile" means one single parameter or a combination thereof including permeability, bioavailability, exposure, and pharmacodynamic parameters such as duration, or magnitude of pharmacological effect, as measured in a suitable experiment. Compounds with improved pharmacokinetic profiles can, for example, be used in lower doses to achieve the same effect, may achieve a longer duration of action, or a may achieve a combination of both effects.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered. Any such combination of a compound of the present invention with an anti-cancer agent as defined below is an embodiment of the invention.

The term "(chemotherapeutic) anti-cancer agents", includes but is not limited to 131I-chTNT, abarelix, abiraterone, aclarubicin, ado-trastuzumab emtansine, afatinib, aflibercept, aldesleukin, alectinib, alemtuzumab, alendronic acid, alitretinoin, altretamine, amifostine, aminoglutethimide, hexyl aminolevulinate, amrubicin, amsacrine, anastrozole, ancestim, anethole dithiolethione, anetumab ravtansine, angiotensin II, antithrombin III, aprepitant, arcitumomab, arglabin, arsenic trioxide, asparaginase, axitinib, azacitidine, basiliximab, belotecan, bendamustine, besilesomab, belinostat, bevacizumab, bexarotene, bicalutamide, bisantrene, bleomycin, blinatumomab, bortezomib, buserelin, bosutinib, brentuximab vedotin, busulfan, cabazitaxel, cabozantinib, calcitonine, calcium folinate, calcium levofolinate, capecitabine, capromab, carboplatin, carboquone, carfilzomib, carmofur, carmustine, catumaxomab, celecoxib, celmoleukin, ceritinib, cetuximab, chlorambucil, chlormadinone, chlormethine, cidofovir, cinacalcet, cisplatin, cladribine, clodronic acid, clofarabine, cobimetinib, copanlisib, crisantaspase, crizotinib, cyclophosphamide, cyproterone, cytarabine, dacarbazine, dactinomycin, daratumumab, darbepoetin alfa, dabrafenib, dasatinib, daunorubicin, decitabine, degarelix, denileukin diftitox, denosumab, depreotide, deslorelin, dianhydrogalactitol, dexrazoxane, dibrospidium chloride, dianhydrogalactitol, diclofenac, dinutuximab, docetaxel, dolasetron, doxifluridine, doxorubicin, doxorubicin+estrone, dronabinol, eculizumab, edrecolomab, elliptinium acetate, elotuzumab, eltrombopag, endostatin, enocitabine, enzalutamide, epirubicin, epitiostanol, epoetin alfa, epoetin beta, epoetin zeta, eptaplatin, eribulin, erlotinib, esomeprazole, estradiol, estramustine, ethinylestradiol, etoposide, everolimus, exemestane, fadrozole, fentanyl, filgrastim, fluoxymesterone, floxuridine, fludarabine, fluorouracil, flutamide, folinic acid, formestane, fosaprepitant, fotemustine, fulvestrant, gadobutrol, gadoteridol, gadoteric acid meglumine, gadoversetamide, gadoxetic acid, gallium nitrate, ganirelix, gefitinib, gemcitabine, gemtuzumab, Glucarpidase, glutoxim, GM-CSF, goserelin, granisetron, granulocyte colony stimulating factor, histamine dihydrochloride, histrelin, hydroxycarbamide, I-125 seeds, lansoprazole, ibandronic acid, ibritumomab tiuxetan, ibrutinib, idarubicin, ifosfamide, imatinib, imiquimod, improsulfan, indisetron, incadronic acid, ingenol mebutate, interferon alfa, interferon beta, interferon gamma, iobitridol, iobenguane (123I), iomeprol, ipilimumab, irinotecan, Itraconazole, ixabepilone, ixazomib, lanreotide, lansoprazole, lapatinib, lasocholine, lenalidomide, lenvatinib, lenograstim, lentinan, letrozole, leuprorelin, levamisole, levonorgestrel, levothyroxine sodium, lisuride, lobaplatin, lomustine, lonidamine, masoprocol, medroxyprogesterone, megestrol, melarsoprol, melphalan, mepitiostane, mercaptopurine, mesna, methadone, methotrexate, methoxsalen, methylaminolevulinate, methylprednisolone, methyltestosterone, metirosine, mifamurtide, miltefosine, miriplatin, mitobronitol, mitoguazone, mitolactol, mitomycin, mitotane, mitoxantrone, mogamulizumab, molgramostim, mopidamol, morphine hydrochloride, morphine sulfate, nabilone, nabiximols, nafarelin, naloxone+pentazocine, naltrexone, nartograstim, necitumumab, nedaplatin, nelarabine, neridronic acid, netupitant/palonosetron, nivolumabpentetreotide, nilotinib, nilutamide, nimorazole, nimotuzumab, nimustine, nintedanib, nitracrine, nivolumab, obinutuzumab, octreotide, ofatumumab, olaparib, omacetaxine mepesuccinate, omeprazole, ondansetron, oprelvekin, orgotein, orilotimod, osimertinib, oxaliplatin, oxycodone, oxymetholone, ozogamicine, p53 gene therapy, paclitaxel, palbociclib, palifermin, palladium-103 seed, palonosetron, pamidronic acid, panitumumab, panobinostat, pantoprazole, pazopanib, pegaspargase, PEG-epoetin beta (methoxy PEG-epoetin beta), pembrolizumab, pegfilgrastim, peginterferon alfa-2b, pemetrexed, pentazocine, pentostatin, peplomycin, Perflubutane, perfosfamide, Pertuzumab, picibanil, pilocarpine, pirarubicin, pixantrone, plerixafor, plicamycin, poliglusam, polyestradiol phosphate, polyvinylpyrrolidone+sodium hyaluronate, polysaccharide-K, pomalidomide, ponatinib, porfimer sodium, pralatrexate, prednimustine, prednisone, procarbazine, procodazole, propranolol, quinagolide, rabeprazole, racotumomab, radium-223 chloride, radotinib, raloxifene, raltitrexed, ramosetron, ramucirumab, ranimustine, rasburicase, razoxane, refametinib, regorafenib, risedronic acid, rhenium-186 etidronate, rituximab, rolapitant, romidepsin, romiplostim, romurtide, roniciclib, samarium (153Sm) lexidronam, sargramostim, satumomab, secretin, siltuximab, sipuleucel-T, sizofiran, sobuzoxane, sodium glycididazole, sonidegib, sorafenib, stanozolol, streptozocin, sunitinib, talaporfin, talimogene laherparepvec, tamibarotene, tamoxifen, tapentadol, tasonermin, teceleukin, technetium (99mTc) nofetumomab merpentan, 99mTc-HYNIC-[Tyr3]-octreotide, tegafur, tegafur+gimeracil+oteracil, temoporfin, temozolomide, temsirolimus, teniposide, testosterone, tetrofosmin, thalidomide, thiotepa, thymalfasin, thyrotropin alfa, tioguanine, tocilizumab, topotecan, toremifene, tositumomab, trabectedin, trametinib, tramadol, trastuzumab, trastuzumab emtansine, treosulfan, tretinoin, trifluridine+tipiracil, trilostane, triptorelin, trametinib, trofosfamide, thrombopoietin, tryptophan, ubenimex, valatinib, valrubicin, vandetanib, vapreotide, vemurafenib, vinblastine, vincristine, vindesine, vinflunine, vinorelbine, vismodegib, vorinostat, vorozole, yttrium-90 glass microspheres, zinostatin, zinostatin stimalamer, zoledronic acid, zorubicin.

It has now been found, and this constitutes the basis of the present invention, that said compounds of the present invention have surprising and advantageous properties.

In particular, said compounds of the present invention have surprisingly been found to effectively inhibit Bub1 kinase and may therefore be used for the treatment or prophylaxis of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1 kinase, such as, for example, haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof.

The intermediates used for the synthesis of the compounds of the claims as described below, as well as their use for the synthesis of the compounds of claims described below, are one further aspect of the present invention. Preferred intermediates are the Intermediate Examples as disclosed below.

General Procedures

The compounds according to the invention can be prepared according to the following Schemes 1 through 7.

The Schemes and procedures described below illustrate synthetic routes to the compounds of general formula (I) of the invention and are not intended to be limiting. It is obvious to the person skilled in the art that the order of transformations as exemplified in the Schemes can be modified in various ways. The order of transformations exemplified in the Schemes is therefore not intended to be limiting. In addition, interconversion of any of the substituents, $R^3$, A, E and G can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wutts in *Protective Groups in Organic Synthesis*, $3^{rd}$ edition, Wiley 1999). Specific examples are described in the subsequent paragraphs.

Scheme 1

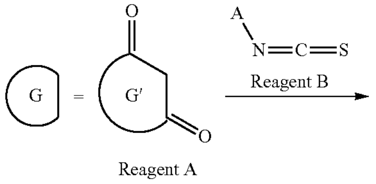

-continued

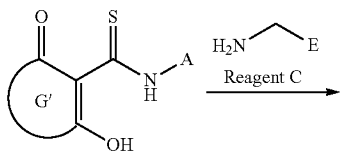

1-1

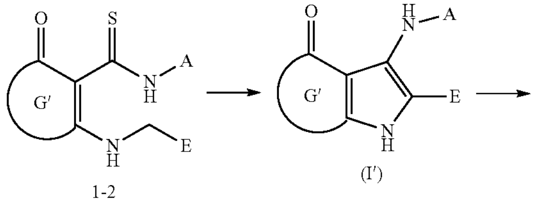

1-2

(I')

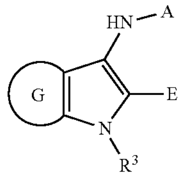

(I)

Scheme 1 Route for the preparation of compounds of general formula (I), wherein, $R^3$, A, E and G have the meaning as given for general formula (I), supra. In addition, interconversion of any of the substituents, $R^3$, A, E and G can be achieved before and/or after the exemplified transformations. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wutts in Protective Groups in Organic Synthesis, 3rd edition, Wiley 1999). Specific examples are described in the subsequent paragraphs. Reagent A, reagent B, and reagent C are either commercially available or can be prepared according to procedures available from the public domain, as understandable to the person skilled in the art. Specific examples are described in the subsequent paragraphs.

Scheme 2

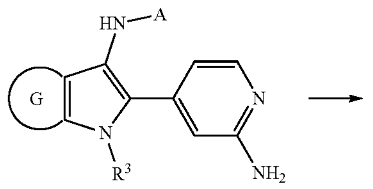

(II)

-continued

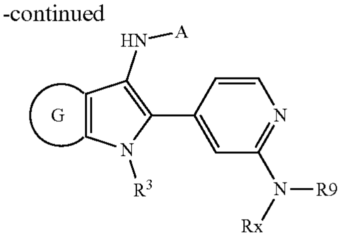

(III)

Scheme 2 Route for the preparation of compounds of general formula (III), wherein $R^x$ represents $R^{10}$—, C1-C4-alkyl, C3-C6-cycloalkyl, C1-C6 alkoxy, C1-C4-haloalkyl, $R^6$—C(O)—, $R^6$—O—C(O)—, $R^6$—SO2- or $R^7R^8N$—C(O)—, wherein and $R^3$, $R^6$, $R^7$, $R^8$, $R^9$, $R^{10}$, A, E and G have the meaning as given for general formula (I), supra. In addition, interconversion of any of the substituents $R^3$, A, E, G and $R^x$ can be achieved before and/or after the exemplified transformation. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wutts in Protective Groups in Organic Synthesis, 3rd edition, Wiley 1999). Specific examples are described in the subsequent paragraphs.

Intermediates of general formula (II) are reacted with an acylating reagent, a sulfonylating reagent or an acylating agent which can be generated in situ, to furnish Intermediates of general formula (III), these types of reactions are well-known to those skilled in the art (selected literature examples are: S. Miwatashi, et al., J. Med. Chem., 2005, 48, 5966-5979; J. Zhao, et al., Bioorg. Med. Chem. Lett., 2014, 24, 2802-2806; M. P. Hay, et al., J. Med. Chem., 2010, 53, 787-797; J. M. Keith, et al., Med. Chem. Lett, 2012, 3, 823-827; J. Liang, et al., Eur. J. Med. Chem., 2013, 67, 175-187; D. Lesuisse, et al., Bioorg. Med. Chem. Lett., 2011, 21, 2224-2228).

Not-limiting examples of these types of reagents can be:

i) carboxylic acid with dehydrating reagents typically used in amide bond formation, such as, for example (HBTU, HATU, PyBOP, BOP, T3P, EDC, DIC, DCC)
ii) acid fluorides, acid chlorides, acid bromides, preferably in the presence of a base
iii) acid anhydrides, preferably in the presence of a base
iv) chloroformates, preferably in the presence of a base
v) isocyanates, preferably in the presence of a base
vi) isothiocyanates, preferably in the presence of a base
vii) sulfonyl chlorides, preferably in the presence of a base
viii) sulfonyl anhydrides, preferably in the presence of a base It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

Scheme 3

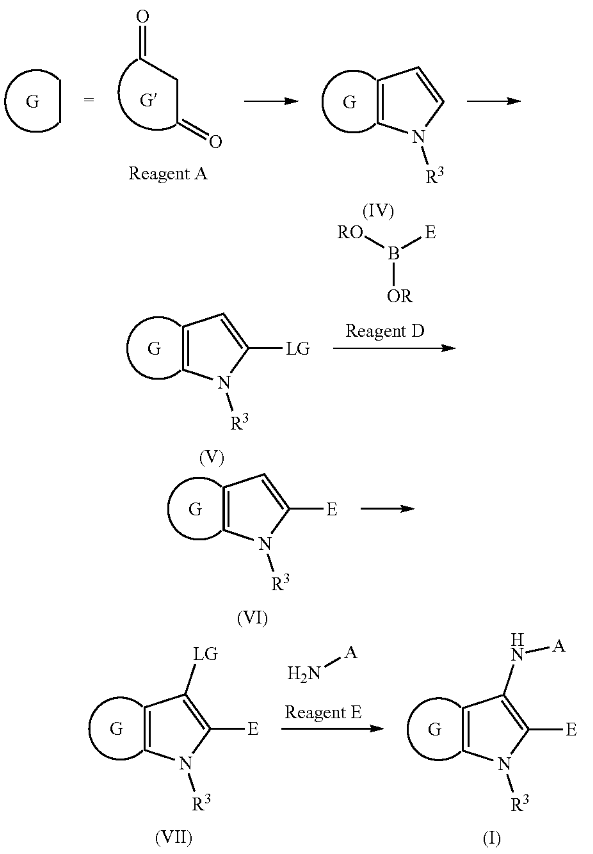

(IV)
(V)
(VI)
(VII)
(I)

Scheme 3 Route for the preparation of compounds of general formula (I), wherein $R^3$, A, E and G have the meaning as given for general formula (I), supra. In addition, interconversion of any of the substituents, $R^3$, A, E and G can be achieved before and/or after the exemplified transformation. The R in reagent D can be hydrogen to represent boronic acids or alkyl groups to represent boronic esters, optionally both R groups can be attached to each other to represent, for example, pincacol boronic esters. The substituent LG in the intermediates of general formulae V and VII can be a suitable leaving group, such as, for example, Cl, Br, I, aryl sulfonates such as for example p-toluene sulfonate, or alkyl sulfonates such as for example methane sulfonate or trifluoromethane sulfonate. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wutts in Protective Groups in Organic Synthesis, 3rd edition, Wiley 1999). Specific examples are described in the subsequent paragraphs.

Intermediates of general formula (IV) are commercially available or are reported in the public domain, see the teachings of, for example, Menichincheri et al., WO2014/72220 A1; Clark et al., J. Heterocyclic Chem., 1993, 30, 829-831; Clark et al., J. Med. Chem., 1993, 36, 2645-2657; Schneller et al., J. Med. Chem., 1978, 21, 990-993. Intermediates of general formula (IV) can be reacted to introduce a substituent Z, which is preferably a halide, such reactions are known to those skilled in the art (see Menichincheri et al., WO2014/72220 A1 (introduction of bromide and iodide); Smith et al., Bioorg. Med. Chem. Lett., 2007, 17, 673-678 (introduction of bromide) Cee et al., WO2014/22752 A1 (introduction of bromide)) to furnish intermediates of the formula (V). Intermediates of general formula V can be reacted to introduce the substituent E, such as, for example, an aryl or heteroaryl group using metal-catalyzed reactions, such as, for example, the Suzuki reaction. Such reactions are known to those skilled in the art (WO2007/39740 A2; Cee et al., WO2014/22752 A1; Smith et al., Bioorg. Med. Chem. Lett., 2007, 17, 673-678) and can be used to furnish intermediates of the formula VI. Intermediates of general formula (VI) can be reacted with a suitable halogenating reagent, such as, for example, copper(I) bromide and N-bromosuccinimide, preferably N-bromosuccinimide, in a suitable solvent system, such as, for example, acetonitrile, in a temperature range from 0° C. to the boiling point of the respective solvent, preferably the reaction is carried out at room temperature, to furnish general formula (VII). Similar examples for the bromination of pyrroles have been previously published using lactams (Aiello, E. et al., J. Heterocyclic Chem., 1982, 19, 977-979; Duranti, A. et al., Bioorg. Med. Chem., 2003, 11, 3965-3973).

Intermediates of general formula (VII) can be reacted with a suitable primary amines, such as, for example, primary aromatic amines and primary amines, preferably primary aromatic amines, such as, for example aniline or 3-aminothiophene, in the presence of a base, such as, for example, lithium bis(trimethylsilyl)amide (LHMDS), in the presence of a catalyst, such as, for example a suitable ligand, preferably 2-(di-tert-butylphosphino)-2',4',6'-triisopropyl-3,6-dimethoxy-1,1'-biphenyl (tBuBrettPhos) and in the presence of a pre-catalyst, such as, for example a palladium pre-catalyst, preferably chloro[2-(dicyclohexylphosphino)-3,6-dimethoxy-2',4',6'-triisopropyl-1,1'-biphenyl][2-(2-aminoethyl)phenyl]palladium(II) (BrettPhos-PreCat MTBE ether adduct) in a suitable solvent system, such as, for example, tetrahydrofuran (THF), in a temperature range from 0° C. to the 200° C., preferably the reaction is carried out at 80° C., to furnish compounds of general formula (I).

Scheme 4

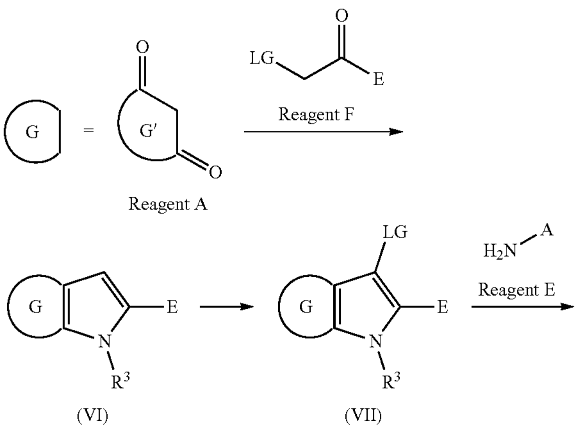

(VI)
(VII)

-continued

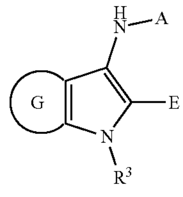

(I)

Scheme 4 Route for the preparation of compounds of general formula (IV), wherein $R^3$, A, E and G have the meaning as given for general formula (I), supra. In addition, interconversion of any of the substituents, $R^3$, A, E and G can be achieved before and/or after the exemplified transformation. The substituent LG in intermediates of general formula VII can be a suitable leaving group, such as, for example, Cl, Br, I, aryl sulfonates such as for example p-toluene sulfonate, or alkyl sulfonates such as for example methane sulfonate or trifluoromethane sulfonate. These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wuts in Protective Groups in Organic Synthesis, 3rd edition, Wiley 1999). Specific examples are described in the subsequent paragraphs.

Compounds reagent E and reagent F, are either commercially available or can be prepared according to procedures available from the public domain, as understandable to the person skilled in the art.

A suitably substituted 1,3-dicarbonyl compound (Reagent A) can be reacted with suitably substituted compounds of general formula (Reagent F) where LG is a suitable leaving group, such as, for example, bromide, chloride, which in the presence of an ammonium salt, such as, for example, ammonium acetate can furnish intermediates of general formula (VI). Similar examples for the formation of a pyrrole ring in this manner have been previously published using lactams (Anderson, D. R. et al., J. Med. Chem., 2007, 50, 2647-2654; Amici, R. et al., J. Med. Chem., 2008, 51, 487-501; Bargiotti, A. et al., J. Med. Chem., 2009, 52, 293-307; Voss et al., WO 2015/022073 A1).

Intermediates of general formula (VI) can be reacted with a suitable halogenating reagent, such as, for example, copper (I) bromide and N-bromosuccinimide, preferably N-bromosuccinimide, in a suitable solvent system, such as, for example, acetonitrile, in a temperature range from 0° C. to the boiling point of the respective solvent, preferably the reaction is carried out at room temperature, to furnish general formula (VII). Similar examples for the bromination of pyrroles have been previously published using lactams (Aiello, E. et al., J. Heterocyclic Chem., 1982, 19, 977-979; Duranti, A. et al., Bioorg. Med. Chem., 2003, 11, 3965-3973).

Intermediates of general formula (VII) can be reacted with a suitable primary amines, such as, for example, primary aromatic amines and primary amines, preferably primary aromatic amines, such as, for example aniline or 3-aminothiophene, in the presence of a base, such as, for example, lithium bis(trimethylsilyl)amide (LHMDS), in the presence of a catalyst, such as, for example a suitable ligand, preferably 2-(di-tert-butylphosphino)-2',4',6'-triisopropyl-3,6-dimethoxy-1,1'-biphenyl (tBuBrettPhos) and in the presence of a pre-catalyst, such as, for example a palladium pre-catalyst, preferably chloro[2-(dicyclohexylphosphino)-3,6-dimethoxy-2',4',6'-triisopropyl-1,1'-biphenyl][2-(2-aminoethyl)phenyl]palladium(II) (BrettPhos-PreCat MTBE ether adduct) in a suitable solvent system, such as, for example, tetrahydrofuran (THF), in a temperature range from 0° C. to the 200° C., preferably the reactio n is carried out at 80° C., to furnish compounds of general formula (I).

Scheme 5

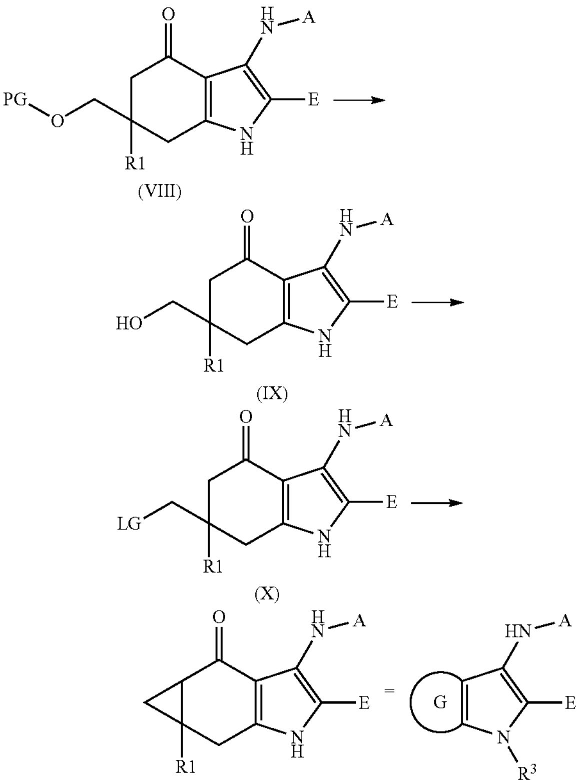

(VIII)
(IX)
(X)
(I)
(I)

Scheme 5 Route for the preparation of compounds of general formula (I), wherein $R^1$, $R^3$, A, E and G have the meaning as given for general formula (I), supra and LG is a leaving group, such as, for example, F, Cl, Br, I or aryl sulfonate such as for example p toluene sulfonate, or alkyl sulfonate such as for example methane sulfonate or trifluoromethane sulfonate. Intermediates of general formula (VIII) can be converted to intermediates of general formula (IX) using methods well-known to those skilled in the art. (see for example T. W. Greene and P. G. M. Wuts in Protective Groups in Organic Synthesis, 3rd edition, Wiley 1999).

Intermediates of general formula (IX) can be reacted with suitable reagents to generate a compounds of Formula (X) containing a leaving group (LG) and these methods are well known to those skilled in the art. The said leaving groups can be, Cl, Br, I, aryl sulfonates such as for example p-toluene sulfonate, or alkyl sulfonates. For these types of transformations see the teachings of Carro et al., Eur. J. Med. Chem., 2014, 71, 237-249; U.S. Pat. No. 5,739,351 A1, 1998; Pita et al., Tet. Lett., 2000, 41, 50, 9829-9833; Chenara et al., J. Org. Chem., 1992, 57, 2018-2029; Clark et al., WO2011/123674 A1, 2011. Intermediates of general formula (X) containing a leaving group (LG) can be reacted under various reaction conditions to generate compounds of Formula (I) and these methods are well known to those skilled in the art. The said leaving groups can be, Cl, Br, I, aryl sulfonates such as for example p-toluene sulfonate, or alkyl sulfonates. For these types of transformations see the teachings of Toda et al., Chem. Pharm. Bull., 1998, 46, 906-912; Tsuda et al., Chem. Pharm. Bull., 1996, 44, 515-524; Julia et al., Bull. Soc. Chim. Fr., 1960, 174-178; Clark et al., WO2011/123674 A1, 2011.

These modifications can be such as the introduction of protecting groups, cleavage of protecting groups, reduction or oxidation of functional groups, halogenation, metallation, substitution or other reactions known to the person skilled in the art. These transformations include those which introduce a functionality which allows for further interconversion of substituents. Appropriate protecting groups and their introduction and cleavage are well-known to the person skilled in the art (see for example T. W. Greene and P. G. M. Wutts in Protective Groups in Organic Synthesis, 3rd edition, Wiley 1999). Specific examples are described in the subsequent paragraphs.

Scheme 6

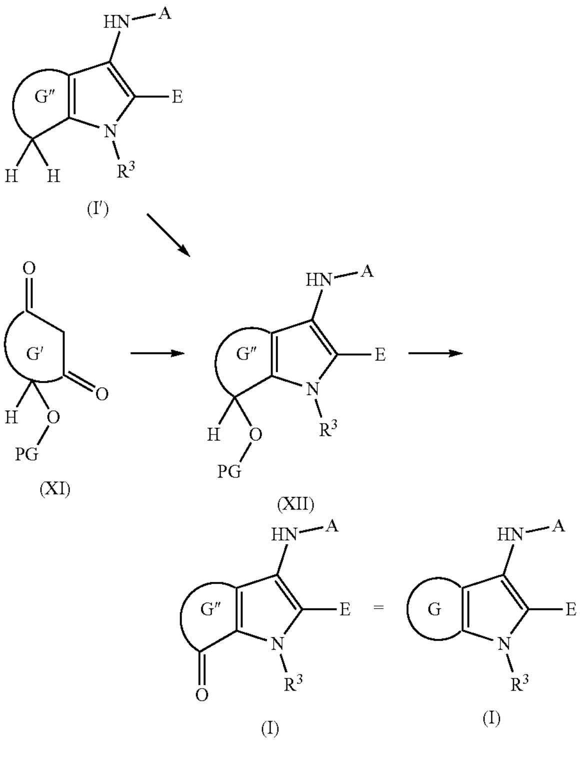

(I')

(XI)

(XII)

(I)

(I)

Scheme 6 Route for the preparation of compounds of general formula (I), wherein $R^3$, A, E and G have the meaning as given for general formula (I), supra. In addition, interconversion of any of the substituents, $R^3$, A, E and G can be achieved before and/or after the exemplified transformation.

Intermediates of general formula (XII) can be synthesized by intermediates of general Formula (XI) using the analogous methods as described previously in Schemes 1, 3 and 4. Intermediates of general formula (XII) can also be synthesized from compounds of Formula (I') via an oxidation step. Such oxidation methods are well known to those skilled in the art and can be carried using oxidating reagents, such as, for example, selenium dioxide, chromium(VI) reagents (e.g. Jones reagent, pyridinium dichromate, pyridinium chlorochromate), cerium reagents (e.g. ceric ammonium nitrate (CAN)), iodoxy reagents (e.g. Dess-Martin Periodinate, SIBX (see Zaimoku et al., Org. Lett., 2012, 14, 6088-6091)) or using transition-metal catalyzed oxidations or using radical oxidations, such as, for example, lead(IV) acetate (Lash et al., Tetrahedron, 1998, 54, 359-374), tert-butylhypochlorite (Jiang et al., RSC Advances, 2015, 5, 9204-9207) or by autoxidation in the presence of air or in the presence of oxygen (Moranta et al., Synthesis, 1999, 447-452).

Scheme 7

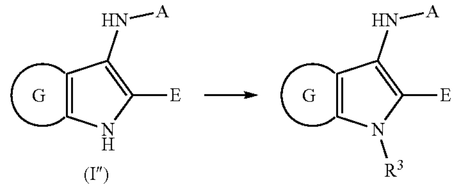

(I")

(I)

Scheme 7 Route for the preparation of compounds of general formula (I), wherein $R^3$, A, E and G have the meaning as given for general formula (I). Compounds of general formula (1") can be converted to compounds of general formula (I) by treatment with a suitable base, such as, for example, alkali metal carbonate, alkali metal hydrogen carbonate, alkali metal hydroxide, sodium hydride, alkali metal alkoxide, LHMDS, optionally in the presence of a phase transfer catalyst, or a crown ether, with an alkylating reagent which contains a suitable leaving group, such as, for example, F, Cl, Br, I or aryl sulfonate such as for example para-toluene sulfonate, or alkyl sulfonate such as for example methane sulfonate or trifluoromethane sulfonate, are commercially available or can be synthesized by those skilled in the art, in a suitable solvent, such as, for example, ethanol, methanol, water, DMF, tetrahydrofuran (THF), preferably, DMF, in a temperature range from −78° C. to the boiling point of the respective solvent, preferably the reaction is carried out RT to the boiling point of the respective solvent, to furnish general formula (I). Such transformations have been previously reported (Zhang et al., Bioorg. Med. Chem. Lett., 2006, 16, 3233-3237; WO2008/132434 A2, Kang et al., Bioorg. Med. Chem., 2010, 18, 6156-6169; Vanotti et al., J. Med. Chem., 2008, 51, 487-501).

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent.

Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids by formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of claims 1-5 according to the examples as well as the Intermediates used for their preparation.

Optionally, compounds of the formula (I) can be converted into their salts, or, optionally, salts of the compounds of the formula (I) can be converted into the free compounds. Corresponding processes are customary for the skilled person.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as chromatography on a suitable support material. Furthermore, reverse phase preparative HPLC of compounds of the present invention which possess a sufficiently basic or acidic functionality, may result in the formation of a salt, such as, in the case of a compound of the present invention which is sufficiently basic, a trifluoroacetate or formate salt for example, or, in the case of a compound of the present invention which is sufficiently acidic, an ammonium salt for example. Salts of this type can either be transformed into its free base or free acid form, respectively, by various methods known to the person skilled in the art, or be used as salts in subsequent biological assays. Additionally, the drying process during the isolation of compounds of the present invention may not fully remove traces of cosolvents, especially such as formic acid or trifluoroacetic acid, to give solvates or inclusion complexes. The person skilled in the art will recognise which solvates or inclusion complexes are acceptable to be used in subsequent biological assays. It is to be understood that the specific form (e.g. salt, free base, solvate, inclusion complex) of a compound of the present invention as isolated as described herein is not necessarily the only form in which said compound can be applied to a biological assay in order to quantify the specific biological activity.

Salts of the compounds according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art. Especially preferred are hydrochlorides and the process used in the example section.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids vl formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

One preferred aspect of the invention is the process for the preparation of the compounds of the claims 1 to 5, according to the examples, as well as the intermediates used for their preparation.

Optionally, compounds of formula (I) according to the invention can be converted into their salts, or, optionally, salts of the compounds according to the invention can be converted into the free compounds. Corresponding processes are customary for the skilled person.

Commercial Utility

As mentioned supra, the compounds of the present invention have surprisingly been found to effectively inhibit Bub1 finally resulting in cell death e.g. apoptosis and may therefore be used for the treatment or prophylaxis of diseases of uncontrolled cell growth, proliferation and/or survival, inappropriate cellular immune responses, or inappropriate cellular inflammatory responses, or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Bub1, such as, for example, benign and malignant neoplasia, more specifically haematological tumours, solid tumours, and/or metastases thereof, e.g. leukaemias and myelodysplastic syndrome, malignant lymphomas, head and neck tumours including brain tumours and brain metastases, tumours of the thorax including non-small cell and small cell lung tumours, gastrointestinal tumours, endocrine tumours, mammary and other gynaecological tumours, urological tumours including renal, bladder and prostate tumours, skin tumours, and sarcomas, and/or metastases thereof, especially haematological tumours, solid tumours, and/or metastases of breast, bladder, bone, brain, central and peripheral nervous system, cervix, colon, endocrine glands (e.g. thyroid and adrenal cortex), endocrine tumours, endometrium, esophagus, gastrointestinal tumours, germ cells, kidney, liver, lung, larynx and hypopharynx, mesothelioma, ovary, pancreas, prostate, rectum, renal, small intestine, soft tissue, stomach, skin, testis, ureter, vagina and vulva as well as malignant neoplasias including primary tumors in said organs and corresponding secondary tumors in distant organs ("tumor metastases"). Haematological tumors can e.g be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

A further aspect of the invention is the use of the compounds of formula (I) according to the invention for the treatment of cer-vical-, breast-, non-small cell lung-, prostate-, colon- and melanoma tumors and/or metastases thereof, especially preferred for the treatment thereof as well as a method of treatment of cervical-, breast-, non-small cell lung-, prostate-, colon- and melanoma tumors and/or metastases thereof comprising administering an effective amount of a compound according to the invention.

One aspect of the invention is the use of the compounds of formula (I) according to the invention for the treatment of cervix tumors as well as a method of treatment of cervix tumors comprising administering an effective amount of a compound according to the invention.

In accordance with an aspect of the present invention therefore the invention relates to a compound of formula (I) according to the invention, or an N-oxide, a salt, a tautomer or a stereoisomer of said compound, or a salt of said N-oxide, tautomer or stereoisomer particularly a pharmaceutically acceptable salt thereof, or a mixture of same, as described and defined herein, for use in the treatment or prophylaxis of a disease, especially for use in the treatment of a disease.

Another particular aspect of the present invention is therefore the use of a compound of formula (I) according to the invention, described supra, or a stereoisomer, a tautomer, an N-oxide, a hydrate, a solvate, or a salt thereof, particularly a pharmaceutically acceptable salt thereof, or a mixture of same, for the prophylaxis or treatment of hyperproliferative disorders or disorders responsive to induction of cell death i.e apoptosis.

The term "inappropriate" within the context of the present invention, in particular in the context of "inappropriate cellular immune responses, or inappropriate cellular inflammatory responses", as used herein, is to be understood as preferably meaning a response which is less than, or greater than normal, and which is associated with, responsible for, or results in, the pathology of said diseases.

Preferably, the use is in the treatment or prophylaxis of diseases, especially the treatment, wherein the diseases are haematological tumours, solid tumours and/or metastases thereof.

Another aspect is the use of a compound of formula (I) according to the invention for the treatment of cervical-, breast-, non-small cell lung-, prostate-, colon- and melanoma tumors and/or metastases thereof, especially preferred for the treatment thereof. A preferred aspect is the use of a compound of formula (I) according to the invention for the prophylaxis and/or treatment of cervical tumors especially preferred for the treatment thereof.

Another aspect of the present invention is the use of a compound according to the invention or a stereoisomer, a tautomer, an N-oxide, a hydrate, a solvate, or a salt thereof, particularly a pharmaceutically acceptable salt thereof, or a mixture of same, as described herein, in the manufacture of a medicament for the treatment or prophylaxis of a disease, wherein such disease is a hyperproliferative disorder or a disorder responsive to induction of cell death e.g. apoptosis. In an embodiment the disease is a haematological tumour, a solid tumour and/or metastases thereof. In another embodiment the disease is cervical-, breast-, non-small cell lung-, prostate-, colon- and melanoma tumor and/or metastases thereof, in a preferred aspect the disease is cervical tumor.

Method of Treating Hyper-proliferative Disorders

The present invention relates to a method for using the compounds of the present invention and compositions thereof, to treat mammalian hyper-proliferative disorders. Compounds can be utilized to inhibit, block, reduce, decrease, etc., cell proliferation and/or cell division, and/or produce cell death e.g. apoptosis. This method comprises administering to a mammal in need thereof, including a human, an amount of a compound of this invention, or a pharmaceutically acceptable salt, isomer, polymorph, metabolite, hydrate, solvate or ester thereof; etc. which is effective to treat the disorder. Hyper-proliferative disorders include but are not limited, e.g., psoriasis, keloids, and other hyperplasias affecting the skin, benign prostate hyperplasia (BPH), solid tumours, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukaemias.

Examples of breast cancer include, but are not limited to invasive ductal carcinoma, invasive lobular carcinoma, ductal carcinoma in situ, and lobular carcinoma in situ.

Examples of cancers of the respiratory tract include, but are not limited to small-cell and non-small-cell lung carcinoma, as well as bronchial adenoma and pleuropulmonary blastoma.

Examples of brain cancers include, but are not limited to brain stem and hypothalamic glioma, cerebellar and cerebral astrocytoma, medulloblastoma, ependymoma, as well as neuroectodermal and pineal tumour.

Tumours of the male reproductive organs include, but are not limited to prostate and testicular cancer. Tumours of the female reproductive organs include, but are not limited to endometrial, cervical, ovarian, vaginal, and vulvar cancer, as well as sarcoma of the uterus.

Tumours of the digestive tract include, but are not limited to anal, colon, colorectal, oesophageal, gallbladder, gastric, pancreatic, rectal, small-intestine, and salivary gland cancers.

Tumours of the urinary tract include, but are not limited to bladder, penile, kidney, renal pelvis, ureter, urethral and human papillary renal cancers.

Eye cancers include, but are not limited to intraocular melanoma and retinoblastoma.

Examples of liver cancers include, but are not limited to hepatocellular carcinoma (liver cell carcinomas with or without fibrolamellar variant), cholangiocarcinoma (intrahepatic bile duct carcinoma), and mixed hepatocellular cholangiocarcinoma.

Skin cancers include, but are not limited to squamous cell carcinoma, Kaposi's sarcoma, malignant melanoma, Merkel cell skin cancer, and non-melanoma skin cancer.

Head-and-neck cancers include, but are not limited to laryngeal, hypopharyngeal, nasopharyngeal, oropharyngeal cancer, lip and oral cavity cancer and squamous cell. Lymphomas include, but are not limited to AIDS-related lymphoma, non-Hodgkin's lymphoma, cutaneous T-cell lymphoma, Burkitt lymphoma, Hodgkin's disease, and lymphoma of the central nervous system.

Sarcomas include, but are not limited to sarcoma of the soft tissue, osteosarcoma, malignant fibrous histiocytoma, lymphosarcoma, and rhabdomyosarcoma.

Leukemias include, but are not limited to acute myeloid leukemia, acute lymphoblastic leukemia, chronic lymphocytic leukemia, chronic myelogenous leukemia, and hairy cell leukemia.

These disorders have been well characterized in humans, but also exist with a similar etiology in other mammals, and can be treated by administering pharmaceutical compositions of the present invention.

The term "treating" or "treatment" as stated throughout this document is used conventionally, e.g., the management or care of a subject for the purpose of combating, alleviating, reducing, relieving, improving the condition of, etc., of a disease or disorder, such as a carcinoma.

Methods of Treating Kinase Disorders

The present invention also provides methods for the treatment of disorders associated with aberrant mitogen extracellular kinase activity, including, but not limited to stroke, heart failure, hepatomegaly, cardiomegaly, diabetes, Alzheimer's disease, cystic fibrosis, symptoms of xenograft rejections, septic shock or asthma.

Effective amounts of compounds of the present invention can be used to treat such disorders, including those diseases (e.g., cancer) mentioned in the Background section above. Nonetheless, such cancers and other diseases can be treated with compounds of the present invention, regardless of the mechanism of action and/or the relationship between the kinase and the disorder.

The phrase "aberrant kinase activity" or "aberrant tyrosine kinase activity," includes any abnormal expression or activity of the gene encoding the kinase or of the polypeptide it encodes. Examples of such aberrant activity, include, but are not limited to, over-expression of the gene or polypeptide; gene amplification; mutations which produce constitutively-active or hyperactive kinase activity; gene mutations, deletions, substitutions, additions, etc.

The present invention also provides for methods of inhibiting a kinase activity, especially of mitogen extracellular kinase, comprising administering an effective amount of a compound of the present invention, including salts, polymorphs, metabolites, hydrates, solvates, prodrugs (e.g.: esters) thereof, and diastereoisomeric forms thereof. Kinase activity can be inhibited in cells (e.g., in vitro), or in the cells of a mammalian subject, especially a human patient in need of treatment.

Methods of Treating Angiogenic Disorders

The present invention also provides methods of treating disorders and diseases associated with excessive and/or abnormal angiogenesis.

Inappropriate and ectopic expression of angiogenesis can be deleterious to an organism. A number of pathological conditions are associated with the growth of extraneous blood vessels. These include, e.g., diabetic retinopathy, ischemic retinal-vein occlusion, and retinopathy of prematurity [Aiello et al. New Engl. J. Med. 1994, 331, 1480; Peer et al. Lab. Invest. 1995, 72, 638], age-related macular degeneration [AMD; see, Lopez et al. Invest. Opththalmol. Vis. Sci. 1996, 37, 855], neovascular glaucoma, psoriasis, retrolental fibroplasias, angiofibroma, inflammation, rheumatoid arthritis (RA), restenosis, in-stent restenosis, vascular graft restenosis, etc. In addition, the increased blood supply associated with cancerous and neoplastic tissue, encourages growth, leading to rapid tumour enlargement and metastasis. Moreover, the growth of new blood and lymph vessels in a tumour provides an escape route for renegade cells, encouraging metastasis and the consequence spread of the cancer. Thus, compounds of the present invention can be utilized to treat and/or prevent any of the aforementioned angiogenesis disorders, e.g., by inhibiting and/or reducing blood vessel formation; by inhibiting, blocking, reducing, decreasing, etc. endothelial cell proliferation or other types involved in angiogenesis, as well as causing cell death e.g. apoptosis of such cell types.

Preferably, the diseases of said method are haematological tumours, solid tumour and/or metastases thereof.

The compounds of the present invention can be used in particular in therapy and prevention i.e. prophylaxis, especially in therapy of tumour growth and metastases, especially in solid tumours of all indications and stages with or without pre-treatment of the tumour growth.

Pharmaceutical Compositions of the Compounds of the Invention

This invention also relates to pharmaceutical compositions containing one or more compounds of the present invention. These compositions can be utilised to achieve the desired pharmacological effect by administration to a patient in need thereof. A patient, for the purpose of this invention, is a mammal, including a human, in need of treatment for the particular condition or disease.

Therefore, the present invention includes pharmaceutical compositions that are comprised of a pharmaceutically acceptable carrier or auxiliary and a pharmaceutically effective amount of a compound, or salt thereof, of the present invention.

Another aspect of the invention is a pharmaceutical composition comprising a pharmaceutically effective amount of a compound of formula (I) according to the invention and a pharmaceutically acceptable auxiliary for the treatment of a disease mentioned supra, especially for the treatment of haematological tumours, solid tumours and/or metastases thereof.

A pharmaceutically acceptable carrier or auxiliary is preferably a carrier that is non-toxic and innocuous to a patient at concentrations consistent with effective activity of the active ingredient so that any side effects ascribable to the carrier do not vitiate the beneficial effects of the active ingredient. Carriers and auxiliaries are all kinds of additives assisting to the composition to be suitable for administration.

A pharmaceutically effective amount of compound is preferably that amount which produces a result or exerts the intended influence on the particular condition being treated.

The compounds of the present invention can be administered with pharmaceutically-acceptable carriers or auxiliaries well known in the art using any effective conventional dosage unit forms, including immediate, slow and timed release preparations, orally, parenterally, topically, nasally, ophthalmically, optically, sublingually, rectally, vaginally, and the like.

For oral administration, the compounds can be formulated into solid or liquid preparations such as capsules, pills, tablets, troches, lozenges, melts, powders, solutions, suspensions, or emulsions, and may be prepared according to methods known to the art for the manufacture of pharmaceutical compositions. The solid unit dosage forms can be a capsule that can be of the ordinary hard- or soft-shelled gelatine type containing auxiliaries, for example, surfactants, lubricants, and inert fillers such as lactose, sucrose, calcium phosphate, and corn starch.

In another embodiment, the compounds of this invention may be tableted with conventional tablet bases such as lactose, sucrose and cornstarch in combination with binders such as acacia, corn starch or gelatine, disintegrating agents intended to assist the break-up and dissolution of the tablet following administration such as potato starch, alginic acid, corn starch, and guar gum, gum tragacanth, acacia, lubricants intended to improve the flow of tablet granulation and to prevent the adhesion of tablet material to the surfaces of the tablet dies and punches, for example talc, stearic acid, or magnesium, calcium or zinc stearate, dyes, colouring agents, and flavouring agents such as peppermint, oil of wintergreen, or cherry flavouring, intended to enhance the aesthetic qualities of the tablets and make them more acceptable to the patient. Suitable excipients for use in oral liquid dosage forms include dicalcium phosphate and diluents such as water and alcohols, for example, ethanol, benzyl alcohol, and polyethylene alcohols, either with or without the addition of a pharmaceutically acceptable surfactant, suspending agent or emulsifying agent. Various other materials may be present as coatings or to otherwise modify the physical form of the dosage unit. For instance tablets, pills or capsules may be coated with shellac, sugar or both.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example those sweetening, flavouring and colouring agents described above, may also be present.

The pharmaceutical compositions of this invention may also be in the form of oil-in-water emulsions. The oily phase may be a vegetable oil such as liquid paraffin or a mixture of vegetable oils. Suitable emulsifying agents may be (1) naturally occurring gums such as gum acacia and gum tragacanth, (2) naturally occurring phosphatides such as soy bean and lecithin, (3) esters or partial esters derived form fatty acids and hexitol anhydrides, for example, sorbitan monooleate, (4) condensation products of said partial esters with ethylene oxide, for example, polyoxyethylene sorbitan monooleate. The emulsions may also contain sweetening and flavouring agents.

Oily suspensions may be formulated by suspending the active ingredient in a vegetable oil such as, for example, arachis oil, olive oil, sesame oil or coconut oil, or in a mineral oil such as liquid paraffin. The oily suspensions may contain a thickening agent such as, for example, beeswax, hard paraffin, or cetyl alcohol. The suspensions may also contain one or more preservatives, for example, ethyl or n-propyl p-hydroxybenzoate; one or more colouring agents; one or more flavouring agents; and one or more sweetening agents such as sucrose or saccharin.

Syrups and elixirs may be formulated with sweetening agents such as, for example, glycerol, propylene glycol, sorbitol or sucrose. Such formulations may also contain a demulcent, and preservative, such as methyl and propyl parabens and flavouring and colouring agents.

The compounds of this invention may also be administered parenterally, that is, subcutaneously, intravenously, intraocularly, intrasynovially, intramuscularly, or interperitoneally, as injectable dosages of the compound in preferably a physiologically acceptable diluent with a pharmaceutical carrier which can be a sterile liquid or mixture of liquids such as water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,1-dioxolane-4-methanol, ethers such as poly(ethylene glycol) 400, an oil, a fatty acid, a fatty acid ester or, a fatty acid glyceride, or an acetylated fatty acid glyceride, with or without the addition of a pharmaceutically acceptable surfactant such as a soap or a detergent, suspending agent such as pectin, carbomers, methycellulose, hydroxypropylmethylcellulose, or carboxymethylcellulose, or emulsifying agent and other pharmaceutical adjuvants.

Illustrative of oils which can be used in the parenteral formulations of this invention are those of petroleum, animal, vegetable, or synthetic origin, for example, peanut oil, soybean oil, sesame oil, cottonseed oil, corn oil, olive oil, petrolatum and mineral oil. Suitable fatty acids include oleic acid, stearic acid, isostearic acid and myristic acid. Suitable fatty acid esters are, for example, ethyl oleate and isopropyl myristate. Suitable soaps include fatty acid alkali metal, ammonium, and triethanolamine salts and suitable detergents include cationic detergents, for example dimethyl dialkyl ammonium halides, alkyl pyridinium halides, and alkylamine acetates; anionic detergents, for example, alkyl, aryl, and olefin sulfonates, alkyl, olefin, ether, and monoglyceride sulfates, and sulfosuccinates; non-ionic detergents, for example, fatty amine oxides, fatty acid alkanolamides, and poly(oxyethylene-oxypropylene)s or ethylene oxide or propylene oxide copolymers; and amphoteric detergents, for example, alkyl-beta-aminopropionates, and 2-alkylimidazoline quaternary ammonium salts, as well as mixtures.

The parenteral compositions of this invention will typically contain from about 0.5% to about 25% by weight of the active ingredient in solution. Preservatives and buffers may also be used advantageously. In order to minimise or eliminate irritation at the site of injection, such compositions may contain a non-ionic surfactant having a hydrophile-lipophile balance (HLB) preferably of from about 12 to about 17. The quantity of surfactant in such formulation preferably ranges from about 5% to about 15% by weight. The surfactant can be a single component having the above HLB or can be a mixture of two or more components having the desired HLB.

Illustrative of surfactants used in parenteral formulations are the class of polyethylene sorbitan fatty acid esters, for example, sorbitan monooleate and the high molecular weight adducts of ethylene oxide with a hydrophobic base, formed by the condensation of propylene oxide with propylene glycol.

The pharmaceutical compositions may be in the form of sterile injectable aqueous suspensions. Such suspensions may be formulated according to known methods using suitable dispersing or wetting agents and suspending agents such as, for example, sodium carboxymethylcellulose, methylcellulose, hydroxypropylmethyl-cellulose, sodium alginate, polyvinylpyrrolidone, gum tragacanth and gum acacia; dispersing or wetting agents which may be a naturally occurring phosphatide such as lecithin, a condensation product of an alkylene oxide with a fatty acid, for example, polyoxyethylene stearate, a condensation product of ethylene oxide with a long chain aliphatic alcohol, for example, heptadeca-ethyleneoxycetanol, a condensation product of ethylene oxide with a partial ester derived form a fatty acid and a hexitol such as polyoxyethylene sorbitol monooleate, or a condensation product of an ethylene oxide with a partial ester derived from a fatty acid and a hexitol anhydride, for example polyoxyethylene sorbitan monooleate.

The sterile injectable preparation may also be a sterile injectable solution or suspension in a non-toxic parenterally acceptable diluent or solvent. Diluents and solvents that may be employed are, for example, water, Ringer's solution, isotonic sodium chloride solutions and isotonic glucose solutions. In addition, sterile fixed oils are conventionally employed as solvents or suspending media. For this purpose, any bland, fixed oil may be employed including synthetic mono- or diglycerides. In addition, fatty acids such as oleic acid can be used in the preparation of injectables.

A composition of the invention may also be administered in the form of suppositories for rectal administration of the drug. These compositions can be prepared by mixing the drug with a suitable non-irritation excipient which is solid at ordinary temperatures but liquid at the rectal temperature and will therefore melt in the rectum to release the drug. Such materials are, for example, cocoa butter and polyethylene glycol.

Controlled release formulations for parenteral administration include liposomal, polymeric microsphere and polymeric gel formulations that are known in the art.

It may be desirable or necessary to introduce the pharmaceutical composition to the patient via a mechanical delivery device. The construction and use of mechanical delivery devices for the delivery of pharmaceutical agents is well known in the art. Direct techniques for administration, for example, administering a drug directly to the brain usually involve placement of a drug delivery catheter into the patient's ventricular system to bypass the blood-brain barrier. One such implantable delivery system, used for the transport of agents to specific anatomical regions of the body, is described in U.S. Pat. No. 5,011,472, issued Apr. 30, 1991.

The compositions of the invention can also contain other conventional pharmaceutically acceptable compounding ingredients, generally referred to as carriers or diluents, as necessary or desired. Conventional procedures for preparing such compositions in appropriate dosage forms can be utilized.

Such ingredients and procedures include those described in the following references, each of which is incorporated herein by reference: Powell, M. F. et al., "Compendium of Excipients for Parenteral Formulations" PDA Journal of Pharmaceutical Science & Technology 1998, 52(5), 238-311; Strickley, R. G "Parenteral Formulations of Small Molecule Therapeutics Marketed in the United States (1999)-Part-1" PDA Journal of Pharmaceutical Science & Technology 1999, 53(6), 324-349; and Nema, S. et al., "Excipients and Their Use in Injectable Products" PDA Journal of Pharmaceutical Science & Technology 1997, 51(4), 166-171.

Commonly used pharmaceutical ingredients that can be used as appropriate to formulate the composition for its intended route of administration include:

acidifying agents (examples include but are not limited to acetic acid, citric acid, fumaric acid, hydrochloric acid, nitric acid);

alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine);

adsorbents (examples include but are not limited to powdered cellulose and activated charcoal;

aerosol propellants (examples include but are not limited to carbon dioxide, $CCl_2F_2$, $F_2ClC—CClF_2$ and $CClF_3$)

air displacement agents—examples include but are not limited to nitrogen and argon; antifungal preservatives (examples include but are not limited to benzoic acid, butylparaben, ethylparaben, methylparaben, propylparaben, sodium benzoate);

antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal);

antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite);

binding materials (examples include but are not limited to block polymers, natural and synthetic rubber, polyacrylates, polyurethanes, silicones, polysiloxanes and styrene-butadiene copolymers);

buffering agents (examples include but are not limited to potassium metaphosphate, dipotassium phosphate, sodium acetate, sodium citrate anhydrous and sodium citrate dihydrate);

carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection);

chelating agents (examples include but are not limited to edetate disodium and edetic acid);

colourants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel and ferric oxide red);

clarifying agents (examples include but are not limited to bentonite);

emulsifying agents (examples include but are not limited to acacia, cetomacrogol, cetyl alcohol, glyceryl monostearate, lecithin, sorbitan monooleate, polyoxyethylene 50 monostearate);

encapsulating agents (examples include but are not limited to gelatin and cellulose acetate phthalate), flavourants (examples include but are not limited to anise oil, cinnamon oil, cocoa, menthol, orange oil, peppermint oil and vanillin);

humectants (examples include but are not limited to glycerol, propylene glycol and sorbitol);

levigating agents (examples include but are not limited to mineral oil and glycerin); oils (examples include but are not limited to arachis oil, mineral oil, olive oil, peanut oil, sesame oil and vegetable oil);

ointment bases (examples include but are not limited to lanolin, hydrophilic ointment, polyethylene glycol ointment, petrolatum, hydrophilic petrolatum, white ointment, yellow ointment, and rose water ointment);

penetration enhancers (transdermal delivery) (examples include but are not limited to monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas), plasticizers (examples include but are not limited to diethyl phthalate and glycerol);

solvents (examples include but are not limited to ethanol, corn oil, cottonseed oil, glycerol, isopropanol, mineral oil, oleic acid, peanut oil, purified water, water for injection, sterile water for injection and sterile water for irrigation);

stiffening agents (examples include but are not limited to cetyl alcohol, cetyl esters wax, microcrystalline wax, paraffin, stearyl alcohol, white wax and yellow wax);

suppository bases (examples include but are not limited to cocoa butter and polyethylene glycols (mixtures));

surfactants (examples include but are not limited to benzalkonium chloride, nonoxynol 10, oxtoxynol 9, polysorbate 80, sodium lauryl sulfate and sorbitan mono-palmitate);

suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum);

sweetening agents (examples include but are not limited to aspartame, dextrose, glycerol, mannitol, propylene glycol, saccharin sodium, sorbitol and sucrose);

tablet anti-adherents (examples include but are not limited to magnesium stearate and talc);

tablet binders (examples include but are not limited to acacia, alginic acid, carboxymethylcellulose sodium, compressible sugar, ethylcellulose, gelatin, liquid glucose, methylcellulose, non-crosslinked polyvinyl pyrrolidone, and pregelatinized starch);

tablet and capsule diluents (examples include but are not limited to dibasic calcium phosphate, kaolin, lactose, mannitol, microcrystalline cellulose, powdered cellulose, precipitated calcium carbonate, sodium carbonate, sodium phosphate, sorbitol and starch);

tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac);

tablet direct compression excipients (examples include but are not limited to dibasic calcium phosphate);

tablet disintegrants (examples include but are not limited to alginic acid, carboxymethylcellulose calcium, microcrystalline cellulose, polacrillin potassium, crosslinked polyvinylpyrrolidone, sodium alginate, sodium starch glycollate and starch);

tablet glidants (examples include but are not limited to colloidal silica, corn starch and talc);

tablet lubricants (examples include but are not limited to calcium stearate, magnesium stearate, mineral oil, stearic acid and zinc stearate);

tablet/capsule opaquants (examples include but are not limited to titanium dioxide); tablet polishing agents (examples include but are not limited to carnuba wax and white wax);

thickening agents (examples include but are not limited to beeswax, cetyl alcohol and paraffin);

tonicity agents (examples include but are not limited to dextrose and sodium chloride);

viscosity increasing agents (examples include but are not limited to alginic acid, bentonite, carbomers, carboxymethylcellulose sodium, methylcellulose, polyvinyl pyrrolidone, sodium alginate and tragacanth); and wetting agents (examples include but are not limited to heptadecaethylene oxycetanol, lecithins, sorbitol monooleate, polyoxyethylene sorbitol monooleate, and polyoxyethylene stearate).

Pharmaceutical compositions according to the present invention can be illustrated as follows:

Sterile i.v. solution: A 5 mg/mL solution of the desired compound of this invention can be made using sterile, injectable water, and the pH is adjusted if necessary. The solution is diluted for administration to 1-2 mg/mL with sterile 5% dextrose and is administered as an i.v. infusion over about 60 minutes.

Lyophilised powder for i.v. administration: A sterile preparation can be prepared with (i) 100-1000 mg of the desired compound of this invention as a lyophilised powder, (ii) 32-327 mg/mL sodium citrate, and (iii) 300-3000 mg Dextran 40. The formulation is reconstituted with sterile, injectable saline or dextrose 5% to a concentration of 10 to 20 mg/mL, which is further diluted with saline or dextrose 5% to 0.2-0.4 mg/mL, and is administered either IV bolus or by IV infusion over 15-60 minutes.

Intramuscular suspension: The following solution or suspension can be prepared, for intramuscular injection:

50 mg/mL of the desired, water-insoluble compound of this invention 5 mg/mL sodium carboxymethylcellulose 4 mg/mL TWEEN 80

9 mg/mL sodium chloride 9 mg/mL benzyl alcohol

Hard Shell Capsules: A large number of unit capsules are prepared by filling standard two-piece hard galantine capsules each with 100 mg of powdered active ingredient, 150 mg of lactose, 50 mg of cellulose and 6 mg of magnesium stearate.

Soft Gelatin Capsules: A mixture of active ingredient in a digestible oil such as soybean oil, cottonseed oil or olive oil is prepared and injected by means of a positive displacement pump into molten gelatin to form soft gelatin capsules containing 100 mg of the active ingredient. The capsules are washed and dried. The active ingredient can be dissolved in a mixture of polyethylene glycol, glycerin and sorbitol to prepare a water miscible medicine mix.

Tablets: A large number of tablets are prepared by conventional procedures so that the dosage unit is 100 mg of active ingredient, 0.2 mg. of colloidal silicon dioxide, 5 mg of magnesium stearate, 275 mg of microcrystalline cellulose, 11 mg. of starch, and 98.8 mg of lactose. Appropriate aqueous and non-aqueous coatings may be applied to increase palatability, improve elegance and stability or delay absorption.

Immediate Release Tablets/Capsules: These are solid oral dosage forms made by conventional and novel processes. These units are taken orally without water for immediate dissolution and delivery of the medication. The active ingredient is mixed in a liquid containing ingredient such as sugar, gelatin, pectin and sweeteners. These liquids are solidified into solid tablets or caplets by freeze drying and solid state extraction techniques. The drug compounds may be compressed with viscoelastic and thermoelastic sugars and polymers or effervescent components to produce porous matrices intended for immediate release, without the need of water.

Dose and Administration

Based upon standard laboratory techniques known to evaluate compounds useful for the treatment of hyper-proliferative disorders and angiogenic disorders, by standard toxicity tests and by standard pharmacological assays for the determination of treatment of the conditions identified above in mammals, and by comparison of these results with the results of known medicaments that are used to treat these conditions, the effective dosage of the compounds of this invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, "drug holidays" in which a patient is not dosed with a drug for a certain period of time, may be beneficial to the overall balance between pharmacological effect and tolerability. A unit dosage may contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. The average daily rectal dosage regimen will preferably be from 0.01 to 200 mg/kg of total body weight. The average daily vaginal dosage regimen will preferably be from 0.01 to 200 mg/kg of total body weight. The average daily topical dosage regimen will preferably be from 0.1 to 200 mg administered between one to four times daily. The transdermal concentration will preferably be that required to maintain a daily dose of from 0.01 to 200 mg/kg. The average daily inhalation dosage regimen will preferably be from 0.01 to 100 mg/kg of total body weight.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

Combination Therapies

The compounds of this invention can be administered as the sole pharmaceutical agent or in combination with one or more other pharmaceutical agents where the combination causes no unacceptable adverse effects. Those combined pharmaceutical agents can be other agents having antiproliferative effects such as for example for the treatment of haematological tumours, solid tumours and/or metastases thereof and/or agents for the treatment of undesired side effects. The present invention relates also to such combinations.

Other anti-hyper-proliferative agents suitable for use with the composition of the invention include but are not limited to those compounds acknowledged to be used in the treatment of neoplastic diseases in Goodman and Gilman's The Pharmacological Basis of Therapeutics (Ninth Edition), editor Molinoff et al., publ. by McGraw-Hill, pages 1225-1287, (1996), which is hereby incorporated by reference, especially (chemotherapeutic) anti-cancer agents as defined supra. The combination can be a non-fixed combination or a fixed-dose combination as the case may be.

Methods of testing for a particular pharmacological or pharmaceutical property are well known to persons skilled in the art.

The example testing experiments described herein serve to illustrate the present invention and the invention is not limited to the examples given.

As will be appreciated by persons skilled in the art, the invention is not limited to the particular embodiments described herein, but covers all modifications of said embodiments that are within the spirit and scope of the invention as defined by the appended claims.

The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) according to the invention as disclosed by the specific examples.

The term “according to” within the experimental section is used in the sense that the procedure referred to is to be used “analogously to”.

Experimental Part

The following table lists the abbreviations used in this paragraph and in the Intermediate Examples and Examples section as far as they are not explained within the text body.

| Abbreviation | Meaning |
|---|---|
| AcOH | acetic acid (ethanoic acid) |
| ACN | acetonitrile |
| aq. | aqueous |
| Boc | t-butoxycarbonyl |
| br | broad |
| Cl | chemical ionisation |
| d | doublet |
| DAD | diode array detector |
| DBU | 1,8-Diazabicyclo(5.4.0)undec-7-ene |
| DCM | dichloromethane |
| dd | double-doublet |
| DIAD | diisopropyl (E)-diazene-1,2-dicarboxylate |
| DIPEA | N-ethyl-N-isopropylpropan-2-amine |
| DMA | Dimethylacetamide |
| DMF | N,N-dimethylformamide |
| DMSO | dimethyl sulfoxide |
| DPPA | diphenyl phosphorazidate |
| dt | Double-triplet |
| ELSD | Evaporative Light Scattering Detector |
| $Et_3N$ | N,N-diethylethanamine |
| EtOAc | ethyl acetate |
| EtOH | ethanol |
| eq. | equivalent |
| ESI | electrospray (ES) ionisation |
| h | hour |
| HATU | 1-[Bis(dimethylamino)methylene]-1H-1,2,3-triazolo[4,5-b]pyridinium 3-oxid hexafluorophosphate |
| HCl | Hydrochloric acid |
| HPLC | high performance liquid chromatography |
| $KO^tBu$ | Potassium tert-butoxide |
| LC-MS | liquid chromatography mass spectrometry |
| m | multiplet |
| mCPBA | meta-chloroperbenzoic acid |
| min | minute |
| MeCN | acetonitrile |
| MeOH | methanol |
| MS | mass spectrometry |
| NaCl | Sodium chloride |
| $NaHCO_3$ | Sodium hydrogen carbonate or sodium bicarbonate |
| NMR | nuclear magnetic resonance spectroscopy: chemical shifts ( ) are given in ppm. The chemical shifts were corrected by setting the DMSO signal to 2.50 ppm using unless otherwise stated. |
| PDA | Photo Diode Array |
| Pd/C | Palladium on activated charcoal |
| q | quartet |
| r.t. or rt or RT | room temperature, typically in a range from 18° C. to 23° C. |

-continued

| Abbreviation | Meaning |
|---|---|
| Rt | retention time (as measured either with HPLC or UPLC) in minutes |
| s | singlet |
| SIBX | Stabilized 2-iodoxybenzoic acid |
| SM | starting material |
| SQD | Single-Quadrupole-Detector |
| t | triplet |
| T3P | 2,4,6-tripropyl-1,3,5,2,4,6-trioxatriphosphinane 2,4,6-trioxide |
| TBAF | N,N,N-tributylbutan-1-aminium fluoride |
| td | Triple-doublet |
| TEA | triethylamine |
| TFA | trifluoroacetic acid |
| THF | tetrahydrofuran |
| UPLC | ultra performance liquid chromatography |

Other abbreviations have their meanings customary per se to the skilled person.

The various aspects of the invention described in this application are illustrated by the following examples which are not meant to limit the invention in any way.

Specific Experimental Descriptions

NMR peak forms in the following specific experimental descriptions are stated as they appear in the spectra, possible higher order effects have not been considered. Reactions employing microwave irradiation may be run with a Biotage Initator® microwave oven optionally equipped with a robotic unit. The reported reaction times employing microwave heating are intended to be understood as fixed reaction times after reaching the indicated reaction temperature. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example pre-packed silica gel cartridges, e.g. from Separtis such as Isolute® Flash silica gel or Isolute® Flash $NH_2$ silica gel in combination with a Isolera® autopurifier (Biotage) and eluents such as gradients of e.g. hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia. In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc) of a compound of the present invention as isolated as described herein is not necessarily the only form in which said compound can be applied to a biological assay in order to quantify the specific biological activity.

The percentage yields reported in the following examples are based on the starting component that was used in the lowest molar amount. Air and moisture sensitive liquids and solutions were transferred via syringe or cannula and introduced into reaction vessels through rubber septa. Commercial grade reagents and solvents were used without further purification. The term "concentrated in vacuo" refers to use of a Buchi rotary evaporator at a minimum pressure of approximately 15 mm of Hg. All temperatures are reported uncorrected in degrees Celsius (° C.).

In order that this invention may be better understood, the following examples are set forth. These examples are for the purpose of illustration only and are not to be construed as limiting the scope of the invention in any manner. All publications mentioned herein are incorporated by reference in their entirety.

Analytical LC-MS Conditions

LC-MS-data given in the subsequent specific experimental descriptions refer (unless otherwise noted) to the following conditions:

| | |
|---|---|
| System: | Waters Acquity UPLC-MS: Binary Solvent Manager, Sample Manager/Organizer, Column Manager, PDA, ELSD, SQD 3001 or ZQ4000 |
| Column: | Acquity UPLC BEH C18 1.7 50 × 2.1 mm |
| Solvent: | A1 = water + 0.1% vol. formic acid (99%)<br>A2 = water + 0.2% vol. ammonia (32%)<br>B1 = acetonitrile |
| Gradient: | 0-1.6 min 1-99% B, 1.6-2.0 min 99% B |
| Flow: | 0.8 mL/min |
| Temperature: | 60° C. |
| Injection: | 2.0 μl |
| Detection: | DAD scan range 210-400 nm -> Peaktable<br>ELSD |
| Methods: | MS ESI+, ESI− Switch -> various scan ranges (Report Header<br>Method 1: A1 + B1 = C:\MassLynx\Mass_100_1000.flp<br>Method 2: A1 + B1 = C:\MassLynx\$NH_3$_Mass_100_1000.flp |

Preparative HPLC Conditions

"Purification by preparative HPLC" in the subsequent specific experimental descriptions refers to (unless otherwise noted) the following conditions:

Analytics (Pre- and Post Analytics: Method A):

| | |
|---|---|
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.1% vol. formic acid (99%)<br>B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 μl |
| Detection: | DAD scan range 210-400 nm<br>MS ESI+, ESI−, scan range 160-1000 m/z<br>ELSD |
| Methods: | Purify_pre.flp<br>Purify_post.flp |

Analytics (Pre- and Post Analytics: Method B):

| | |
|---|---|
| System: | Waters Acquity UPLC-MS: Binary Solvent Manager, Sample Manager/Organizer, Column Manager, PDA, ELSD, SQD 3001 |
| Column: | Acquity BEH C18 1.7 50 × 2.1 mm |
| Solvent: | A = water + 0.2% vol. ammonia (32%)<br>B = acetonitrile |
| Gradient: | 0-1.6 min 1-99% B, 1.6-2.0 min 99% B |
| Flow: | 0.8 mL/min |
| Temperature: | 60° C. |
| Injection: | 2.0 μl |
| Detection: | DAD scan range 210-400 nm<br>MS ESI+, ESI−, scan range 160-1000 m/z<br>ELSD |
| Methods: | Purify_pre.flp<br>Purify_post.flp |

Preparative HPLC (Method Acidic):

| | |
|---|---|
| System: | Waters Autopurificationsystem: Pump 2545, Sample Manager 2767, CFO, DAD 2996, ELSD 2424, SQD 3001 |
| Column: | XBridge C18 5 μm 100 × 30 mm |
| Solvent: | A = water + 0.1% vol. formic acid (99%)<br>B = acetonitrile |
| Gradient: | 0-1 min 1% B, 1-8 min 1-99% B, 8-10 min 99% B |
| Flow: | 50 mL/min |
| Temperature: | RT |
| Solution: | max. 250 mg/2.5 mL dimethyl sufoxide or DMF |
| Injection: | 1 × 2.5 mL |
| Detection: | DAD scan range 210-400 nm<br>MS ESI+, ESI−, scan range 160-1000 m/z |

Preparative HPLC (Method basic):

| | |
|---|---|
| System: | Waters Autopurificationsystem: Pump 2545, Sample Manager 2767, CFO, DAD 2996, ELSD 2424, SQD 3001 |
| Column: | XBridge C18 5 μm 100 × 30 mm or Chromatorex RP C-18 10 μm 125*30 mm |
| Solvent: | A = water + 0.2% vol. ammonia (32%)<br>B = acetonitrile |
| Gradient: | 0-1 min 1% B, 1-8 min 1-99% B, 8-10 min 99% B |
| Flow: | 50 mL/min |
| Temperature: | RT |
| Solution: | max. 250 mg/2.5 mL dimethyl sufoxide or DMF |
| Injection: | 1 × 2.5 mL |
| Detection: | DAD scan range 210-400 nm<br>MS ESI+, ESI−, scan range 160-1000 m/z |

Preparative HPLC (Method Chiral):

| | |
|---|---|
| System: | Labomatic Pumpe: HD-5000, Labomatic SP-3000, Labocord 5000, Labomatic Labcol Vario 4000, Gilson GX-241, |
| Column: | Chiralpak IB 5 μm 250 × 30 mm |
| Solvent: | A = ACN + 0.1% DEA<br>B = EtOH |
| Flow: | 50 mL/min |
| Temperature: | RT |
| Detection: | MWD 280 nm |

Flash Column Chromatography Conditions

"Purification by (flash) column chromatography" as stated in the subsequent specific experimental descriptions refers to the use of a Biotage Isolera purification system. For technical specifications see "Biotage product catalogue" on www.biotage.com.

EXAMPLES

Example 1 rel-(5R,7S)-6,6-Dimethyl-3-(phenylamino)-2-(pyridin-4-yl)-1,5,6,7-tetrahydro-4H-5,7-methanoindol-4-one

1-2: rel-(1S,5R)-2-Hydroxy-6,6-dimethyl-4-oxo-N-phenylbicyclo[3.1.1]hept-2-ene-3-carbothioamide

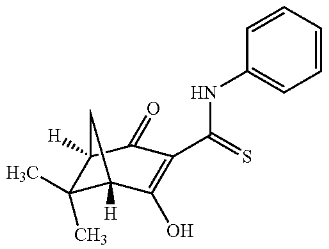 [SMILES: CC1(C)[C@@H]2C[C@H]1C(=O)C(C(=S)Nc1ccccc1)=C2O]

To a solution of 6,6-dimethylbicyclo[3.1.1]heptane-2,4-dione (5.00 g, 32.9 mmol; can be prepared according to Tetrahedron Letters, 2006, 47(13), 2217) and phenylisothiocyanate (3.9 mL, 32.9 mmol) in MeCN (30 mL) was added DBU (8.2 mL, 54.9 mmol) and the mixture was stirred at RT for 16 h. The mixture was poured into ice cold water and conc. hydrochloric acid (8.3 mL) was added. The precipitate was filtered, washed with water and dried to give the title compound (8.59 g, 91%).

1-1: rel-(1S,5R)-6,6-Dimethyl-4-oxo-N-phenyl-2-[(pyridin-4-ylmethyl)amino]bicyclo[3.1.1]hept-2-ene-3-carbothioamide

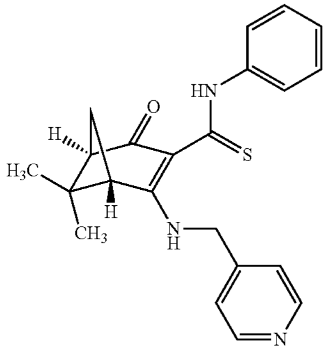 [SMILES: CC1(C)[C@@H]2C[C@H]1C(=O)C(C(=S)Nc1ccccc1)=C2NCc1ccncc1]

A solution rel-(1S,5R)-2-hydroxy-6,6-dimethyl-4-oxo-N-phenylbicyclo[3.1.1]hept-2-ene-3-carbothioamide (1-2; 1.28 g, 4.45 mmol) and 4-(methylamino)pyridine (963 mg, 8.91 mmol) in DMA (12.8 mL) was heated at 120° C. for 1 h. The mixture was concentrated and crystallized from EtOAc to give the title compound (1.14 g, 68%).

rel-(5R,7S)-6,6-Dimethyl-3-(phenylamino)-2-(pyridin-4-yl)-1,5,6,7-tetrahydro-4H-5,7-methanoindol-4-one

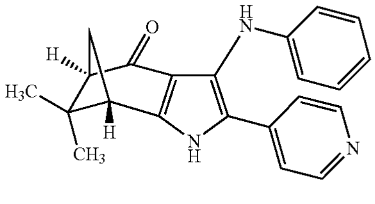 [SMILES: CC1(C)[C@@H]2C[C@H]1C(=O)c1c2[nH]c(-c2ccncc2)c1Nc1ccccc1]

To a solution of rel-(1S,5R)-6,6-dimethyl-4-oxo-N-phenyl-2-[(pyridin-4-ylmethyl)amino]bicyclo[3.1.1]hept-2-ene-3-carbothioamide (1-1; 50 mg, 132 μmol) in EtOH (2.5 mL) was added Pd/C (141 mg, 10%) and the mixture was stirred at 90° C. for 5 h. TFA (10 μL) was added and stirring was continued at 90° C. for 16 h. After cooling, DCM was added, the mixture filtered and purified by Biotage (SNAP silica 11 g, EtOH:DCM) to give the title compound (21 mg, 46%).

$^1$H NMR (400 MHz, DMSO-$d_6$), δ [ppm] 0.84 (3H), 1.55 (3H), 2.18 (1H), 2.45 (1H), 3.03-3.14 (2H), 6.56-6.62 (3H), 7.03 (2H), 7.47 (1H), 7.50 (2H), 8.39 (2H), 12.03 (1H)

Example 2 rel-(5R,7S)-2-(2-Aminopyridin-4-yl)-6,6-dimethyl-3-(phenylamino)-1,5,6,7-tetrahydro-4H-5,7-methanoindol-4-one

2-1: (1S,5R)-2-{[(2-Aminopyridin-4-yl)methyl]amino}-6,6-dimethyl-4-oxo-N-phenylbicyclo[3.1.1]hept-2-ene-3-carbothioamide

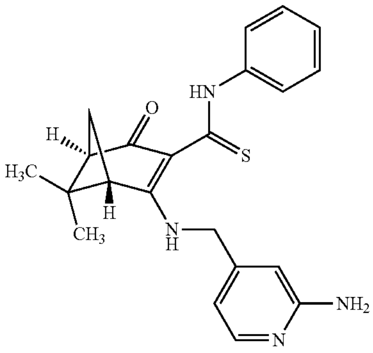 [SMILES: CC1(C)[C@@H]2C[C@H]1C(=O)C(C(=S)Nc1ccccc1)=C2NCc1ccnc(N)c1]

A solution of rel-(1S,5R)-2-hydroxy-6,6-dimethyl-4-oxo-N-phenylbicyclo[3.1.1]hept-2-ene-3-carbothioamide (1-2; 5.00 g, 17.4 mmol) and 4-(methylamino)pyridine (4.29 g, 34.8 mmol) in DMA (50 mL) was heated at 125° C. for 1.5 h. The mixture was concentrated and purified by Biotage (SNAP silica 340 g, EtOH:DCM) to give the title compound (6.94 g, 91%).

rel-(5R,7S)-2-(2-Aminopyridin-4-yl)-6,6-dimethyl-3-(phenylamino)-1,5,6,7-tetrahydro-4H-5,7-methanoindol-4-one

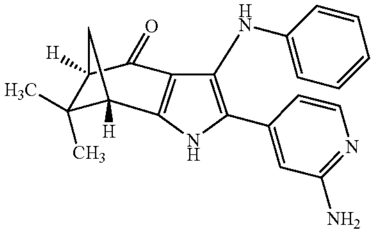

To a solution of (1S,5R)-2-{[(2-aminopyridin-4-yl)methyl]amino}-6,6-dimethyl-4-oxo-N-phenylbicyclo[3.1.1]hept-2-ene-3-carbothioamide (2-1; 6.24 g, 15.9 mmol) in DMA (300 mL) was added Pd/C (16.9 g, 10%), TFA (1.2 mL) and the mixture was stirred at 130° C. for 6 h. After cooling, DCM was added, the mixture filtered and purified by Biotage (SNAP silica 340 g, EtOH:DCM) to give the title compound (2.04 g, 36%).

$^1$H NMR (400 MHz, DMSO-$d_6$), δ [ppm] 0.82 (3H), 1.54 (3H), 2.16 (1H), 2.41 (1H), 3.03-3.10 (2H), 5.70 (2H), 6.55-6.63 (4H), 6.74 (1H), 7.03 (2H), 7.27 (1H), 7.77 (1H), 11.83 (1H)

Example 3

(5R,7S or 5S,7R)-2-(2-Aminopyridin-4-yl)-6,6-dimethyl-3-(phenylamino)-1,5,6,7-tetrahydro-4H-5,7-methanoindol-4-one

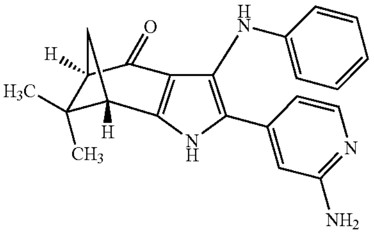

or

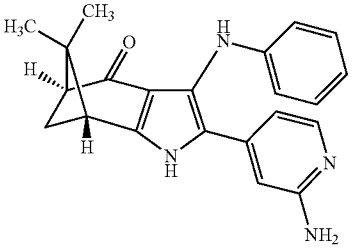

rel-(5R,7S)-2-(2-Aminopyridin-4-yl)-6,6-dimethyl-3-(phenylamino)-1,5,6,7-tetrahydro-4H-5,7-methanoindol-4-one (2; 100 mg, 279 μmol) were separated by preparative HPLC (chiral method) to give the title compound (30 mg, 28%).

$^1$H NMR (400 MHz, DMSO-$d_6$), δ [ppm] 0.82 (3H), 1.54 (3H), 2.16 (1H), 2.41 (1H), 3.03-3.10 (2H), 5.70 (2H), 6.55-6.63 (4H), 6.74 (1H), 7.03 (2H), 7.27 (1H), 7.77 (1H), 11.83 (1H)

Example 4

(5S,7R or 5R,7S)-2-(2-Aminopyridin-4-yl)-6,6-dimethyl-3-(phenylamino)-1,5,6,7-tetrahydro-4H-5,7-methanoindol-4-one

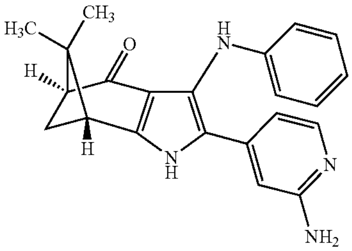

or

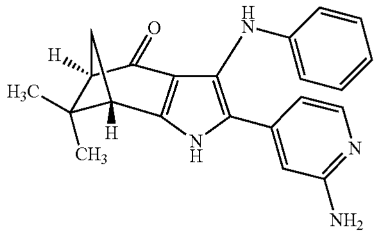 [SMILES: CC1(C)[C@@H]2C[C@H]1C(=O)c1c2[nH]c(-c2ccnc(N)c2)c1Nc1ccccc1]

rel-(5R,7S)-2-(2-Aminopyridin-4-yl)-6,6-dimethyl-3-(phenylamino)-1,5,6,7-tetrahydro-4H-5,7-methanoindol-4-one (2; 100 mg, 279 μmol) were separated by preparative HPLC (chiral method) to give the title compound (33 mg, 31%).

$^1$H NMR (400 MHz, DMSO-$d_6$), δ [ppm] 0.82 (3H), 1.54 (3H), 2.16 (1H), 2.41 (1H), 3.03-3.10 (2H), 5.70 (2H), 6.55-6.63 (4H), 6.74 (1H), 7.03 (2H), 7.27 (1H), 7.77 (1H), 11.83 (1H)

Example 5

N-4-[rel-(5R,7S)-6,6-Dimethyl-4-oxo-3-(phenylamino)-4,5,6,7-tetrahydro-1H-5,7-methanoindol-2-yl]pyridin-2-ylacetamide

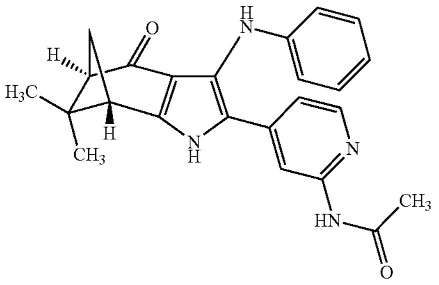 [SMILES: CC(=O)Nc1cc(-c2[nH]c3c(c2Nc2ccccc2)C(=O)[C@@H]2C[C@H]3C2(C)C)ccn1]

A mixture of rel-(5R,7S)-2-(2-aminopyridin-4-yl)-6,6-dimethyl-3-(phenylamino)-1,5,6,7-tetrahydro-4H-5,7-methanoindol-4-one (2; 20 mg, 56 μmol), acetyl chloride (20 μL, 279 μmol), pyridine (78 μL) in THF (1.5 mL) was stirred at RT for 1 h. MeOH was added, the mixture concentrated and purified by preparative TLC (MeOH:DCM) to give the title compound (14 mg, 60%).

$^1$H NMR (400 MHz, DMSO-$d_6$), δ [ppm] 0.83 (3H), 1.55 (3H), 2.07 (3H), 2.17 (1H), 2.43 (1H), 3.05-3.14 (2H), 6.58

(1H), 6.60 (2H), 7.03 (2H), 7.25 (1H), 7.40 (1H), 8.10 (1H), 8.23 (1H), 10.32 (1H), 12.04 (1H)

Example 6

N-4-[rel-(5R,7S)-6,6-Dimethyl-4-oxo-3-(phenylamino)-4,5,6,7-tetrahydro-1H-5,7-methanoindol-2-yl]pyridin-2-ylcyclopropanecarboxamide

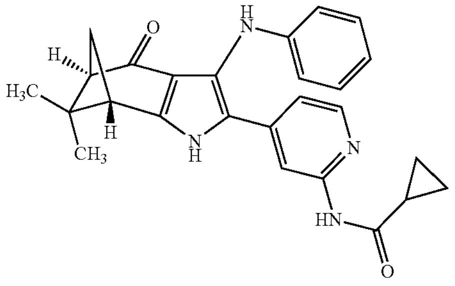 [SMILES: CC1(C)[C@@H]2C[C@H]1C(=O)c1c2[nH]c(-c2ccnc(NC(=O)C3CC3)c2)c1Nc1ccccc1]

A mixture of rel-(5R,7S)-2-(2-aminopyridin-4-yl)-6,6-dimethyl-3-(phenylamino)-1,5,6,7-tetrahydro-4H-5,7-methanoindol-4-one (2; 50 mg, 139 μmol), cyclopropanecarbonyl chloride (63 μL, 697 μmol), pyridine (194 μL) in THF (4 mL) was stirred at RT for 16 h. MeOH was added, the mixture concentrated and purified by preparative TLC (MeOH:DCM) to give the title compound (25 mg, 42%).

$^1$H NMR (400 MHz, DMSO-$d_6$), δ [ppm] 0.79 (4H), 0.81 (3H), 1.52 (3H), 1.98 (1H), 2.15 (1H), 2.41 (1H), 3.03-3.12 (2H), 6.54-6.60 (3H), 7.01 (2H), 7.23 (1H), 7.36 (1H), 8.08 (1H), 8.21 (1H), 10.61 (1H), 12.00 (1H)

Example 7 methyl 4-[rel-(5R,7S)-6,6-Dimethyl-4-oxo-3-(phenylamino)-4,5,6,7-tetrahydro-1H-5,7-methanoindol-2-yl]pyridin-2-ylcarbamate

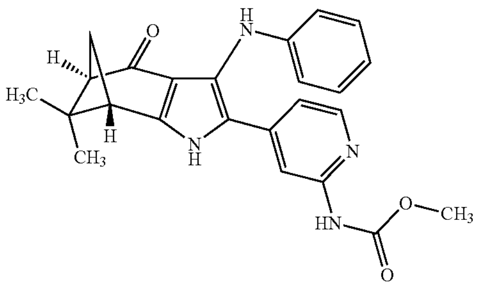

A mixture of rel-(5R,7S)-2-(2-aminopyridin-4-yl)-6,6-dimethyl-3-(phenylamino)-1,5,6,7-tetrahydro-4H-5,7-methanoindol-4-one (2; 50 mg, 139 μmol), methyl carbonochloridate (54 μL, 697 μmol), pyridine (113 μL) in THF (4 mL) was stirred at RT for 16 h. MeOH was added, the mixture concentrated and purified by preparative TLC (MeOH:DCM) to give the title compound (8 mg, 13%).

$^1$H NMR (400 MHz, DMSO-$d_6$), δ [ppm] 0.83 (3H), 1.55 (3H), 2.17 (1H), 2.44 (1H), 3.05-3.14 (2H), 3.65 (3H), 6.56-6.62 (3H), 7.03 (2H), 7.22 (1H), 7.40 (1H), 7.99 (1H), 8.07 (1H), 9.98 (1H), 12.04 (1H)

Example 8

1-4-[rel-(5R,7S)-6,6-Dimethyl-4-oxo-3-(phenylamino)-4,5,6,7-tetrahydro-1H-5,7-methanoindol-2-yl]pyridin-2-yl-3-ethylurea

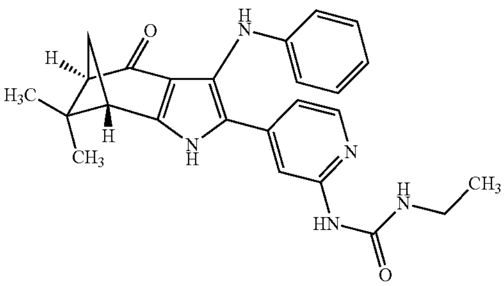 [SMILES: CCNC(=O)Nc1cc(-c2[nH]c3c(c2Nc2ccccc2)C(=O)[C@@H]2C[C@H]3C2(C)C)ccn1]

A mixture of rel-(5R,7S)-2-(2-aminopyridin-4-yl)-6,6-dimethyl-3-(phenylamino)-1,5,6,7-tetrahydro-4H-5,7-methanoindol-4-one (2; 50 mg, 139 μmol), isocyanatoethane (33 μL, 418 μmol) in pyridine (1 mL) was stirred at RT for 16 h. The mixture was concentrated and purified by preparative TLC (MeOH:DCM) to give the title compound (33 mg, 52%).

$^1$H NMR (400 MHz, DMSO-$d_6$), δ [ppm] 0.83 (3H), 1.08 (3H), 1.54 (3H), 2.17 (1H), 2.43 (1H), 3.05-3.22 (4H), 6.56-6.63 (3H), 7.03 (2H), 7.09 (1H), 7.35 (1H), 7.51 (1H), 8.00 (1H), 8.05 (1H), 9.05 (1H), 11.98 (1H)

Example 9

1-cyclopropyl-3-4-[rel-(5R,7S)-6,6-Dimethyl-4-oxo-3-(phenylamino)-4,5,6,7-tetrahydro-1H-5,7-methanoindol-2-yl]pyridin-2-ylurea

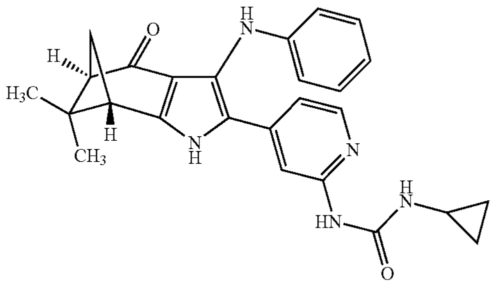 [SMILES: CC1(C)[C@@H]2C[C@H]1C(=O)c1c2[nH]c(-c2ccnc(NC(=O)NC3CC3)c2)c1Nc1ccccc1]

A mixture of rel-(5R,7S)-2-(2-aminopyridin-4-yl)-6,6-dimethyl-3-(phenylamino)-1,5,6,7-tetrahydro-4H-5,7-methanoindol-4-one (2; 50 mg, 139 μmol), isocyanatocyclopropane (29 μL, 418 μmol) in pyridine (1 mL) was stirred at RT for 16 h. The mixture was concentrated and purified by preparative TLC (MeOH:DCM) to give the title compound (43 mg, 66%).

$^1$H NMR (400 MHz, DMSO-$d_6$), δ [ppm] 0.41 (2H), 0.64 (2H), 0.81 (3H), 1.53 (3H), 2.15 (1H), 2.42 (1H), 2.57 (1H), 3.03-3.12 (2H), 6.54-6.60 (3H), 7.01 (2H), 7.08 (1H), 7.32 (1H), 7.56 (1H), 7.97 (1H), 8.04 (1H), 8.95 (1H), 11.96 (1H)

Example 10 rel-(5R,7S)-2-(3-Fluoropyridin-4-yl)-6,6-dimethyl-3-(phenylamino)-1,5,6,7-tetrahydro-4H-5,7-methanoindol-4-one 10-1: rel-(1S,5R)-2-{[(3-Fluoropyridin-4-yl)methyl]amino}-6,6-dimethyl-4-oxo-N-phenylbicyclo[3.1.1]hept-2-ene-3-carbothioamide

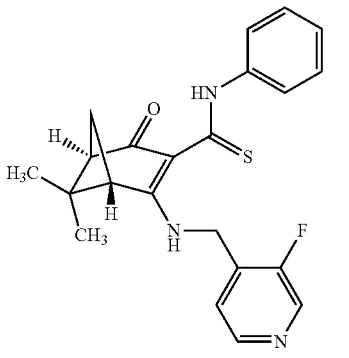 [SMILES: CC1(C)[C@@H]2C[C@H]1C(=O)C(C(=S)Nc1ccccc1)=C2NCc1ccncc1F]

A solution rel-(1S,5R)-2-hydroxy-6,6-dimethyl-4-oxo-N-phenylbicyclo[3.1.1]hept-2-ene-3-carbothioamide (1-2; 500 mg, 1.74 mmol) and 1-(3-fluoropyridin-4-yl)methanamine (439 mg, 3.48 mmol) in DMA (5 mL) was heated at 120° C. for 1 h. The mixture was concentrated and crystallized from EtOAc to give the title compound (447 mg, 65%).

rel-(5R,7S)-2-(3-Fluoropyridin-4-yl)-6,6-dimethyl-3-(phenylamino)-1,5,6,7-tetrahydro-4H-5,7-methanoindol-4-one

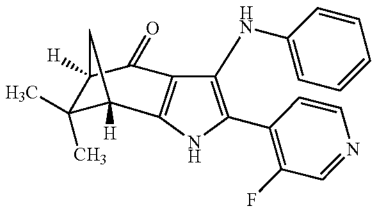 [SMILES: CC1(C)[C@@H]2C[C@H]1C(=O)c1c2[nH]c(-c2ccncc2F)c1Nc1ccccc1]

To a solution of rel-(1S,5R)-2-{[(3-fluoropyridin-4-yl)methyl]amino}-6,6-dimethyl-4-oxo-N-phenylbicyclo[3.1.1]hept-2-ene-3-carbothioamide (10-1; 245 mg, 619 μmol), TFA (48 μL) in DMA (12.3 mL) was added Pd/C (659 mg, 10%) and the mixture was stirred at 120° C. for 5 h. After cooling, DCM was added, the mixture filtered and purified by Biotage (SNAP silica 28 g, EtOH:DCM) and preparative TLC (MeOH:DCM) to give the title compound (21 mg, 9%).

$^1$H NMR (400 MHz, DMSO-$d_6$), δ [ppm] 0.82 (3H), 1.53 (3H), 2.17 (1H), 2.44 (1H), 3.07 (1H), 3.15 (1H), 6.57 (1H), 6.59 (2H), 7.01 (2H), 7.48 (1H), 7.49 (1H), 8.24 (1H), 8.50 (1H), 11.75 (1H)

Example 11 rel-(4aR,7aS)-6-Methyl-3-(phenylamino)-2-(pyridin-4-yl)-1,4a,5,6,7a,8-hexahydropyrrolo[3,4-f]indole-4,7-dione 11-3: Methyl (1 RS)-5-oxo-4-(phenylcarbamothioyl)-3-[(pyridin-4-ylmethyl)amino]cyclohex-3-ene-1-carboxylate

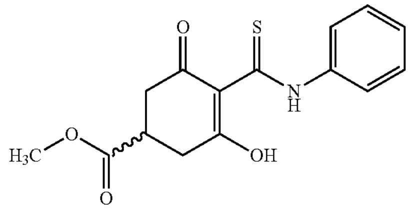 [SMILES: COC(=O)C1CC(=O)C(C(=S)Nc2ccccc2)=C(O)C1]

To a solution of methyl (1 RS)-3-hydroxy-5-oxocyclohex-3-ene-1-carboxylate (630 mg, 3.70 mmol; commercially available from FCH Group Company) and phenylisothiocyanate (443 μL, 3.72 mmol) in MeCN (5.7 mL) was added DBU (867 μL, 5.81 mmol) at 3° C. and the mixture was stirred at RT for 24 h. The mixture was concentrated and purified by Biotage (SNAP silica 100 g, EtOAc:Hexane) to give the title compound (216 mg, 19%).

11-2: Methyl (1 RS)-5-oxo-4-(phenylcarbamothioyl)-3-[(pyridin-4-ylmethyl)amino]cyclohex-3-ene-1-carboxylate

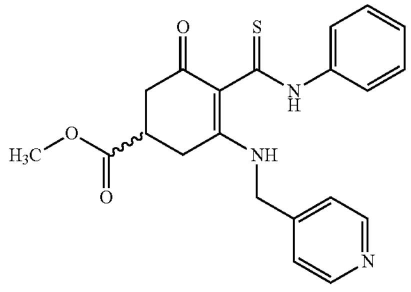 [SMILES: COC(=O)C1CC(=O)C(C(=S)Nc2ccccc2)=C(NCc2ccncc2)C1]

A solution of methyl (1 RS)-5-oxo-4-(phenylcarbamothioyl)-3-[(pyridin-4-ylmethyl)amino]cyclohex-3-ene-1-carboxylate (11-3; 3.00 g, 9.83 mmol) and 4-(methylamino)pyridine (2.0 mL, 19.6 mmol) in dioxane (15 mL) was heated at 120° C. for 1.5 h. The mixture was concentrated and purified by Biotage (SNAP silica 340 g, MeOH:DCM) to give the title compound (2.71 g, 70%).

11-1: Methyl (6RS)-3-anilino-4-oxo-2-(pyridin-4-yl)-4,5,6,7-tetrahydro-1H-indole-6-carboxylate

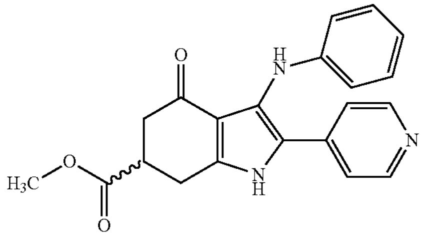 [SMILES: COC(=O)C1CC(=O)c2c([nH]c(-c3ccncc3)c2Nc2ccccc2)C1]

A mixture of methyl (1 RS)-5-oxo-4-(phenylcarbamothioyl)-3-[(pyridin-4-ylmethyl)amino]cyclohex-3-ene-1-carboxylate (11-2; 2.70 g, 6.83 mmol), hydrogen peroxide (34% in water, 1.23 mL, 13.7 mmol) in MeOH (50 mL) was heated at 80° C. for 16 h. The mixture was concentrated and purified by Biotage (SNAP silica 100 g, MeOH:DCM) to give the title compound (1.42 g, 58%).

rel-(4aR,7aS)-6-Methyl-3-(phenylamino)-2-(pyridin-4-yl)-1,4a,5,6,7a,8-hexahydropyrrolo[3,4-f]indole-4,7-dione

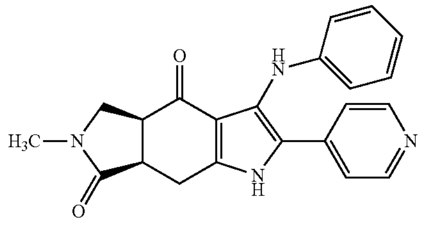 [SMILES: CN1C[C@H]2C(=O)c3c([nH]c(-c4ccncc4)c3Nc3ccccc3)C[C@H]2C1=O]

A mixture of methyl (6RS)-3-anilino-4-oxo-2-(pyridin-4-yl)-4,5,6,7-tetrahydro-1H-indole-6-carboxylate (11-1; 50 mg, 138 μmol), methanamine (692 μL, 2M in THF) in DMSO (2 mL) was heated at 120° C. for 3 days. The mixture was concentrated and purified by preparative HPLC (basic method) to give the title compound (13 mg, 23%).

$^{1}H$ NMR (400 MHz, DMSO-$d_6$), δ [ppm] 2.68 (3H), 3.04 (1H), 3.09-3.18 (2H), 3.27 (1H), 3.52 (1H), 3.63 (1H), 6.55 (2H), 6.63 (1H), 7.03 (2H), 7.43 (2H), 7.53 (1H), 8.41 (2H), 12.03 (1H)

Example 12 rel-(4aR,5aR)-3-(Phenylamino)-2-(pyridin-4-yl)-4a,5,5a,6-tetrahydrocyclopropa[f]indol-4(1H)-one 12-5: (4RS)-4-({[tert-butyl(diphenyl)silyl]oxy}methyl)-2-hydroxy-6-oxo-N-phenylcyclohex-1-ene-1-carbothioamide

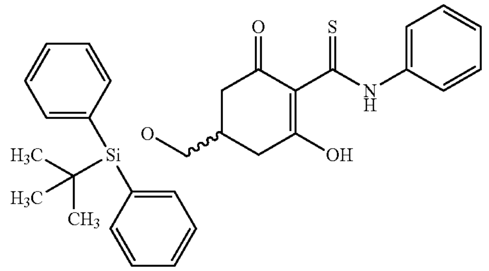

To a solution of (5RS)-5-({[tert-butyl(diphenyl)silyl]oxy}methyl)-3-hydroxycyclohex-2-en-1-one (20.0 g, 52.6 mmol; can be prepared according to EP 2617720) and phenylisothiocyanate (6.29 mL, 52.6 mmol) in MeCN (90 mL) was added DBU (13.3 mL, 89.3 mmol) at 3° C. and the mixture was stirred at RT for 16 h. The mixture was concentrated and purified by Biotage (SNAP silica 340 g, EtOAc:Hexane) to give the title compound (20.1 g, 74%).

12-4: (4RS)-4-({[tert-Butyl(diphenyl)silyl]oxy}methyl)-6-oxo-N-phenyl-2-[(pyridin-4-ylmethyl)amino]cyclohex-1-ene-1-carbothioamide

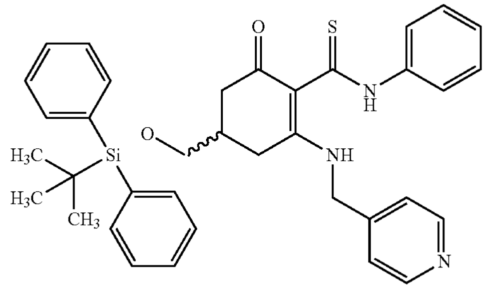

A solution of (4RS)-4-({[tert-butyl(diphenyl)silyl]oxy}methyl)-2-hydroxy-6-oxo-N-phenylcyclohex-1-ene-1-carbothioamide (12-5; 20.1 g, 39.0 mmol) and 4-(methylamino)pyridine (7.92 mL, 77.9 mmol) in DMA (110 mL) was heated at 100° C. for 2 h. The mixture was concentrated and purified by Biotage (SNAP silica 340 g, EtOAc:Hexane) to give the title compound (11.0 g, 67%).

12-3: 3-Anilino-6-({[tert-butyl(diphenyl)silyl]oxy}methyl)-2-(pyridin-4-yl)-1,5,6,7-tetrahydro-4H-indol-4-one

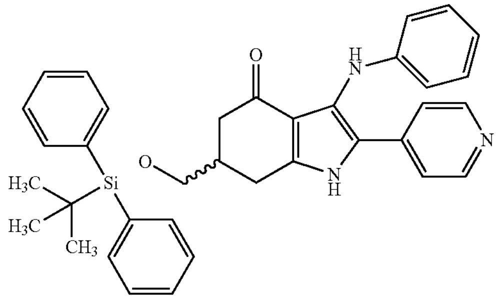

A mixture of (4RS)-4-({[tert-butyl(diphenyl)silyl]oxy}methyl)-6-oxo-N-phenyl-2-[(pyridin-4-ylmethyl)amino]cyclohex-1-ene-1-carbothioamide (12-4; 11.0 g, 18.2 mmol), SIBX (45%, 11.3 g, 18.2 mmol) in EtOH (540 mL) was stirred at Rt for 16 h. $Et_3N$ (6 mL) were added, the mixture was concentrated and purified by Biotage (SNAP silica 375 g, EtOH:DCM) to give the title compound (7.70 g, 74%).

12-2: (6RS)-6-(Hydroxymethyl)-3-(phenylamino)-2-(pyridin-4-yl)-1,5,6,7-tetrahydro-4H-indol-4-one

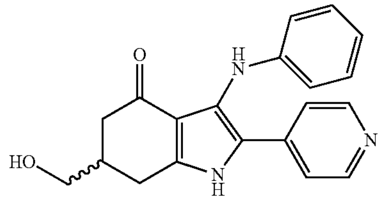 [SMILES: O=C1CC(CO)Cc2[nH]c(-c3ccncc3)c(Nc3ccccc3)c21]

A mixture of 3-anilino-6-({[tert-butyl(diphenyl)silyl]oxy}methyl)-2-(pyridin-4-yl)-1,5,6,7-tetrahydro-4H-indol-4-one (12-3; 10.0 g, 17.5 mmol) and TBAF (22.7 mL, 1M in THF) in THF (250 mL) was stirred at RT for 16 h. EtOAc (1 L) was added, the mixture washed with sodium hydroxide (2.5% in water), brine and dried over sodium sulfate. After filtration and removal of the solvent the residue was purified by Biotage (SNAP silica 340 g, MeOH:DCM) to give the title compound (4.31 g, 74%).

12-1: [(6RS)-3-Anilino-4-oxo-2-(pyridin-4-yl)-4,5,6,7-tetrahydro-1H-indol-6-yl]methyl methanesulfonate

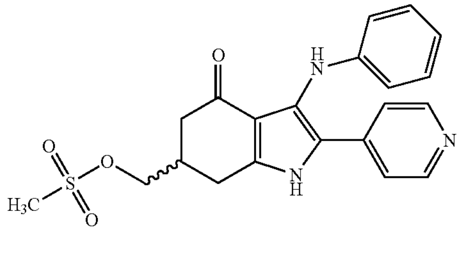 [SMILES: CS(=O)(=O)OCC1CC(=O)c2c([nH]c(-c3ccncc3)c2Nc2ccccc2)C1]

A mixture of (6RS)-6-(hydroxymethyl)-3-(phenylamino)-2-(pyridin-4-yl)-1,5,6,7-tetrahydro-4H-indol-4-one (12-2; 2.00 g, 6.00 mmol), methanesulfonyl chloride (557 μL, 7.20 mmol) in pyridine (32 mL) was stirred at RT for 4 h. MeOH was added, the mixture concentrated and purified by Biotage (SNAP silica 110 g, MeOH:DCM) to give the title compound (2.16 g, 88%).

rel-(4aR,5aR)-3-(Phenylamino)-2-(pyridin-4-yl)-4a,5,5a,6-tetrahydrocyclopropa[f]indol-4(1H)-one

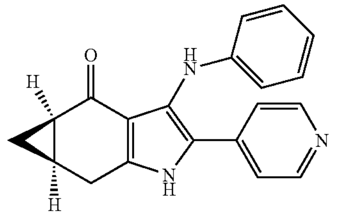

A mixture of [(6RS)-3-anilino-4-oxo-2-(pyridin-4-yl)-4,5,6,7-tetrahydro-1H-indol-6-yl]methyl methanesulfonate (12-1; 100 mg, 244 μmol), sodium methanolate (225 μL, 5.4 M in MeOH) was stirred at 50° C. for 16 h. The mixture was concentrated and purified by preparative TLC (MeOH:DCM) to give the title compound (29 mg, 37%).

$^1$H NMR (400 MHz, DMSO-$d_6$), δ [ppm] 0.62 (1H), 1.25 (1H), 1.67 (1H), 1.81 (1H), 3.21 (2H), 6.54 (2H), 6.62 (1H), 7.03 (2H), 7.43 (1H), 7.45 (2H), 8.39 (2H), 11.82 (1H)

Example 13

(4aR,5aR or 4aS,5aS)-3-(Phenylamino)-2-(pyridin-4-yl)-4a,5,5a,6-tetrahydrocyclopropa[f]indol-4(1H)-one

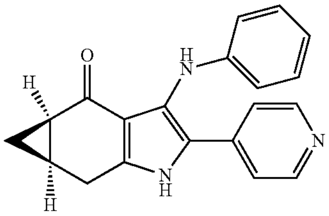 [SMILES: O=C1c2c([nH]c(-c3ccncc3)c2Nc2ccccc2)C[C@H]2C[C@@H]12]

or

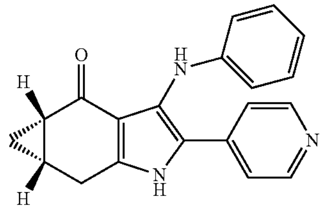

rel-(4aR,5aR)-3-(Phenylamino)-2-(pyridin-4-yl)-4a,5,5a,6-tetrahydrocyclopropa[f]indol-4(1H)-one (12; 29 mg, 92 μmol) were separated by preparative HPLC (chiral method) to give the title compound (11 mg, 14%).

$^1$H NMR (400 MHz, DMSO-$d_6$), δ [ppm] 0.62 (1H), 1.25 (1H), 1.67 (1H), 1.81 (1H), 3.21 (2H), 6.54 (2H), 6.62 (1H), 7.03 (2H), 7.43 (1H), 7.45 (2H), 8.39 (2H), 11.82 (1H)

Example 14

(4aS,5aS or 4aR,5aR)-3-(Phenylamino)-2-(pyridin-4-yl)-4a,5,5a,6-tetrahydrocyclopropa[f]indol-4(1H)-one

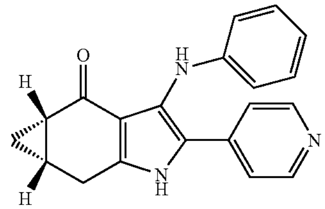

or

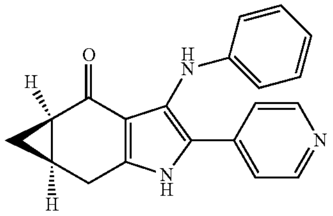

rel-(4aR,5aR)-3-(Phenylamino)-2-(pyridin-4-yl)-4a,5,5a,6-tetrahydrocyclopropa[f]indol-4(1H)-one (12; 29 mg, 92 μmol) were separated by preparative HPLC (chiral method) to give the title compound (10 mg, 13%).

$^1$H NMR (400 MHz, DMSO-$d_6$), δ [ppm] 0.62 (1H), 1.25 (1H), 1.67 (1H), 1.81 (1H), 3.21 (2H), 6.54 (2H), 6.62 (1H), 7.03 (2H), 7.43 (1H), 7.45 (2H), 8.39 (2H), 11.82 (1H)

Example 15 rel-(4aR,5aR)-N-4-[4-oxo-3-(Phenylamino)-1,4,4a,5,5a,6-hexahydrocyclopropa[f]indol-2-yl]pyridin-2-ylacetamide

15-5: (4RS)-2-{[(2-Aminopyridin-4-yl)methyl]amino}-4-({[tert-butyl(diphenyl)silyl]oxy}methyl)-6-oxo-N-phenylcyclohex-1-ene-1-carbothioamide

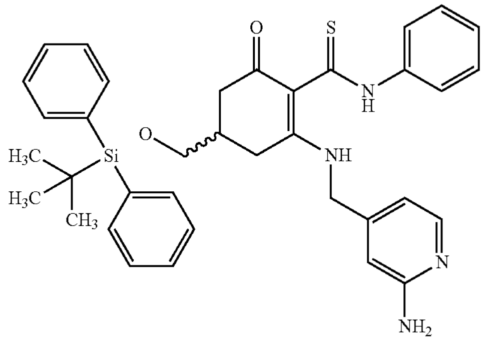

A solution of (4RS)-4-({[tert-butyl(diphenyl)silyl]oxy}methyl)-2-hydroxy-6-oxo-N-phenylcyclohex-1-ene-1-carbothioamide (12-4; 33.9 g, 65.7 mmol) and 4-(aminomethyl)pyridin-2-amine (16.2 g, 131 mmol) in DMA (250 mL) was heated at 120° C. for 2 h. The mixture was concentrated and purified by Biotage (SNAP silica 750 g, EtOH:DCM) to give the title compound (24.8 g, 60%).

15-4: (6RS)-2-(2-Aminopyridin-4-yl)-3-anilino-6-({[tert-butyl(diphenyl)silyl]oxy}methyl)-1,5,6,7-tetrahydro-4H-indol-4-one

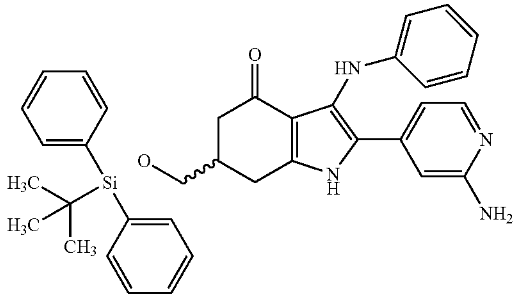

A mixture of (4RS)-2-{[(2-Aminopyridin-4-yl)methyl]amino}-4-({[tert-butyl(diphenyl)silyl]oxy}methyl)-6-oxo-N-phenylcyclohex-1-ene-1-carbothioamide (15-5; 16.3 g, 26.3 mmol), hydrogen peroxide (30% in water, 10.7 mL, 105 mmol) in MeOH (500 mL) was heated at 50° C. for 16 h. The mixture was concentrated and purified by Biotage (SNAP silica 375 g, MeOH:DCM) to give the title compound (8.95 g, 58%).

15-3: N-{4-[(6RS)-3-Anilino-6-({[tert-butyl(diphenyl)silyl]oxy}methyl)-4-oxo-4,5,6,7-tetrahydro-1H-indol-2-yl]pyridin-2-yl}acetamide

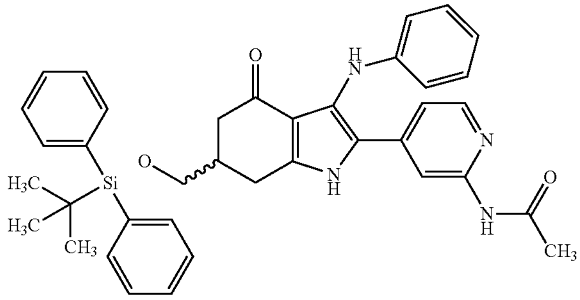

A mixture of (6RS)-2-(2-Aminopyridin-4-yl)-3-anilino-6-({[tert-butyl(diphenyl)silyl]oxy}methyl)-1,5,6,7-tetrahydro-4H-indol-4-one (15-4; 2.34 g, 3.99 mmol), acetyl chloride (425 μL, 5.98 mmol) in THF (100 mL) and pyridine (2.78 mL) was stirred at RT for 1 h. MeOH was added, the mixture concentrated and purified by Biotage (SNAP silica 50 g, MeOH:DCM) to give the title compound (2.46 g, 98%).

15-2: N-4-[(6RS)-6-(Hydroxymethyl)-4-oxo-3-(phenylamino)-4,5,6,7-tetrahydro-1H-indol-2-yl]pyridin-2-ylacetamide

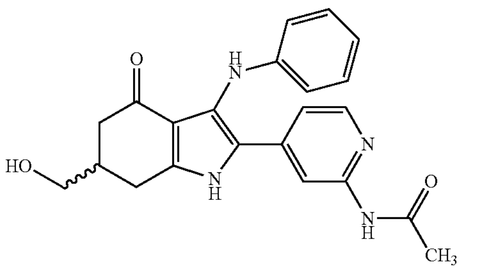 [SMILES: CC(=O)Nc1cc(-c2[nH]c3c(c2Nc2ccccc2)C(=O)CC(CO)C3)ccn1]

A mixture of N-{4-[(6RS)-3-anilino-6-({[tert-butyl(diphenyl)silyl]oxy}methyl)-4-oxo-4,5,6,7-tetrahydro-1H-indol-2-yl]pyridin-2-yl}acetamide (15-3; 2.45 g, 3.90 mmol) and TBAF (4.68 mL, 1M in THF) in THF (65 mL) was stirred at RT for 16 h. EtOAc was added, the mixture washed with sodium hydroxide (2.5% in water), brine and dried over sodium sulfate. After filtration and removal of the solvent the residue was purified by crystallization from MeOH/DCM and Biotage (SNAP silica 25 g, MeOH:DCM) of the mother liquor to give the title compound (1.17 g, 77%).

15-1: [(6RS)-2-(2-Acetamidopyridin-4-yl)-3-anilino-4-oxo-4,5,6,7-tetrahydro-1H-indol-6-yl]methyl methanesulfonate

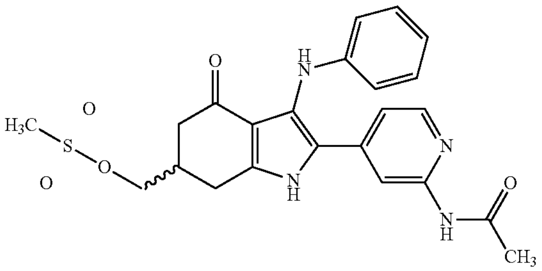

A solution of N-4-[(6RS)-6-(hydroxymethyl)-4-oxo-3-(phenylamino)-4,5,6,7-tetrahydro-1H-indol-2-yl]pyridin-2-ylacetamide (15-1; 1.18 g, 3.01 mmol), DMAP (37 mg, 0.3 mmol) and methanesulfonyl chloride (280 μL, 3.61 mmol) in pyridine (16 mL) was stirred at RT for 5 h. MeOH was added, the mixture concentrated and purified by crystallization from MeOH to give the title compound (1.26 g, 90%).

rel-(4aR,5aR)-N-4-[4-oxo-3-(Phenylamino)-1,4,4a,5,5a,6-hexahydrocyclopropa[f]indol-2-yl]pyridin-2-ylacetamide

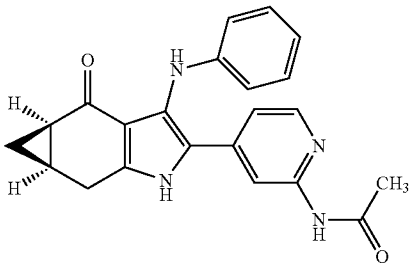 [SMILES: CC(=O)Nc1cc(-c2[nH]c3c(c2Nc2ccccc2)C(=O)[C@@H]2C[C@@H]2C3)ccn1]

A solution of [(6RS)-2-(2-acetamidopyridin-4-yl)-3-anilino-4-oxo-4,5,6,7-tetrahydro-1H-indol-6-yl]methyl methanesulfonate (15-1; 40 mg, 85 μmol), caesium fluoride (16 mg, 102 μmol) and 18-crown-6 (27 mg, 102 μmol) in THF (2 mL) was stirred at 80° C. for 1 h. The mixture was concentrated and purified by preparative TLC (EtOAc) to give the title compound (10 mg, 30%).

$^1$H NMR (400 MHz, DMSO-d$_6$), δ [ppm] 0.62 (1H), 1.24 (1H), 1.66 (1H), 1.80 (1H), 2.08 (3H), 3.13-3.25 (2H), 6.52 (2H), 6.59 (1H), 7.01 (2H), 7.15 (1H), 7.35 (1H), 8.07 (1H), 8.20 (1H), 10.33 (1H), 11.82 (1H)

Example 16 rel-(4aR,5aR)-5a-Methyl-3-(phenylamino)-2-(pyridin-4-yl)-4a,5,5a,6-tetrahydrocyclopropa[f]indol-4(1H)-one 16-4: (4RS)-4-({[tert-Butyl(diphenyl)silyl]oxy}methyl)-4-methyl-6-oxo-N-phenyl-2-[(pyridin-4-ylmethyl)amino]cyclohex-1-ene-1-carbothioamide

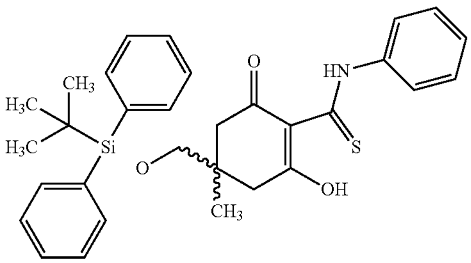

To a solution of (5RS)-5-({[tert-butyl(diphenyl)silyl]oxy}methyl)-3-hydroxy-5-methylcyclohex-2-en-1-one (5.00 g, 12.7 mmol; can be prepared according to Synthesis, 2014, 46 (3), 381-386) and phenylisothiocyanate (1.52 mL, 12.7 mmol) in MeCN (25 mL) was added DBU (1.89 mL, 12.7 mmol) at 3° C. and the mixture was stirred at RT for 2.5 days. The mixture was poured into water, extracted with EtOAc, washed with brine and dried over sodium sulfate. After filtration the mixture was concentrated and purified by Biotage (SNAP silica 100 g, EtOAc:Hexane) to give the title compound (5.18 g, 77%).

16-3: (4RS)-4-({[tert-Butyl(diphenyl)silyl]oxy}methyl)-4-methyl-6-oxo-N-phenyl-2-[(pyridin-4-ylmethyl)amino]cyclohex-1-ene-1-carbothioamide

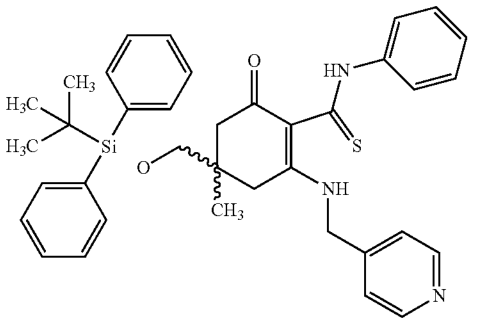

A solution of (4RS)-4-({[tert-butyl(diphenyl)silyl]oxy}methyl)-4-methyl-6-oxo-N-phenyl-2-[(pyridin-4-ylmethyl)amino]cyclohex-1-ene-1-carbothioamide (16-4; 3.33 g, 6.29 mmol) and 4-(methylamino)pyridine (894 μL, 8.80 mmol) in DMA (16.7 mL) was heated at 80° C. for 2 h. The mixture was concentrated and purified by Biotage (SNAP silica 100 g, EtOAc:Hexane) to give the title compound (1.78 g, 43%).

16-2: (6RS)-3-Anilino-6-({[tert-butyl(diphenyl)silyl]oxy}methyl)-6-methyl-2-(pyridin-4-yl)-1,5,6,7-tetrahydro-4H-indol-4-one

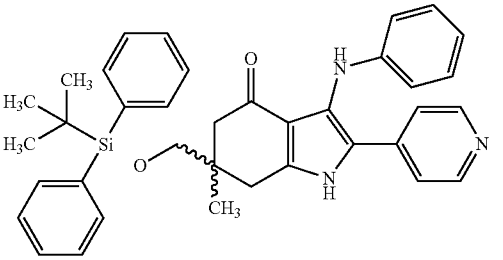

A mixture of (4RS)-4-({[tert-butyl(diphenyl)silyl]oxy}methyl)-4-methyl-6-oxo-N-phenyl-2-[(pyridin-4-ylmethyl)amino]cyclohex-1-ene-1-carbothioamide (16-3; 1.41 g, 2.28 mmol), SIBX (45%, 1.70 g, 2.73 mmol) in MeOH (32 mL) and DCM (85 mL) was stirred at RT for 1 h. The mixture was poured into saturated sodium hydrogencarbonate, extracted with DCM and dried over sodium sulfate. After filtration and concentration the residue was purified by Biotage (SNAP silica 100 g, EtOAc:DCM) to give the title compound (662 mg, 50%).

16-1: (6RS)-6-(Hydroxymethyl)-6-methyl-3-(phenylamino)-2-(pyridin-4-yl)-1,5,6,7-tetrahydro-4H-indol-4-one

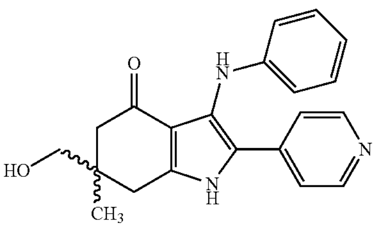

A mixture of (6RS)-3-anilino-6-({[tert-butyl(diphenyl)silyl]oxy}methyl)-6-methyl-2-(pyridin-4-yl)-1,5,6,7-tetrahydro-4H-indol-4-one (16-2; 3.1 g, 5.29 mmol) and TBAF (7.94 mL, 1M in THF) in THF (75 mL) was stirred at 60° C. for 16 h. E tOAc (1 L) was added, the mixture washed with sodium hydroxide (2.5% in water), brine and dried over sodium sulfate. After filtration and removal of the solvent the residue was purified by Biotage (SNAP silica 100 g, MeOH:DCM) to give the title compound (800 mg, 41%).

rel-(4aR,5aR)-5a-Methyl-3-(phenylamino)-2-(pyridin-4-yl)-4a,5,5a,6-tetrahydrocyclopropa[f]indol-4(1H)-one

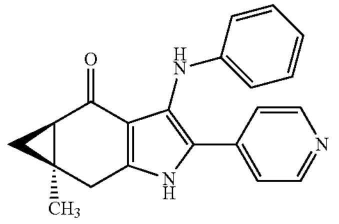

A mixture of (6RS)-6-(hydroxymethyl)-6-methyl-3-(phenylamino)-2-(pyridin-4-yl)-1,5,6,7-tetrahydro-4H-indol-4-one (16-1; 296 mg, 852 μmol) and DPPA (312 μL, 1.45 mmol) in THF (14 mL) was stirred at 0° C. for 5 minutes. DBU (178 μL, 1.19 mmol) was added and stirring continued at RT for 40 h. Sodium azide (554 mg, 8.52 mmol) was added THF exchanged by DMA (10 mL) and the mixture stirred at 140° C. for 1 h. The mixture was poured into water and extracted with EtOAc. The organic layer was washed with brine and dried over sodium sulfate. After filtration and removal of the solvent, the residue was purified by Biotage (SNAP silica 10 g, EtOAc:Hexane) to give the title compound (82 mg, 28%).

$^1$H NMR (400 MHz, DMSO-$d_6$), δ [ppm] 0.79 (1H), 1.12 (1H), 1.31 (3H), 1.52 (1H), 3.00 (1H), 3.22 (1H), 6.54 (2H), 6.61 (1H), 7.02 (2H), 7.37 (1H), 7.45 (2H), 8.39 (2H), 11.78 (1H)

Example 17

(4aR,5aR or 4aS,5aS)-5a-Methyl-3-(phenylamino)-2-(pyridin-4-yl)-4a,5,5a,6-tetrahydrocyclopropa[f]indol-4(1H)-one

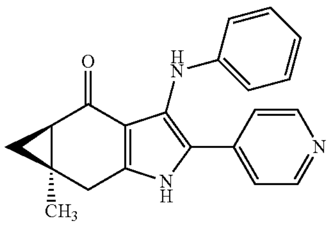 [SMILES: C[C@@]12Cc3[nH]c(-c4ccncc4)c(Nc4ccccc4)c3C(=O)[C@@H]1C2]

or

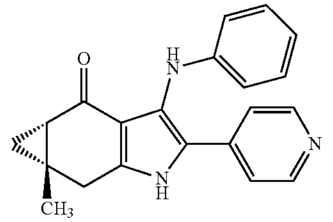

rel-(4aR,5aR)-5a-Methyl-3-(phenylamino)-2-(pyridin-4-yl)-4a,5,5a,6-tetrahydrocyclopropa[f]indol-4(1H)-one (16; 61 mg, 185 μmol) were separated by preparative HPLC (chiral method) to give the title compound (19 mg, 31%).

$^1$H NMR (400 MHz, DMSO-$d_6$), δ [ppm] 0.79 (1H), 1.12 (1H), 1.31 (3H), 1.52 (1H), 3.00 (1H), 3.22 (1H), 6.54 (2H), 6.61 (1H), 7.02 (2H), 7.37 (1H), 7.45 (2H), 8.39 (2H), 11.78 (1H)

Example 18

(4aS,5aS or 4aR,5aR)-5a-Methyl-3-(phenylamino)-2-(pyridin-4-yl)-4a,5,5a,6-tetrahydrocyclopropa[f]indol-4(1H)-one

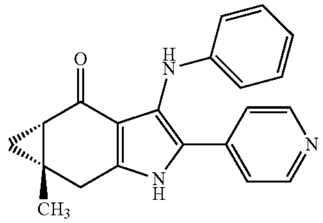

or

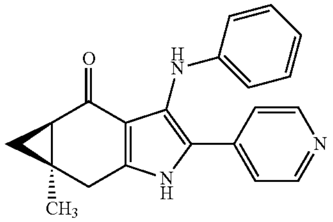

rel-(4aR,5aR)-5a-Methyl-3-(phenylamino)-2-(pyridin-4-yl)-4a,5,5a,6-tetrahydrocyclopropa[f]indol-4(1H)-one (16; 61 mg, 185 μmol) were separated by preparative HPLC (chiral method) to give the title compound (16 mg, 27%).

$^1$H NMR (400 MHz, DMSO-$d_6$), δ [ppm] 0.79 (1H), 1.12 (1H), 1.31 (3H), 1.52 (1H), 3.00 (1H), 3.22 (1H), 6.54 (2H), 6.61 (1H), 7.02 (2H), 7.37 (1H), 7.45 (2H), 8.39 (2H), 11.78 (1H)

Example 19

N-4-[(4aR,5aR or 4aS,5aS)-5a-Methyl-4-oxo-3-(phenylamino)-1,4,4a,5,5a,6-hexahydrocyclopropa[f]indol-2-yl]pyridin-2-ylacetamide

19-6: (4RS)-2-{[(2-Aminopyridin-4-yl)methyl]amino}-4-({[tert-butyl(diphenyl)silyl]oxy}methyl)-4-methyl-6-oxo-N-phenylcyclohex-1-ene-1-carbothioamide

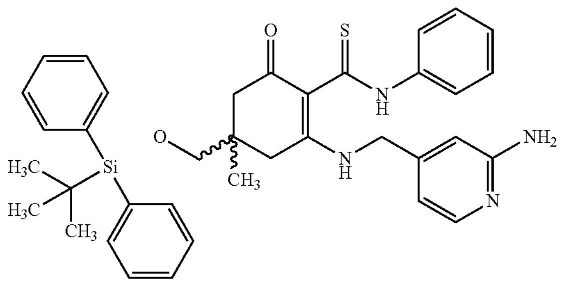

A solution of (4RS)-4-({[tert-butyl(diphenyl)silyl]oxy}methyl)-4-methyl-6-oxo-N-phenyl-2-[(pyridin-4-ylmethyl)amino]cyclohex-1-ene-1-carbothioamide (16-4; 9.9 g, 18.7 mmol) and 4-(aminomethyl)pyridin-2-amine (4.14 g, 33.6 mmol) in DMA (52 mL) was heated at 90-100° C. for 10 h. The mixture was poured into water, extracted with EtOAc, washed with brine and dried over sodium sulfate. After filtration the mixture was concentrated and purified by Biotage (SNAP silica 340 g, EtOAc:Hexane) to give the title compound (6.07 g, 51%).

19-5: (6RS)-2-(2-Aminopyridin-4-yl)-3-anilino-6-({[tert-butyl(diphenyl)silyl]oxy}methyl)-6-methyl-1,5,6,7-tetrahydro-4H-indol-4-one

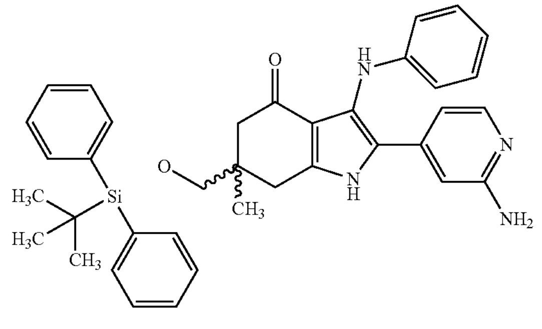

A mixture of (4RS)-2-{[(2-aminopyridin-4-yl)methyl]amino}-4-({[tert-butyl(diphenyl)silyl]oxy}methyl)-4-methyl-6-oxo-N-phenylcyclohex-1-ene-1-carbothioamide (19-6; 27.9 g, 43.9 mmol), hydrogen peroxide (30% in water, 17.9 mL, 176 mmol) in MeOH (836 mL) was heated at 50° C. for 16 h. The mixture was concentrated and purified by Biotage (SNAP silica 340 g, EtOAc:Hexane) to give the title compound (18.6 g, 71%).

19-4: N-{4-[(6RS)-3-Anilino-6-({[tert-butyl(diphenyl)silyl]oxy}methyl)-6-methyl-4-oxo-4,5,6,7-tetrahydro-1H-indol-2-yl]pyridin-2-yl}acetamide

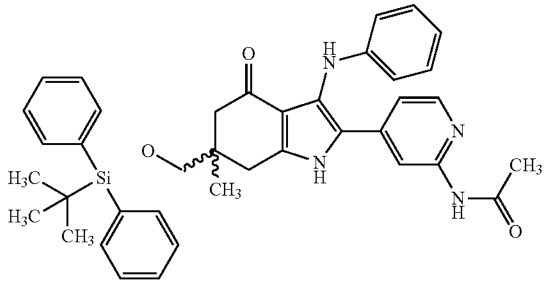

A mixture of (6RS)-2-(2-aminopyridin-4-yl)-3-anilino-6-({[tert-butyl(diphenyl)silyl]oxy}methyl)-6-methyl-1,5,6,7-tetrahydro-4H-indol-4-one (19-5; 1.00 g, 1.66 mmol), acetyl chloride (284 μL, 4.00 mmol), pyridine (2.3 mL) in THF (22 mL) was stirred at RT for 16 h. MeOH was added, the mixture concentrated and purified by Biotage (SNAP silica 50 g, EtOH:DCM) to give the title compound (478 mg, 45%).

19-3: N-{4-[(6RS)-3-Anilino-6-(hydroxymethyl)-6-methyl-4-oxo-4,5,6,7-tetrahydro-1H-indol-2-yl]pyridin-2-yl}acetamide

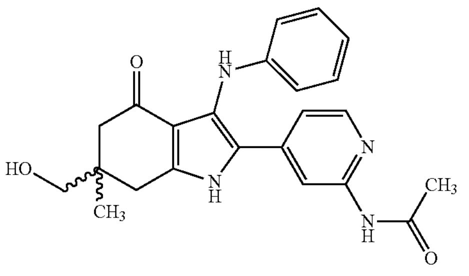

A mixture of N-{4-[(6RS)-3-anilino-6-({[tert-butyl(diphenyl)silyl]oxy}methyl)-6-methyl-4-oxo-4,5,6,7-tetrahydro-1H-indol-2-yl]pyridin-2-yl}acetamide (19-4; 1.04 g, 1.62 mmol), TBAF (4.04 mL, 1M in THF) in THF (23 mL) was stirred at 50° C. for 12 h. EtOAc (100 mL) was added, the mixture washed with sodium hydroxide (2.5% in water), water, brine and dried over sodium sulfate. After filtration and removal of the solvents, the residue was purified by Biotage (SNAP silica 50 g, MeOH:DCM) to give the title compound (552 mg, 76%).

19-2: [(6RS)-2-(2-Acetamidopyridin-4-yl)-3-anilino-6-methyl-4-oxo-4,5,6,7-tetrahydro-1H-indol-6-yl]methyl methanesulfonate

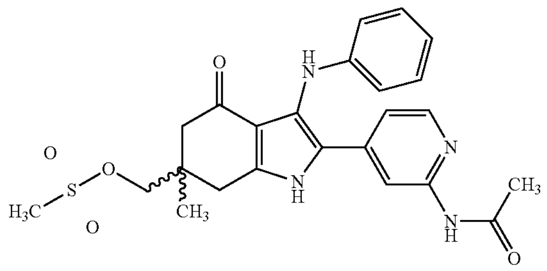

A mixture of N-{4-[(6RS)-3-anilino-6-(hydroxymethyl)-6-methyl-4-oxo-4,5,6,7-tetrahydro-1H-indol-2-yl]pyridin-2-yl}acetamide (19-3; 350 mg, 865 μmol), methanesulfonyl chloride (113 μL, 1.46 mmol), DMAP (11 mg) in pyridine (5 mL) was stirred at RT for 16 h. MeOH was added, the mixture concentrated and purified by Biotage (SNAP silica 25 g, MeOH:DCM) to give the title compound (227 mg, 54%).

19-1: N-4-[rel-(4aR,5aR)-5a-Methyl-4-oxo-3-(phenylamino)-1,4,4a,5,5a,6-hexahydrocyclopropa[f]indol-2-yl]pyridin-2-ylacetamide

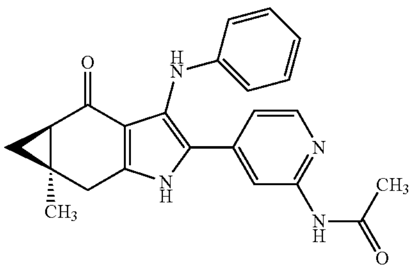

A solution of [(6RS)-2-(2-acetamidopyridin-4-yl)-3-anilino-6-methyl-4-oxo-4,5,6,7-tetrahydro-1H-indol-6-yl]methyl methanesulfonate (19-2; 170 mg, 352 μmol) in DMA (4 mL) was heated at 140° C. for 3 h. The mixture was concentrated and purified by Biotage (SNAP silica 25 g, MeOH:DCM) to give the title compound (134 mg, 98%).

N-4-[(4aR,5aR or 4aS,5aS)-5a-Methyl-4-oxo-3-(phenylamino)-1,4,4a,5,5a,6-hexahydrocyclopropa[f]indol-2-yl]pyridin-2-ylacetamide

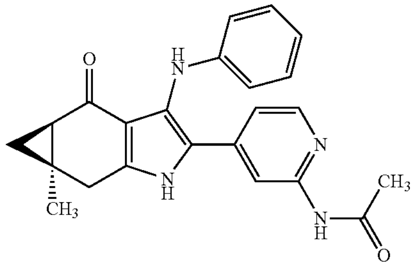 [SMILES: CC(=O)Nc1cc(-c2[nH]c3c(c2Nc2ccccc2)C(=O)[C@@H]2C[C@]2(C)C3)ccn1]

or

-continued

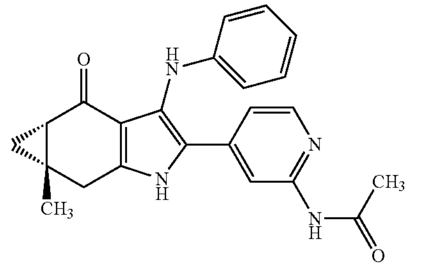

N-4-[rel-(4aR,5aR)-5a-Methyl-4-oxo-3-(phenylamino)-1,4,4a,5,5a,6-hexahydrocyclopropa[f]indol-2-yl]pyridin-2-ylacetamide (19-1; 134 mg, 346 μmol) were separated by preparative HPLC (chiral method) to give the title compound (25 mg, 17%).

$^1$H NMR (400 MHz, $CD_2Cl_2$), δ [ppm] 0.95 (1H), 1.18 (1H), 1.37 (3H), 1.67 (1H), 2.21 (3H), 3.00 (1H), 3.23 (1H), 6.68 (2H), 6.78 (1H), 7.02 (1H), 7.10 (2H), 7.23 (1H), 7.98 (1H), 8.19 (1H), 8.23 (1H), 9.37 (1H)

Example 20

N-4-[(4aS,5aS or 4aR,5aR)-5a-Methyl-4-oxo-3-(phenylamino)-1,4,4a,5,5a,6-hexahydrocyclopropa[f]indol-2-yl]pyridin-2-ylacetamide

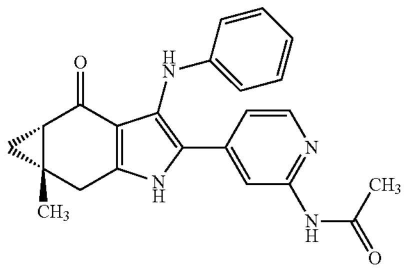

or

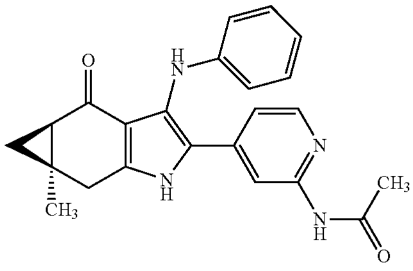

N-4-[rel-(4aR,5aR)-5a-Methyl-4-oxo-3-(phenylamino)-1,4,4a,5,5a,6-hexahydrocyclopropa[f]indol-2-yl]pyridin-2-ylacetamide (19-1; 134 mg, 346 μmol) were separated by preparative HPLC (chiral method) to give the title compound (28 mg, 20%).

$^1$H NMR (400 MHz, $CD_2Cl_2$), δ [ppm] 0.95 (1H), 1.18 (1H), 1.37 (3H), 1.67 (1H), 2.21 (3H), 3.00 (1H), 3.23 (1H), 6.68 (2H), 6.78 (1H), 7.02 (1H), 7.10 (2H), 7.23 (1H), 7.98 (1H), 8.19 (1H), 8.23 (1H), 9.37 (1H)

Example 21

3-(Phenylamino)-2-(pyridin-4-yl)cyclohepta[b]pyrrol-4(1H)-one

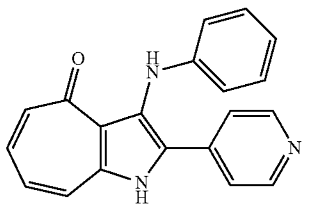 [SMILES: O=c1ccccc2[nH]c(-c3ccncc3)c(Nc3ccccc3)c12]

A mixture of [(6RS)-3-anilino-4-oxo-2-(pyridin-4-yl)-4,5,6,7-tetrahydro-1H-indol-6-yl]methyl methanesulfonate (12-1; 50 mg, 122 μmol), sodium methanolate (33 mg, 608 μmol) in THF (2 mL) was stirred at 50° C. for 16 h. The mixture was concentrated and purified by preparative HPLC (basic method) and preparative TLC (MeOH:DCM) to give the title compound (12 mg, 31%).

$^1$H NMR (400 MHz, DMSO-$d_6$), δ [ppm] 6.54 (2H), 6.68-6.76 (2H), 6.83 (1H), 7.05 (2H), 7.15 (1H), 7.58 (1H), 7.63 (2H), 8.51 (2H), 8.68 (1H), 12.69 (1H)

Example 22

3-(Phenylamino)-2-(pyridin-4-yl)-5,6,7,8-tetrahydrocyclohepta[b]pyrrol-4(1H)-one

22-1: 3-Anilino-2-(pyridin-4-yl)-5,6-dihydrocyclohepta[b]pyrrol-4(1H)-one

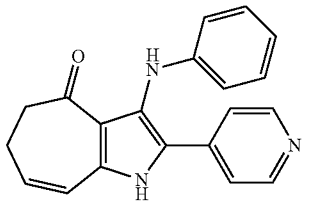 [SMILES: O=C1CCC=Cc2[nH]c(-c3ccncc3)c(Nc3ccccc3)c21]

A mixture of [(6RS)-3-anilino-4-oxo-2-(pyridin-4-yl)-4,5,6,7-tetrahydro-1H-indol-6-yl]methyl methanesulfonate (12-1; 100 mg, 244 μmol), sodium methanolate (225 μL, 5.4 M in degassed MeOH) was stirred at 50° C. for 16 h under a n inert atmosphere of argon. The mixture was concentrated and the residue (121 mg) used without purification in the next step.

3-(Phenylamino)-2-(pyridin-4-yl)-5,6,7,8-tetrahydrocyclohepta[b]pyrrol-4(1H)-one

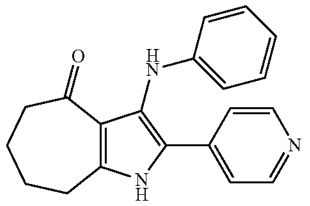 [SMILES: O=C1CCCCc2[nH]c(-c3ccncc3)c(Nc3ccccc3)c21]

To a solution of 3-anilino-2-(pyridin-4-yl)-5,6-dihydrocyclohepta[b]pyrrol-4(1H)-one (22-1; 77 mg crude material) in EtOH (5 mL) and THF (5 mL) was added Pd/C (26 mg, 10%) and the mixture was stirred under an atmosphere of hydrogen at RT for 2 days. DCM was added, the mixture filtered, concentrated and purified by preparative TLC (MeOH:DCM) to give the title compound (2 mg, 3%).

$^1$H NMR (400 MHz, DMSO-$d_6$), δ [ppm] 1.80 (2H), 1.88 (2H), 2.56 (2H), 3.03 (2H), 6.57 (2H), 6.66 (1H), 7.04 (2H), 7.43 (2H), 7.91 (1H), 8.37 (2H), 11.76 (1H)

Example 23

2-(2-Aminopyridin-4-yl)-7-methyl-3-(phenylamino)cyclohepta[b]pyrrol-4(1H)-one

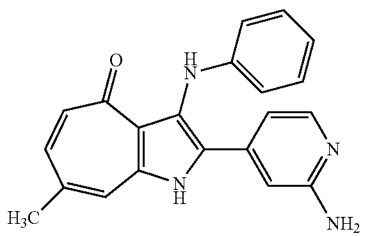 [SMILES: Cc1ccc(=O)c2c(Nc3ccccc3)c(-c3ccnc(N)c3)[nH]c2c1]

A mixture of [(6RS)-2-(2-acetamidopyridin-4-yl)-3-anilino-6-methyl-4-oxo-4,5,6,7-tetrahydro-1H-indol-6-yl]methyl methanesulfonate (19-2; 220 mg, 456 μmol), sodium methanolate (422 μL, 5.4 M in degassed MeOH) in THF (10 mL) was stirred at 50° C. for 16 h under an inert atmosphere of argon. One half of this mixture was concentrated and purified by preparative HPLC (basic method) and preparative TLC (MeOH:DCM) to give the title compound (5 mg, 7%).

$^1$H NMR (400 MHz, DMSO-$d_6$), δ [ppm] 2.35 (3H), 5.87 (2H), 6.61 (2H), 6.66 (1H), 6.69 (1H), 6.73 (1H), 6.82 (1H), 7.02-7.07 (3H), 7.43 (1H), 7.84 (1H), 8.51 (1H), 12.34 (1H)

Example 24

(7RS)-2-(2-Aminopyridin-4-yl)-7-methyl-3-(phenylamino)-5,6,7,8-tetrahydrocyclohepta[b]pyrrol-4(1H)-one

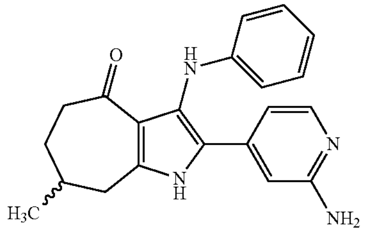 [SMILES: CC1CCC(=O)c2c([nH]c(-c3ccnc(N)c3)c2Nc2ccccc2)C1]

To one half of the reaction mixture prepared in 23 containing 2-(2-aminopyridin-4-yl)-7-methyl-3-(phenylamino)cyclohepta[b]pyrrol-4(1H)-one was added MeOH (7 mL) and Pd/C (65 mg, 10%). The mixture was stirred under an atmosphere of hydrogen at RT for 4 days. After filtration and concentration the residue was preparative HPLC (basic method) and preparative TLC (MeOH:DCM) to give the title compound (5 mg, 6%).

$^1$H NMR (400 MHz, DMSO-$d_6$), δ [ppm] 1.01 (3H), 1.43 (1H), 1.88 (1H), 2.10 (1H), 2.45-2.58 (2H), 2.73 (1H), 3.06 (1H), 5.74 (2H), 6.52-6.58 (3H), 6.63 (1H), 6.67 (1H), 7.02 (2H), 7.70 (1H), 7.73 (1H), 11.56 (1H)

Example 25

N-{4-[(7RS)-3-Anilino-7-methyl-4-oxo-1,4,5,6,7,8-hexahydrocyclohepta[b]pyrrol-2-yl]pyridin-2-yl}acetamide

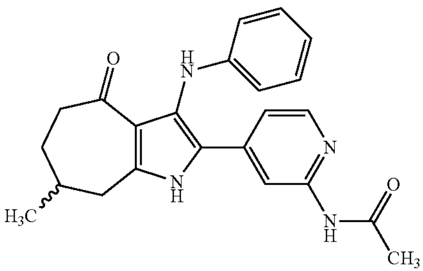 [SMILES: CC(=O)Nc1cc(-c2[nH]c3c(c2Nc2ccccc2)C(=O)CCC(C)C3)ccn1]

A mixture of (7RS)-2-(2-aminopyridin-4-yl)-7-methyl-3-(phenylamino)-5,6,7,8-tetrahydrocyclohepta[b]pyrrol-4(1H)-one (24; 24 mg, 69 μmol), acetyl chloride (7 μL, 104 mmol) in THF (1.8 mL) and pyridine (48 μL) was stirred at RT for 1 h. MeOH was added, the mixture concentrated and purified by preparative TLC (MeOH:DCM) to give the title compound (7 mg, 17%).

$^1$H NMR (400 MHz, DMSO-$d_6$), δ [ppm] 1.02 (3H), 1.44 (1H), 1.89 (1H), 2.06 (3H), 2.11 (1H), 2.47-2.61 (2H), 2.76 (1H), 3.10 (1H), 6.55 (2H), 6.62 (1H), 7.01 (2H), 7.10 (1H), 7.82 (1H), 8.04 (1H), 8.19 (1H), 10.31 (1H), 11.76 (1H)

Example 26 rel-(4aR,5aR)-2-(2-Aminopyridin-4-yl)-3-anilino-5a-methyl-4a,5,5a,6-tetrahydrocyclopropa[f]indol-4(1H)-one 26-2: (6RS)-2-(2-aminopyridin-4-yl)-3-anilino-6-(hydroxymethyl)-6-methyl-1,5,6,7-tetrahydro-4H-indol-4-one

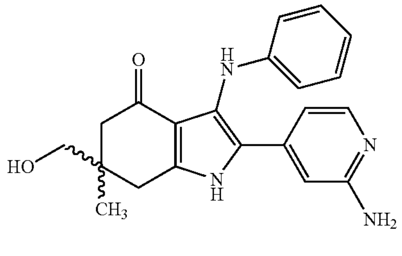

A mixture of (6RS)-2-(2-aminopyridin-4-yl)-3-anilino-6-({[tert-butyl(diphenyl)silyl]oxy}methyl)-6-methyl-1,5,6,7-tetrahydro-4H-indol-4-one (19-5; 1.50 g, 2.50 mmol) and TBAF (6.2 mL, 1M in THF) in THF (35 mL) was stirred at 50° C. for 16 h. EtOAc (100 mL) was added, the mixture washed with sodium hydroxide (2.5% in water), brine and dried over sodium sulfate. After filtration and removal of the solvent the residue was purified by Biotage (SNAP silica 50 g, MeOH:DCM) to give the title compound (540 mg, 57%).

26-1: [(6RS)-2-(2-Aminopyridin-4-yl)-3-anilino-6-methyl-4-oxo-4,5,6,7-tetrahydro-1H-indol-6-yl] methyl methanesulfonate

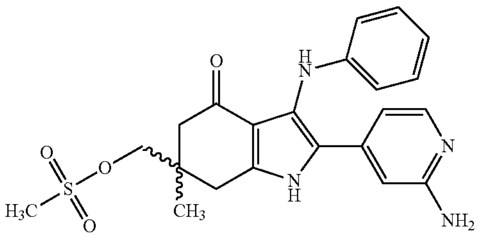

A mixture of (6RS)-2-(2-aminopyridin-4-yl)-3-anilino-6-(hydroxymethyl)-6-methyl-1,5,6,7-tetrahydro-4H-indol-4-one (26-2; 505 mg, 1.39 mmol), methanesulfonyl chloride (162 μL, 2.09 mmol), DMAP (34 mg, 279 μmol) in pyridine (8 mL) was stirred at RT for 4 h. MeOH was added, the mixture concentrated and purified by Biotage (SNAP silica 25 g, MeOH:DCM) to give the title compound (533 mg, 87%).

rel-(4aR,5aR)-2-(2-Aminopyridin-4-yl)-3-anilino-5a-methyl-4a,5,5a,6-tetrahydrocyclopropa[f]indol-4(1H)-one

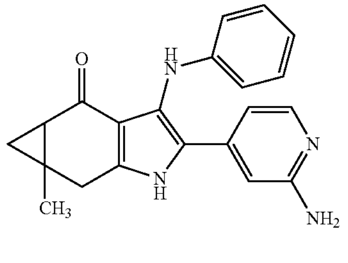 [SMILES: CC12Cc3[nH]c(-c4ccnc(N)c4)c(Nc4ccccc4)c3C(=O)C1C2]

A solution of [(6RS)-2-(2-aminopyridin-4-yl)-3-anilino-6-methyl-4-oxo-4,5,6,7-tetrahydro-1H-indol-6-yl]methyl methanesulfonate (26-1; 2.80 g, 6.36 mmol) in DMA (70 mL) was heated at 140° C. for 3 h. The mixture was concentrated and purified by Biotage (SNAP silica 340 g, MeOH:DCM) to give the title compound (1.13 g, 52%).

$^1$H NMR (400 MHz, DMSO-$d_6$), δ [ppm] 0.77 (1H), 1.11 (1H), 1.29 (3H), 1.51 (1H), 2.97 (1H), 3.19 (1H), 6.01 (2H), 6.53 (2H), 6.57-6.63 (2H), 6.73 (1H), 7.02 (2H), 7.27 (1H), 7.75 (1H), 11.67 (1H)

Example 27

N-{4-[rel-(4aR,5aR)-3-Anilino-5a-methyl-4-oxo-1,4,4a,5,5a,6-hexahydrocyclopropa[f]indol-2-yl]pyridin-2-yl}methanesulfonamide 27-1: [(6RS)-3-Anilino-6-methyl-2-{2-[(methylsulfonyl)amino]pyridin-4-yl}-4-oxo-4,5,6,7-tetrahydro-1H-indol-6-yl]methyl methanesulfonate

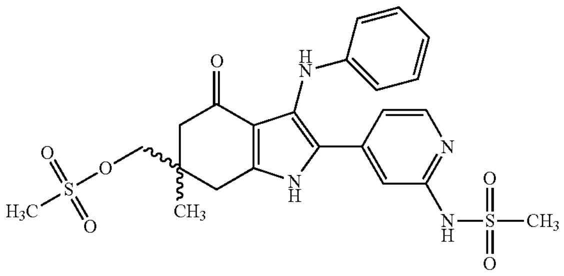

A mixture of (6RS)-2-(2-aminopyridin-4-yl)-3-anilino-6-(hydroxymethyl)-6-methyl-1,5,6,7-tetrahydro-4H-indol-4-one (26-2; 6.70 g, 18.5 mmol), methanesulfonyl chloride (2.15 mL, 27.7 mmol), DMAP (452 mg, 3.70 mmol) in pyridine (100 mL) was stirred at RT for 4 h. MeOH was added, the mixture concentrated and purified by Biotage (SNAP silica 340 g, MeOH:DCM) to give the title compound (873 mg, 9%).

N-{4-[rel-(4aR,5aR)-3-Anilino-5a-methyl-4-oxo-1,4,4a,5,5a,6-hexahydrocyclopropa[f]indol-2-yl]pyridin-2-yl}methanesulfonamide

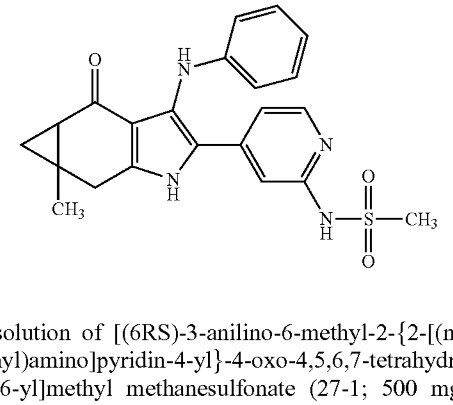

A solution of [(6RS)-3-anilino-6-methyl-2-{2-[(methylsulfonyl)amino]pyridin-4-yl}-4-oxo-4,5,6,7-tetrahydro-1H-indol-6-yl]methyl methanesulfonate (27-1; 500 mg, 964 mmol) in DMA (10 mL) was heated at 140° C. for 4 h. The mixture was concentrated and purified by Biotage (SNAP silica 25 g, MeOH:DCM) to give the title compound (48 mg, 12%).

$^1$H NMR (400 MHz, DMSO-$d_6$), δ [ppm] 0.80 (1H), 1.13 (1H), 1.31 (3H), 1.54 (1H), 2.90 (3H), 3.01 (1H), 3.23 (1H), 6.55 (2H), 6.36 (1H), 7.01-7.10 (3H), 7.14 (1H), 7.44 (1H), 7.94 (1H), 11.11 (1H), 11.85 (1H)

Example 28

N-[4-(3-Anilino-7-methyl-4-oxo-1,4-dihydrocyclohepta[b]pyrrol-2-yl)pyridin-2-yl]methanesulfonamide

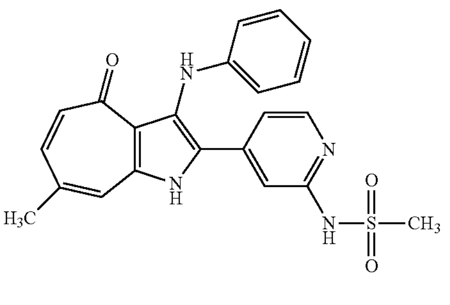

A mixture of N-{4-[rel-(4aR,5aR)-3-Anilino-5a-methyl-4-oxo-1,4,4a,5,5a,6-hexahydrocyclopropa[f]indol-2-yl]pyridin-2-yl}methanesulfonamide (27; 350 mg, 828 μmol), sodium methanolate (767 μL, 5.4 M in MeOH) in THF (17 mL) was stirred at RT for 16 h. The mixture was concentrated and purified by preparative HPLC (basic method) and crystallization from MeOH/DCM to give the title compound (25 mg, 7%).

$^1$H NMR (400 MHz, DMSO-$d_6$), δ [ppm] 2.35 (3H), 2.94 (3H), 6.63 (2H), 6.67 (1H), 6.71 (1H), 7.02-7.11 (3H), 7.25 (1H), 7.30 (1H), 7.42 (1H), 8.12 (1H), 8.71 (1H), 10.99 (1H), 12.48 (1H)

Example 29

1-Fluoro-N-4-[rel-(4aS,5aR)-5a-methyl-4,6-dioxo-3-(phenylamino)-1,4,4a,5,5a,6-hexahydrocyclopropa[f]indol-2-yl]pyridin-2-ylcyclopropanecarboxamide

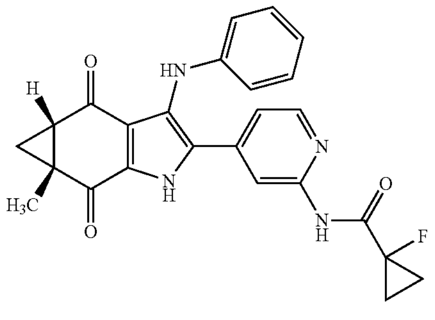 [SMILES: C[C@@]12C[C@@H]1C(=O)c1c([nH]c(-c3ccnc(NC(=O)C4(F)CC4)c3)c1Nc1ccccc1)C2=O]

A solution of 1-fluorocyclopropanecarboxylic acid (91 mg, 871 μmol) and HATU (331 mg, 871 μmol) in DMA (3 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 100 mg, 290 μmol) and DIPEA (152 μL, 871 μmol) in DMA (3 mL) and stirred for 16 h at 50° C. under an atmosphere of air. The mixture was concentrated, DCM added and washed with water and dried over sodium sulfate. After filtration and concentration the residue was purified by Biotage (SNAP NH 28 g, EtOH: DCM) to give the title compound (16 mg, 12%).

$^1$H-NMR (400 MHz, DMSO-$d_6$), δ [ppm]=1.25-1.34 (2H), 1.38 (3H), 1.39-1.44 (1H), 1.44-1.49 (1H), 1.55-1.60

(1H), 1.83 (1H), 2.31 (1H), 6.54 (2H), 6.60 (1H), 7.00 (2H), 7.42 (1H), 7.49 (1H), 8.25 (1H), 8.32 (1H), 10.21 (1H), 13.08 (1H)

Example 30

1-Fluoro-N-4-[[(4aS,5aS) or (4aR,5aR)]-5a-methyl-4-oxo-3-(phenylamino)-1,4,4a,5,5a,6-hexahydrocyclopropa[f]indol-2-yl]pyridin-2-ylcyclopropanecarboxamide 30-1:1-Fluoro-N-4-[rel-(4aS,5aS)-5a-methyl-4-oxo-3-(phenylamino)-1,4,4a,5,5a,6-hexahydrocyclopropa[f]indol-2-yl]pyridin-2-ylcyclopropanecarboxamide

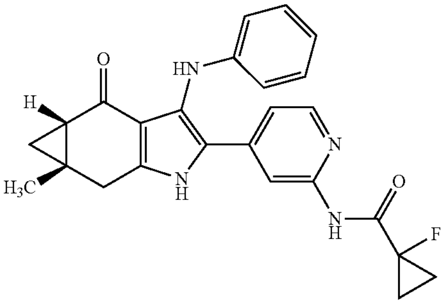

A solution of 1-fluorocyclopropanecarboxylic acid (91 mg, 871 μmol) and HATU (331 mg, 871 μmol) in DMA (3 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 100 mg, 290 μmol) and DIPEA (152 μL, 871 μmol) in DMA (3 mL) and stirred for 16 h at 50° C. under an atmosphere of air. The mixture was concentrated, DCM added and washed with water and dried over sodium sulfate. After filtration and concentration the residue was purified by Biotage (SNAP NH 28 g, EtOH: DCM) to give the title compound (34 mg, 27%).

1-Fluoro-N-4-[[(4aS,5aS) or (4aR,5aR)]-5a-methyl-4-oxo-3-(phenylamino)-1,4,4a,5,5a,6-hexahydrocyclopropa[f]indol-2-yl]pyridin-2-ylcyclopropanecarboxamide

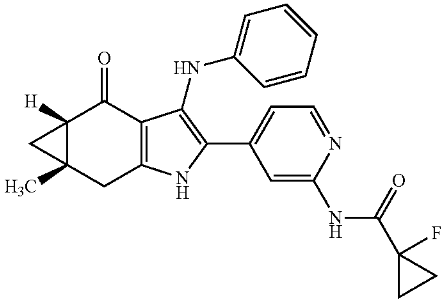

or

-continued

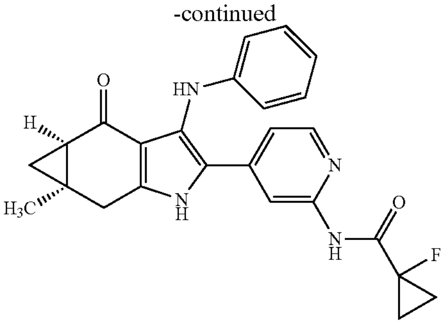

1-Fluoro-N-4-[rel-(4aS,5aS)-5a-methyl-4-oxo-3-(phenylamino)-1,4,4a,5,5a,6-hexahydrocyclopropa[f]indol-2-yl]pyridin-2-ylcyclopropanecarboxamide (30-1; 33 mg, 77 μmol) were separated by preparative HPLC (chiral method) to give the title compound (9 mg, 26%).

$^1$H-NMR (400 MHz, DMSO-d$_6$), δ [ppm]=0.79 (1H), 1.12 (1H), 1.26-1.35 (2H), 1.30 (3H), 1.39-1.49 (2H), 1.52 (1H), 2.98 (1H), 3.22 (1H), 6.52 (2H), 6.60 (1H), 7.01 (2H), 7.25 (1H), 7.37 (1H), 8.09 (1H), 8.14 (1H), 10.09 (1H), 11.84 (1H)

Example 31

1-Fluoro-N-4-[[(4aR,5aR) or (4aS,5aS)]-5a-methyl-4-oxo-3-(phenylamino)-1,4,4a,5,5a,6-hexahydrocyclopropa[f]indol-2-yl]pyridin-2-ylcyclopropanecarboxamide

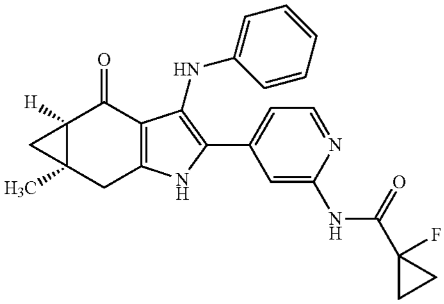

or

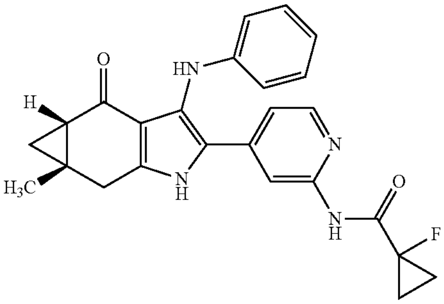 [SMILES: C[C@]12Cc3[nH]c(-c4ccnc(NC(=O)C5(F)CC5)c4)c(Nc4ccccc4)c3C(=O)[C@H]1C2]

1-Fluoro-N-4-[rel-(4aS,5aS)-5a-methyl-4-oxo-3-(phenylamino)-1,4,4a,5,5a,6-hexahydrocyclopropa[f]indol-2-yl]pyridin-2-ylcyclopropanecarboxamide (30-1; 33 mg, 77 μmol) were separated by preparative HPLC (chiral method) to give the title compound (10 mg, 30%).

$^1$H-NMR (400 MHz, DMSO-d$_6$), δ [ppm]=0.79 (1H), 1.12 (1H), 1.26-1.35 (2H), 1.30 (3H), 1.39-1.49 (2H), 1.52

(1H), 2.98 (1H), 3.22 (1H), 6.52 (2H), 6.60 (1H), 7.01 (2H), 7.25 (1H), 7.37 (1H), 8.09 (1H), 8.14 (1H), 10.09 (1H), 11.84 (1H)

Example 32

N-4-[rel-(4aS,5aR)-5a-Methyl-4,6-dioxo-3-(phenylamino)-1,4,4a,5,5a,6-hexahydrocyclopropa[f]indol-2-yl]pyridin-2-ylcyclopropanecarboxamide

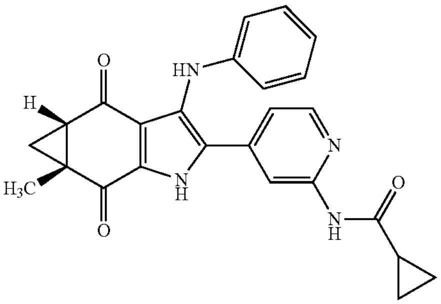 [SMILES: C[C@@]12C[C@@H]1C(=O)c1c([nH]c(-c3ccnc(NC(=O)C4CC4)c3)c1Nc1ccccc1)C2=O]

A solution of cyclopropanecarboxylic acid (75 mg, 871 μmol) and HATU (331 mg, 871 μmol) in DMA (3 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 100 mg, 290 μmol) and DIPEA (152 μL, 871 μmol) in DMA (3 mL) and stirred for 16 h at 50° C. under an atmosphere of air. The mixture was concentrated, DCM added and washed with water and dried over sodium sulfate. After filtration and concentration the residue was purified by Biotage (SNAP NH 28 g, EtOH:DCM) to give the title compound (34 mg, 27%).

$^1$H-NMR (500 MHz, DMSO-d$_6$), δ [ppm]=0.80 (4H), 1.38 (3H), 1.57 (1H), 1.81 (1H), 1.98 (1H), 2.31 (1H), 6.52 (2H), 6.59 (1H), 6.99 (2H), 7.28 (1H), 7.44 (1H), 8.17 (1H), 8.39 (1H), 10.72 (1H), 13.06 (1H)

Example 33

N-{4-[rel-(4aR,5aS)-3-Anilino-5a-methyl-4,6-dioxo-1,4,4a,5,5a,6-hexahydrocyclopropa[f]indol-2-yl]pyridin-2-yl}-1-methylcyclopropanecarboxamide

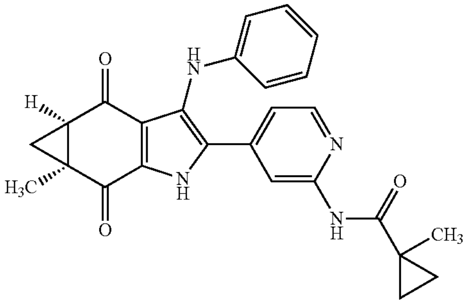 [SMILES: CC1(C(=O)Nc2cc(-c3[nH]c4c(c3Nc3ccccc3)C(=O)[C@@H]3C[C@]3(C)C4=O)ccn2)CC1]

A solution of 1-methyl-cyclopropanecarboxylic acid (87 mg, 871 μmol) and HATU (331 mg, 871 μmol) in DMA (3 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 100 mg, 290 μmol) and DIPEA (152 μL, 871 μmol) in DMA (3 mL) and stirred for 16 h at 50° C. under an atmosphere of air. The mixture was concentrated, DCM added and washed with water and dried over sodium sulfate. After filtration and concentration the residue was purified by Biotage (SNAP NH 28 g, EtOH: DCM) to give the title compound (11 mg, 8%).

$^1$H-NMR (400 MHz, DMSO-$d_6$), δ [ppm]=0.66 (2H), 1.10 (2H), 1.38 (3H), 1.40 (3H), 1.57 (1H), 1.81 (1H), 2.30 (1H), 6.53 (2H), 6.59 (1H), 7.00 (2H), 7.33 (1H), 7.46 (1H), 8.19 (1H), 8.33 (1H), 9.47 (1H), 13.05 (1H)

Example 34

1-Methyl-N-4-[rel-(4aS,5aR)-5a-methyl-4,6-dioxo-3-(phenylamino)-1,4,4a,5,5a,6-hexahydrocyclopropa[f]indol-2-yl]pyridin-2-yl-1H-pyrazole-3-carboxamide

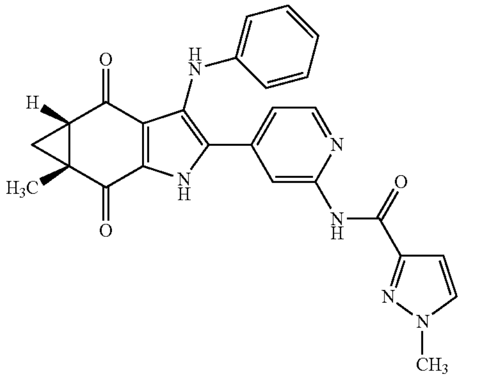 [SMILES: Cn1ccc(C(=O)Nc2cc(-c3[nH]c4c(c3Nc3ccccc3)C(=O)[C@H]3C[C@@]3(C)C4=O)ccn2)n1]

A solution of 1-methyl-1H-pyrazole-3-carboxylic acid (110 mg, 871 μmol) and HATU (331 mg, 871 μmol) in DMA (3 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 100 mg, 290 μmol) and DIPEA (152 μL, 871 μmol) in DMA (3 mL) and stirred for 16 h at 50° C. under an atmosphere of air. The mixture was concentrated, DCM added and washed with water and dried over sodium sulfate. After filtration and concentration the residue was purified by Biotage (SNAP NH 28 g, EtOH:DCM) to give the title compound (27 mg, 19%).

$^1$H-NMR (400 MHz, DMSO-$d_6$), δ [ppm]=1.39 (3H), 1.58 (1H), 1.85 (1H), 2.32 (1H), 3.96 (3H), 6.53-6.61 (3H), 6.85 (1H), 7.00 (2H), 7.38 (1H), 7.50 (1H), 7.88 (1H), 8.23 (1H), 8.52 (1H), 9.51 (1H), 13.13 (1H)

Example 35

4-Fluoro-3-methoxy-N-4-[rel-(4aS,5aR)-5a-methyl-4,6-dioxo-3-(phenylamino)-1,4,4a,5,5a,6-hexahydrocyclopropa[f]indol-2-yl]pyridin-2-ylbenzamide

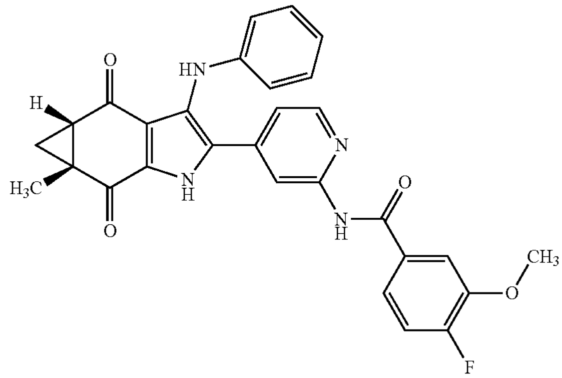 [SMILES: COc1cc(C(=O)Nc2cc(-c3[nH]c4c(c3Nc3ccccc3)C(=O)[C@H]3C[C@@]3(C)C4=O)ccn2)ccc1F]

A solution of 4-fluoro-3-methoxybenzoic acid (148 mg, 871 μmol) and HATU (331 mg, 871 μmol) in DMA (3 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 100 mg, 290 μmol) and DIPEA (152 μL, 871 μmol) in DMA (3 mL) and stirred for 16 h at 50° C. under an atmosphere of air. The mixture was concentrated, DCM added and washed with water and dried over sodium sulfate. After filtration and concentration the residue was purified by Biotage (SNAP NH 28 g, EtOH: DCM) to give the title compound (22 mg, 14%).

$^1$H-NMR (400 MHz, DMSO-$d_6$), δ [ppm]=1.39 (3H), 1.58 (1H), 1.84 (1H), 2.30-2.34 (1H), 3.94 (3H), 6.56 (2H), 6.59 (1H), 7.01 (2H), 7.35 (1H), 7.41 (1H), 7.51 (1H), 7.63 (1H), 7.84 (1H), 8.28 (1H), 8.54 (1H), 10.85 (1H), 13.11 (1H)

Example 36

(1S,2S)-2-Fluoro-N-4-[[(4aS,5aS) or (4aR,5aR)]-5a-methyl-4-oxo-3-(phenylamino)-1,4,4a,5,5a,6-hexahydrocyclopropa[f]indol-2-yl]pyridin-2-ylcyclopropanecarboxamide 36-1: (1S,2S)-2-Fluoro-N-4-[rel-(4aS,5aS)-5a-methyl-4-oxo-3-(phenylamino)-1,4,4a,5,5a,6-hexahydrocyclopropa[f]indol-2-yl]pyridin-2-ylcyclopropanecarboxamide

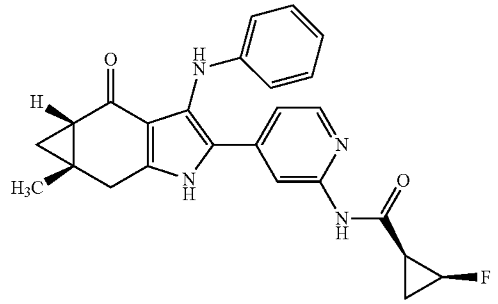 [SMILES: C[C@]12Cc3[nH]c(-c4ccnc(NC(=O)[C@@H]5C[C@@H]5F)c4)c(Nc4ccccc4)c3C(=O)[C@H]1C2]

A solution of (1S,2S)-2-fluorocyclopropanecarboxylic acid (91 mg, 871 μmol) and HATU (331 mg, 871 μmol) in DMA (3 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 100 mg, 290 μmol) and DIPEA (152 μL, 871 μmol) in DMA (3 mL) and stirred for 16 h at 50° C. The mixture was concentrated, DCM added an d washed with water and dried over sodium sulfate. After filtration and concentration the residue was purified by Biotage (SNAP NH 28 g, EtOH:DCM) to give the title compound (84 mg, 67%).

(1S,2S)-2-Fluoro-N-4-[[(4aS,5aS) or (4aR,5aR)]-5a-methyl-4-oxo-3-(phenylamino)-1,4,4a,5,5a,6-hexahydrocyclopropa[f]indol-2-yl]pyridin-2-ylcyclopropanecarboxamide

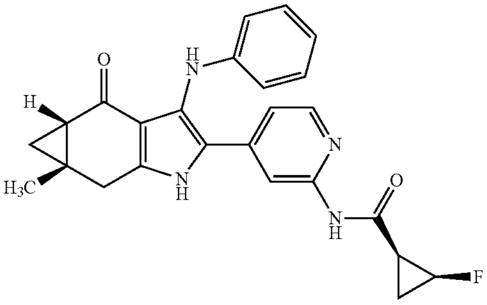

or

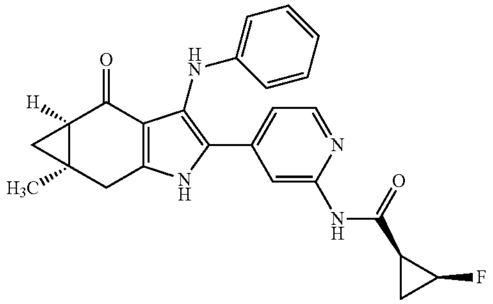

(1S,2S)-2-Fluoro-N-4-[rel-(4aS,5aS)-5a-methyl-4-oxo-3-(phenylamino)-1,4,4a,5,5a,6-hexahydrocyclopropa[f]indol-2-yl]pyridin-2-ylcyclopropanecarboxamide (36-1; 84 mg, 195 μmol) were separated by preparative HPLC (chiral method) to give the title compound (24 mg, 18%).

$^1$H-NMR (400 MHz, DMSO-d$_6$), δ [ppm]=0.79 (1H), 1.07-1.21 (2H), 1.30 (3H), 1.51 (1H), 1.61+1.66 (1H), 2.20 (1H), 2.96 (1H), 3.23 (1H), 4.85+5.01 (1H), 6.52 (2H), 6.59 (1H), 7.00 (2H), 7.16 (1H), 7.34 (1H), 8.07 (1H), 8.23 (1H), 10.71 (1H), 11.85 (1H)

Example 37

(1S,2S)-2-Fluoro-N-4-[[(4aR,5aR) or (4aS,5aS)]-5a-methyl-4-oxo-3-(phenylamino)-1,4,4a,5,5a,6-hexahydrocyclopropa[f]indol-2-yl]pyridin-2-ylcyclopropanecarboxamide

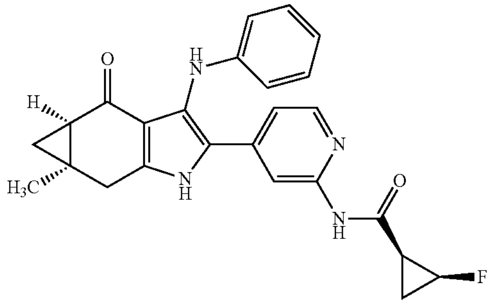

or

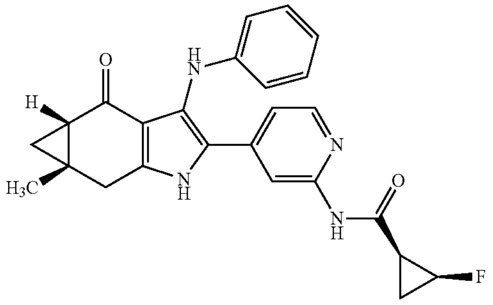

(1S,2S)-2-Fluoro-N-4-[rel-(4aS,5aS)-5a-methyl-4-oxo-3-(phenylamino)-1,4,4a,5,5a,6-hexahydrocyclopropa[f]indol-2-yl]pyridin-2-ylcyclopropanecarboxamide (36-1; 84 mg, 195 μmol) were separated by preparative HPLC (chiral method) to give the title compound (23 mg, 17%).

$^1$H-NMR (400 MHz, DMSO-d$_6$), δ [ppm]=0.78 (1H), 0.78 (1H), 1.09-1.21 (2H), 1.30 (3H), 1.52 (1H), 1.60+1.66 (1H), 2.19 (1H), 2.97 (1H), 3.23 (1H), 4.84+5.01 (1H), 6.52 (2H), 6.59 (1H), 7.01 (2H), 7.17 (1H), 7.34 (1H), 8.08 (1H), 8.23 (1H), 10.71 (1H), 11.84 (1H)

Example 38

N-4-[[(7S) or (7R)]-7-Methyl-4-oxo-3-(phenylamino)-1,4,5,6,7,8-hexahydrocyclohepta[b]pyrrol-2-yl]pyridin-2-ylacetamide 38-1: N-4-[(7RS)-7-Methyl-4-oxo-3-(phenylamino)-1,4,5,6,7,8-hexahydrocyclohepta[b]pyrrol-2-yl]pyridin-2-ylacetamide

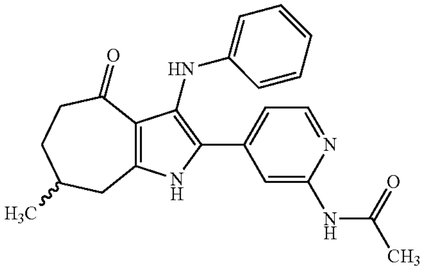

A mixture of (7RS)-2-(2-aminopyridin-4-yl)-7-methyl-3-(phenylamino)-5,6,7,8-tetrahydrocyclohepta[b]pyrrol-4(1H)-one (24; 59 mg, 170 μmol), acetyl chloride (24 μL, 341 μmol), pyridine (237 μL) in THF (4.5 mL) was stirred at RT for 1 h. MeOH was added, the mixture concentrated and purified by preparative TLC (MeOH:DCM) to give the title compound (48 mg, 73%).

N-4-[[(7S) or (7R)]-7-Methyl-4-oxo-3-(phenylamino)-1,4,5,6,7,8-hexahydrocyclohepta[b]pyrrol-2-yl]pyridin-2-ylacetamide

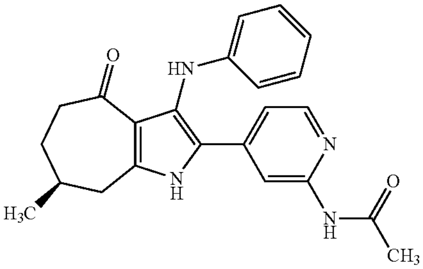

or

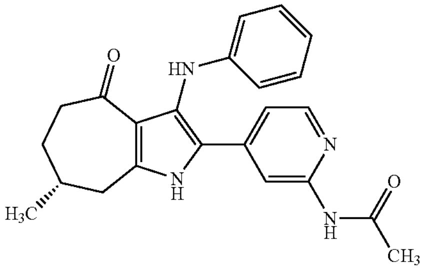

N-4-[(7RS)-7-Methyl-4-oxo-3-(phenylamino)-1,4,5,6,7,8-hexahydrocyclohepta[b]pyrrol-2-yl]pyridin-2-ylacetamide (38-1; 47 mg, 120 μmol) were separated by preparative HPLC (chiral method) to give the title compound (21 mg, 44%).

$^1$H-NMR (400 MHz, DMSO-$d_6$), δ [ppm]=1.01 (3H), 1.43 (1H), 1.89 (1H), 2.05 (3H), 2.11 (1H), 2.54 (2H), 2.76 (1H), 3.09 (1H), 6.54 (2H), 6.62 (1H), 7.00 (2H), 7.09 (1H), 7.82 (1H), 8.03 (1H), 8.18 (1H), 10.30 (1H), 11.75 (1H)

Example 39

N-4-[[(7R) or (7S)]-7-Methyl-4-oxo-3-(phenylamino)-1,4,5,6,7,8-hexahydrocyclohepta[b]pyrrol-2-yl]pyridin-2-ylacetamide

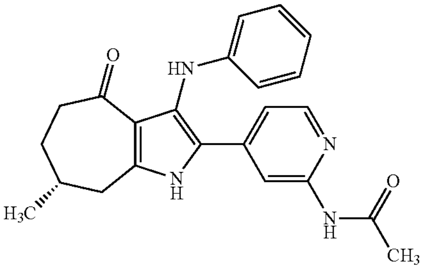 [SMILES: CC(=O)Nc1cc(-c2[nH]c3c(c2Nc2ccccc2)C(=O)CCC(C)C3)ccn1]

or

-continued

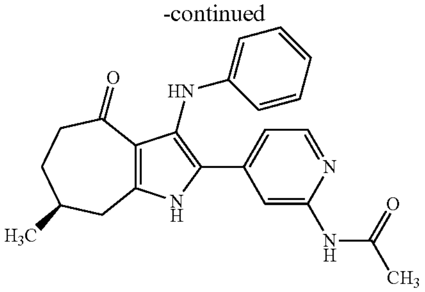

N-4-[(7RS)-7-Methyl-4-oxo-3-(phenylamino)-1,4,5,6,7,8-hexahydrocyclohepta[b]pyrrol-2-yl]pyridin-2-ylacetamide (38-1; 47 mg, 120 μmol) were separated by preparative HPLC (chiral method) to give the title compound (19 mg, 38%).

$^1$H-NMR (400 MHz, DMSO-$d_6$), δ [ppm]=1.01 (3H), 1.43 (1H), 1.89 (1H), 2.05 (3H), 2.11 (1H), 2.54 (2H), 2.76 (1H), 3.09 (1H), 6.54 (2H), 6.62 (1H), 7.00 (2H), 7.09 (1H), 7.82 (1H), 8.03 (1H), 8.18 (1H), 10.30 (1H), 11.75 (1H)

Example 40

2-Fluoro-2-methyl-N-4-[[(4aS,5aS) or (4aR,5aR)]-5a-methyl-4-oxo-3-(phenylamino)-1,4,4a,5,5a,6-hexahydrocyclopropa[f]indol-2-yl]pyridin-2-ylpropanamide 40-1: 2-Fluoro-2-methyl-N-4-[rel-(4aS,5aS)-5a-methyl-4-oxo-3-(phenylamino)-1,4,4a,5,5a,6-hexahydrocyclopropa[f]indol-2-yl]pyridin-2-ylpropanamide

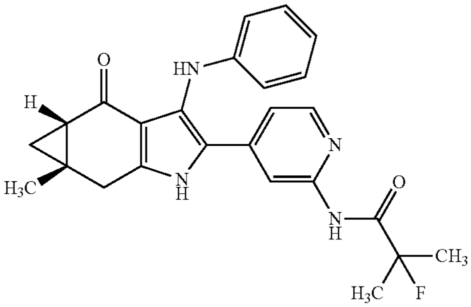

A solution of 2-fluoro-2-methylpropanoic acid (92 mg, 871 μmol) and HATU (331 mg, 871 μmol) in DMA (3 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 100 mg, 290 μmol) and DIPEA (152 μL, 871 μmol) in DMA (3 mL) and stirred for 16 h at 50° C. The mixture was concentrated, DCM added and washed with water and dried over sodium sulfate. After filtration and concentration the residue was purified by Biotage (SNAP NH 28 g, EtOH:DCM) to give the title compound (118 mg, 94%).

2-Fluoro-2-methyl-N-4-[[(4aS,5aS) or (4aR,5aR)]-5a-methyl-4-oxo-3-(phenylamino)-1,4,4a,5,5a,6-hexahydrocyclopropa[f]indol-2-yl]pyridin-2-ylpropanamide

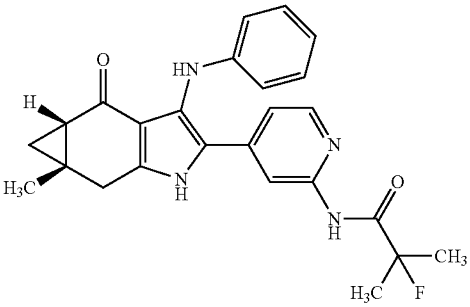 [SMILES: CC(C)(F)C(=O)Nc1cc(-c2[nH]c3c(c2Nc2ccccc2)C(=O)[C@H]2C[C@@]2(C)C3)ccn1]

or

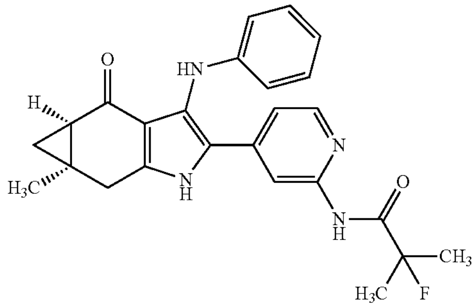

2-Fluoro-2-methyl-N-4-[rel-(4aS,5aS)-5a-methyl-4-oxo-3-(phenylamino)-1,4,4a,5,5a,6-hexahydrocyclopropa[f]indol-2-yl]pyridin-2-ylpropanamide (40-1; 118 mg, 272 μmol) were separated by preparative HPLC (chiral method) to give the title compound (36 mg, 27%).

$^1$H-NMR (400 MHz, DMSO-$d_6$), δ [ppm]=0.79 (1H), 1.12 (1H), 1.30 (3H), 1.52 (1H), 1.54 (3H), 1.60 (3H), 2.98 (1H), 3.22 (1H), 6.52 (2H), 6.59 (1H), 7.00 (2H), 7.23 (1H), 7.38 (1H), 8.11 (1H), 8.12 (1H), 9.70 (1H), 11.86 (1H)

Example 41

2-Fluoro-2-methyl-N-4-[[(4aR,5aR) or (4aS,5aS)]-5a-methyl-4-oxo-3-(phenylamino)-1,4,4a,5,5a,6-hexahydrocyclopropa[f]indol-2-yl]pyridin-2-ylpropanamide

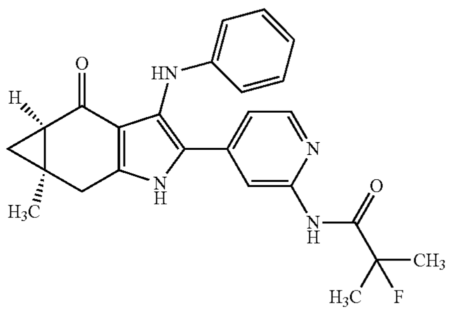

or

-continued

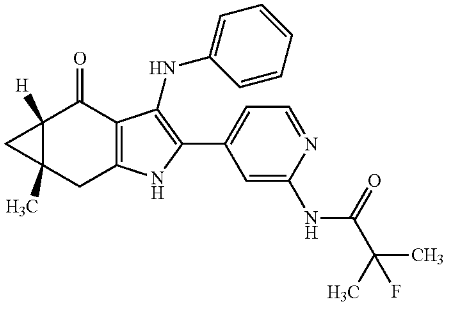

2-Fluoro-2-methyl-N-4-[rel-(4aS,5aS)-5a-methyl-4-oxo-3-(phenylamino)-1,4,4a,5,5a,6-hexahydrocyclopropa[f]indol-2-yl]pyridin-2-ylpropanamide (40-1; 118 mg, 272 μmol) were separated by preparative HPLC (chiral method) to give the title compound (39 mg, 30%).

$^1$H-NMR (400 MHz, DMSO-$d_6$), δ [ppm]=0.79 (1H), 1.12 (1H), 1.30 (3H), 1.52 (1H), 1.54 (3H), 1.60 (3H), 2.98 (1H), 3.22 (1H), 6.52 (2H), 6.59 (1H), 7.00 (2H), 7.23 (1H), 7.38 (1H), 8.11 (1H), 8.12 (1H), 9.70 (1H), 11.86 (1H)

Example 42

1-Methyl-N-4-[[(4aS,5aS) or (4aR,5aR)]-5a-methyl-4-oxo-3-(phenylamino)-1,4,4a,5,5a,6-hexahydrocyclopropa[f]indol-2-yl]pyridin-2-yl-1H-pyrazole-5-carboxamide 42-1: 1-Methyl-N-4-[rel-(4aS,5aS)-5a-methyl-4-oxo-3-(phenylamino)-1,4,4a,5,5a,6-hexahydrocyclopropa[f]indol-2-yl]pyridin-2-yl-1H-pyrazole-5-carboxamide

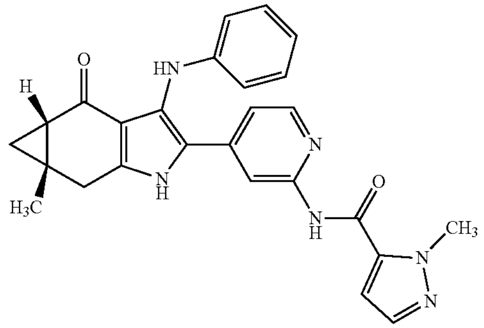

A solution of 1-methyl-1H-pyrazole-5-carboxylic acid (110 mg, 871 μmol) and HATU (331 mg, 871 μmol) in DMA (3 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 100 mg, 290 μmol) and DIPEA (152 μL, 871 μmol) in DMA (3 mL) and stirred for 16 h at 50° C. The mixture was concentrated, DCM added and washed with water and dried over sodium sulfate. After filtration and concentration the residue was purified by Biotage (SNAP NH 28 g, EtOH:DCM) to give the title compound (91 mg, 69%).

1-Methyl-N-4-[[(4aS,5aS) or (4aR,5aR)]-5a-methyl-4-oxo-3-(phenylamino)-1,4,4a,5,5a,6-hexahydrocyclopropa[f]indol-2-yl]pyridin-2-yl-1H-pyrazole-5-carboxamide

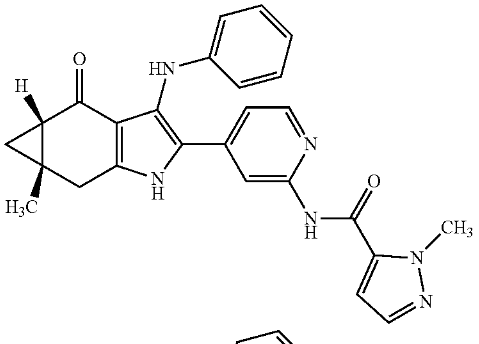

or

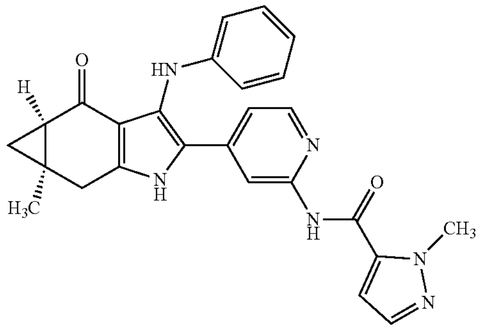

1-Methyl-N-4-[rel-(4aS,5aS)-5a-methyl-4-oxo-3-(phenylamino)-1,4,4a,5,5a,6-hexahydrocyclopropa[f]indol-2-yl]pyridin-2-yl-1H-pyrazole-5-carboxamide (42-1; 91 mg, 201 μmol) were separated by preparative HPLC (chiral method) to give the title compound (31 mg, 22%).

$^1$H-NMR (400 MHz, DMSO-$d_6$), δ [ppm]=0.80 (1H), 1.14 (1H), 1.31 (3H), 1.53 (1H), 3.00 (1H), 3.25 (1H), 4.10 (3H), 6.54 (2H), 6.59 (1H), 7.01 (2H), 7.25 (2H), 7.38 (1H), 7.51 (1H), 8.16 (1H), 8.25 (1H), 10.66 (1H), 11.86 (1H)

Example 43

1-Methyl-N-4-[[(4aR,5aR) or (4aS,5aS)]-5a-methyl-4-oxo-3-(phenylamino)-1,4,4a,5,5a,6-hexahydrocyclopropa[f]indol-2-yl]pyridin-2-yl-1H-pyrazole-5-carboxamide

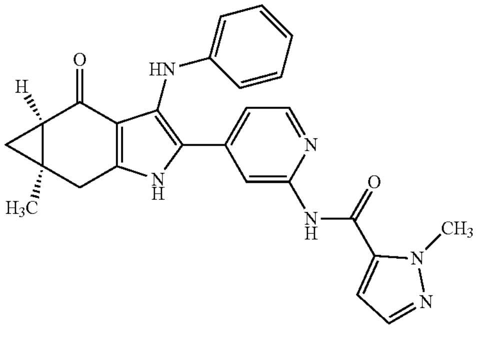

or

-continued

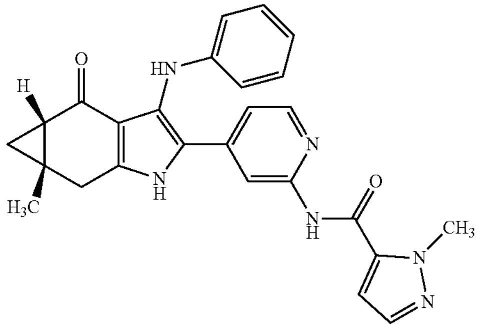 [SMILES: Cn1nccc1C(=O)Nc1cc(-c2[nH]c3c(c2Nc2ccccc2)C(=O)[C@H]2C[C@@]2(C)C3)ccn1]

1-Methyl-N-4-[rel-(4aS,5aS)-5a-methyl-4-oxo-3-(phenylamino)-1,4,4a,5,5a,6-hexahydrocyclopropa[f]indol-2-yl]pyridin-2-yl-1H-pyrazole-5-carboxamide (42-1; 91 mg, 201 μmol) were separated by preparative HPLC (chiral method) to give the title compound (22 mg, 16%).

$^1$H-NMR (400 MHz, DMSO-$d_6$), δ [ppm]=0.80 (1H), 1.14 (1H), 1.31 (3H), 1.53 (1H), 3.00 (1H), 3.25 (1H), 4.10 (3H), 6.54 (2H), 6.59 (1H), 7.01 (2H), 7.25 (2H), 7.38 (1H), 7.51 (1H), 8.16 (1H), 8.25 (1H), 10.66 (1H), 11.86 (1H)

Example 44

N-4-[[(4aS,5aS) or (4aR,5aR)]-5a-Methyl-4-oxo-3-(phenylamino)-1,4,4a,5,5a,6-hexahydrocyclopropa[f]indol-2-yl]pyridin-2-yl-1H-pyrazole-3-carboxamide 44-1: N-4-[rel-(4aS,5aS)-5a-Methyl-4-oxo-3-(phenylamino)-1,4,4a,5,5a,6-hexahydrocyclopropa[f]indol-2-yl]pyridin-2-yl-1H-pyrazole-3-carboxamide

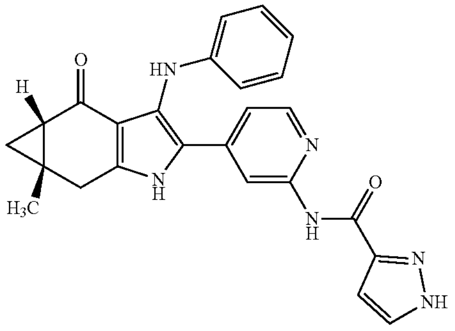 [SMILES: C[C@]12Cc3[nH]c(-c4ccnc(NC(=O)c5cc[nH]n5)c4)c(Nc4ccccc4)c3C(=O)[C@H]1C2]

A solution of 1H-pyrazole-3-carboxylic acid (117 mg, 1.05 mmol) and HATU (397 mg, 1.05 mmol) in DMA (3.6 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 120 mg, 348 μmol) and DIPEA (182 μL, 1.05 mmol) in DMA (3.6 mL) and stirred for 16 h at 50° C. The mixture was concentrated, DCM added and washed with water and dried over sodium sulfate. After filtration and concentration the residue was purified by Biotage (SNAP NH 28 g, EtOH:DCM) to give the title compound (70 mg, 43%).

N-4-[[(4aS,5aS) or (4aR,5aR)]-5a-Methyl-4-oxo-3-(phenylamino)-1,4,4a,5,5a,6-hexahydrocyclopropa[f]indol-2-yl]pyridin-2-yl-1H-pyrazole-3-carboxamide

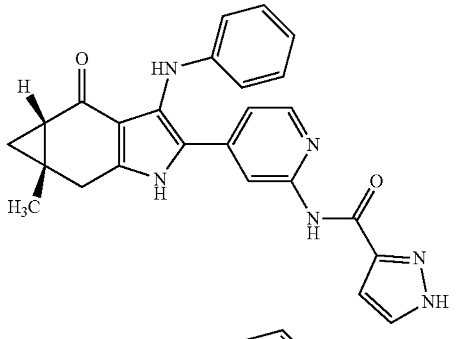

or

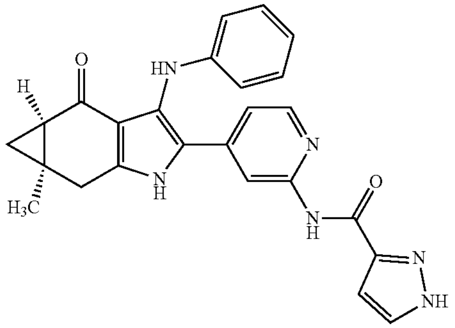

N-4-[rel-(4aS,5aS)-5a-Methyl-4-oxo-3-(phenylamino)-1,4,4a,5,5a,6-hexahydrocyclopropa[f]indol-2-yl]pyridin-2-yl-1H-pyrazole-3-carboxamide (44-1; 70 mg, 159 μmol) were separated by preparative HPLC (chiral method) to give the title compound (25 mg, 36%).

$^1$H-NMR (400 MHz, DMSO-$d_6$), δ [ppm]=0.81 (1H), 1.12 (1H), 1.30 (3H), 1.52 (1H), 2.99 (1H), 3.24 (1H), 6.54 (2H), 6.59 (1H), 6.85 (1H), 7.01 (2H), 7.23 (1H), 7.37 (1H), 7.93 (1H), 8.13 (1H), 8.33 (1H), 9.48 (1H), 11.89 (1H), 13.52 (1H)

Example 45

N-4-[[(4aR,5aR) or (4aS,5aS)]-5a-Methyl-4-oxo-3-(phenylamino)-1,4,4a,5,5a,6-hexahydrocyclopropa[f]indol-2-yl]pyridin-2-yl-1H-pyrazole-3-carboxamide

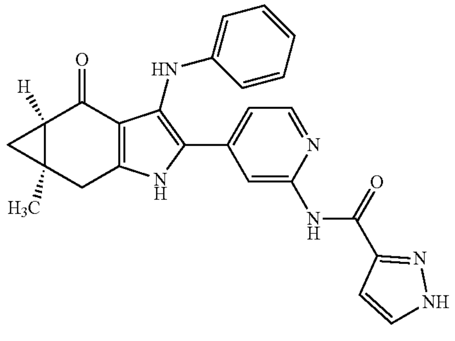

or

-continued

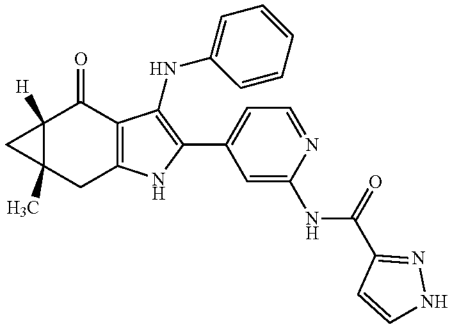

N-4-[rel-(4aS,5aS)-5a-Methyl-4-oxo-3-(phenylamino)-1,4,4a,5,5a,6-hexahydrocyclopropa[f]indol-2-yl]pyridin-2-yl-1H-pyrazole-3-carboxamide (44-1; 70 mg, 159 μmol) were separated by preparative HPLC (chiral method) to give the title compound (28 mg, 38%).

$^1$H-NMR (400 MHz, DMSO-$d_6$), δ [ppm]=0.81 (1H), 1.12 (1H), 1.30 (3H), 1.52 (1H), 2.99 (1H), 3.24 (1H), 6.54 (2H), 6.59 (1H), 6.85 (1H), 7.01 (2H), 7.23 (1H), 7.37 (1H), 7.93 (1H), 8.13 (1H), 8.33 (1H), 9.48 (1H), 11.89 (1H), 13.52 (1H)

Example 46

N-{4-[[(4aR,5aR) or (4aS,5aS)]-3-Anilino-5a-methyl-4-oxo-1,4,4a,5,5a,6-hexahydrocyclopropa[f]indol-2-yl]pyridin-2-yl}-2,6-difluorobenzamide

46-1: N-{4-[rel-(4aR,5aR)-3-Anilino-5a-methyl-4-oxo-1,4,4a,5,5a,6-hexahydrocyclopropa[f]indol-2-yl]pyridin-2-yl}-2,6-difluorobenzamide

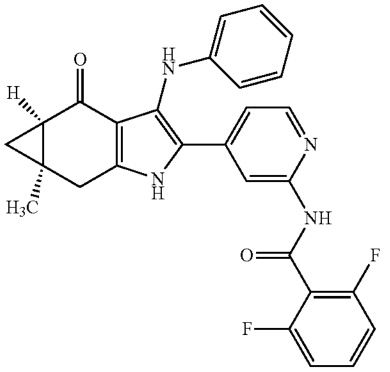 [SMILES: C[C@@]12Cc3[nH]c(-c4ccnc(NC(=O)c5c(F)cccc5F)c4)c(Nc4ccccc4)c3C(=O)[C@@H]1C2]

A mixture of rel-(4aR,5aR)-2-(2-Aminopyridin-4-yl)-3-anilino-5a-methyl-4a,5,5a,6-tetrahydrocyclopropa[f]indol-4(1H)-one (26; 120 mg, 348 μmol), 2,6-difluorobenzoyl chloride (57 μL, 453 μmol) in pyridine (5.0 mL) was stirred at RT for 16 h. MeOH was added, the mixture concentrated and purified by Biotage (SNAP 50 g, MeOH:DCM) to give the title compound (104 mg, 55%).

N-{4-[[(4aR,5aR) or (4aS,5aS)]-3-anilino-5a-methyl-4-oxo-1,4,4a,5,5a,6-hexahydrocyclopropa[f]indol-2-yl]pyridin-2-yl}-2,6-difluorobenzamide

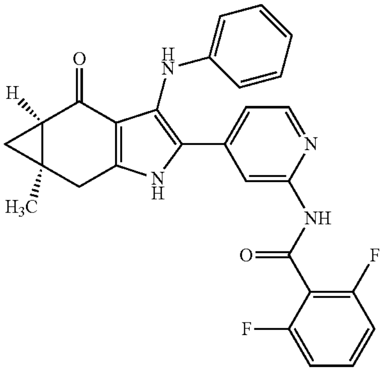

or

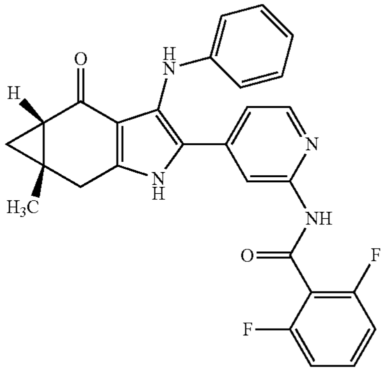

N-{4-[rel-(4aR,5aR)-3-Anilino-5a-methyl-4-oxo-1,4,4a,5,5a,6-hexahydrocyclopropa[f]indol-2-yl]pyridin-2-yl}-2,6-difluorobenzamide (46-1; 102 mg, 211 μmol) were separated by preparative HPLC (chiral method) to give the title compound (20 mg, 20%).

$^1$H-NMR (400 MHz, CHLOROFORM-d), δ [ppm]=0.95 (1H), 1.17 (1H), 1.36 (3H), 1.69 (1H), 2.95 (1H), 3.20 (1H), 6.67 (2H), 6.78 (1H), 6.90 (1H), 6.95 (2H), 7.11 (2H), 7.37 (1H), 7.42 (1H), 7.70 (1H), 8.37 (1H), 8.93 (1H), 9.18 (1H)

Example 47

N-{4-[[(4aS,5aS) or (4aR,5aR)]-3-anilino-5a-methyl-4-oxo-1,4,4a,5,5a,6-hexahydrocyclopropa[f]indol-2-yl]pyridin-2-yl}-2,6-difluorobenzamide

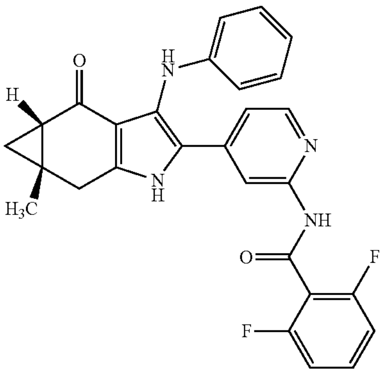

or

-continued

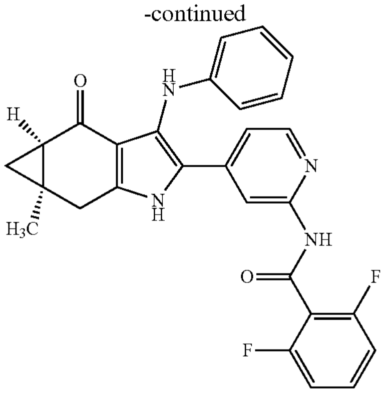

N-{4-[rel-(4aR,5aR)-3-Anilino-5a-methyl-4-oxo-1,4,4a,5,5a,6-hexahydrocyclopropa[f]indol-2-yl]pyridin-2-yl}-2,6-difluorobenzamide (46-1; 102 mg, 211 μmol) were separated by preparative HPLC (chiral method) to give the title compound (17 mg, 16%).

$^1$H-NMR (400 MHz, CHLOROFORM-d), δ [ppm]=0.95 (1H), 1.17 (1H), 1.36 (3H), 1.69 (1H), 2.95 (1H), 3.20 (1H), 6.67 (2H), 6.78 (1H), 6.90 (1H), 6.95 (2H), 7.11 (2H), 7.37 (1H), 7.42 (1H), 7.70 (1H), 8.37 (1H), 8.93 (1H), 9.18 (1H)

Example 48

N-{4-[[(4aR,5aR) or (4aS,5aS)]-3-anilino-5a-methyl-4-oxo-1,4,4a,5,5a,6-hexahydrocyclopropa[f]indol-2-yl]pyridin-2-yl}-4-fluoro-2-methylbenzamide 48-1: N-{4-[rel-(4aR,5aR)-3-anilino-5a-methyl-4-oxo-1,4,4a,5,5a,6-hexahydrocyclopropa[f]indol-2-yl]pyridin-2-yl}-4-fluoro-2-methylbenzamide

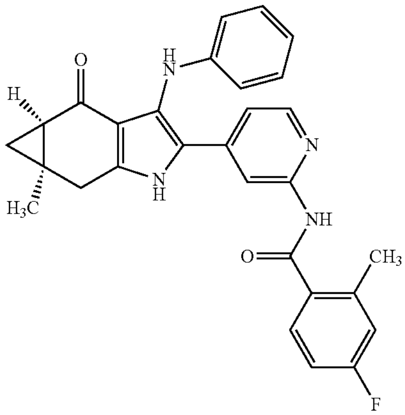

A solution of 4-fluoro-2-methylbenzoic acid (280 mg, 1.82 mmol) and HATU (690 mg, 1.82 mmol) in DMA (6 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 250 mg, 726 μmol) and DIPEA (316 μL, 1.82 mmol) in DMA (6 mL) and stirred for 16 h at 50° C. The mixture was concentrated and purified by Biotage (SNAP NH 55 g, EtOH:DCM) to give the title compound (135 mg, 39%).

N-{4-[[(4aR,5aR) or (4aS,5aS)]-3-anilino-5a-methyl-4-oxo-1,4,4a,5,5a,6-hexahydrocyclopropa[f]indol-2-yl]pyridin-2-yl}-4-fluoro-2-methylbenzamide

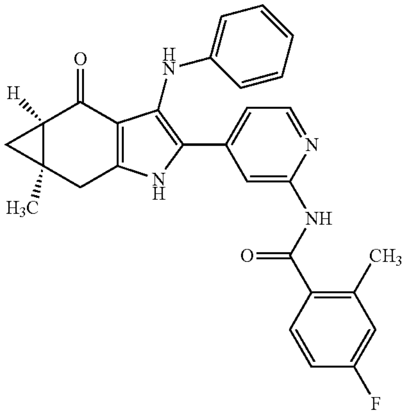 [SMILES: Cc1cc(F)ccc1C(=O)Nc1cc(-c2[nH]c3c(c2Nc2ccccc2)C(=O)[C@@H]2C[C@]2(C)C3)ccn1]

or

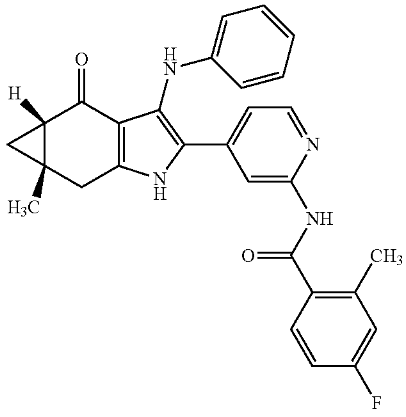

N-{4-[rel-(4aR,5aR)-3-anilino-5a-methyl-4-oxo-1,4,4a,5,5a,6-hexahydrocyclopropa[f]indol-2-yl]pyridin-2-yl}-4-fluoro-2-methylbenzamide (48-1; 135 mg, 281 μmol) were separated by preparative HPLC (chiral method) to give the title compound (61 mg, 42%).

$^1$H-NMR (400 MHz, DMSO-d6), δ [ppm]=0.80 (1H), 1.13 (1H), 1.30 (3H), 1.53 (1H), 2.37 (3H), 2.99 (1H), 3.24 (1H), 6.54 (2H), 6.60 (1H), 7.01 (2H), 7.09 (1H), 7.15 (1H), 7.23 (1H), 7.38 (1H), 7.48 (1H), 8.12 (1H), 8.26 (1H), 10.62 (1H), 11.86 (1H).

Example 49

N-{4-[[(4aS,5aS) or (4aR,5aR)]-3-anilino-5a-methyl-4-oxo-1,4,4a,5,5a,6-hexahydrocyclopropa[f]indol-2-yl]pyridin-2-yl}-4-fluoro-2-methylbenzamide

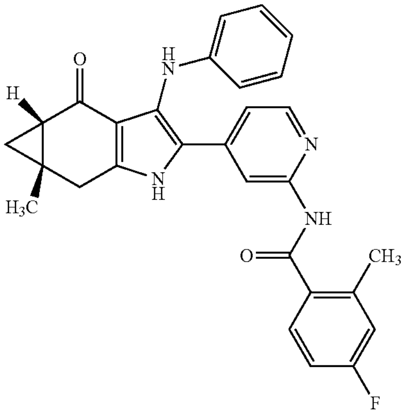

or

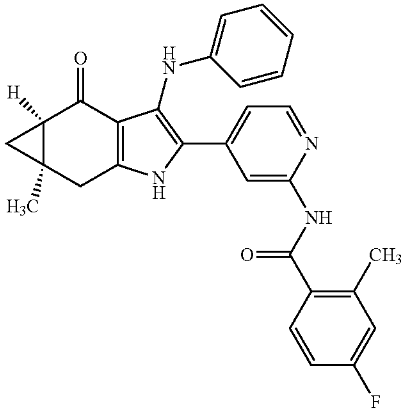

N-{4-[rel-(4aR,5aR)-3-anilino-5a-methyl-4-oxo-1,4,4a,5,5a,6-hexahydrocyclopropa[f]indol-2-yl]pyridin-2-yl}-4-fluoro-2-methylbenzamide (48-1; 135 mg, 281 μmol) were separated by preparative HPLC (chiral method) to give the title compound (68 mg, 49%).

$^1$H-NMR (400 MHz, DMSO-d6), δ [ppm]=0.80 (1H), 1.13 (1H), 1.30 (3H), 1.53 (1H), 2.37 (3H), 2.99 (1H), 3.24 (1H), 6.54 (2H), 6.60 (1H), 7.01 (2H), 7.09 (1H), 7.15 (1H), 7.23 (1H), 7.38 (1H), 7.48 (1H), 8.12 (1H), 8.26 (1H), 10.62 (1H), 11.86 (1H).

Example 50

N-{4-[[(4aR,5aR) or (4aS,5aS)]-3-anilino-5a-methyl-4-oxo-1,4,4a,5,5a,6-hexahydrocyclopropa[f]indol-2-yl]pyridin-2-yl}-3-fluoro-4-methoxybenzamide 50-1 : N-{4-[rel-(4aR,5aR)-3-anilino-5a-methyl-4-oxo-1,4,4a,5,5a,6-hexahydrocyclopropa[f]indol-2-yl]pyridin-2-yl}-3-fluoro-4-methoxybenzamide

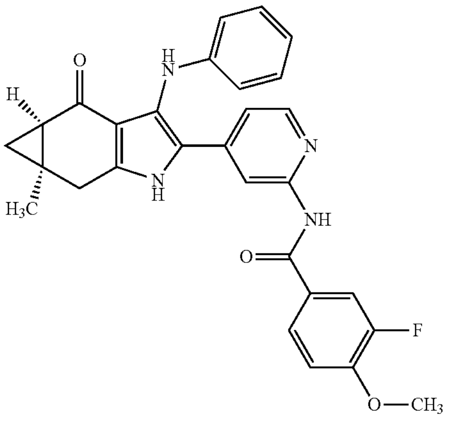 [SMILES: COc1ccc(C(=O)Nc2cc(-c3[nH]c4c(c3Nc3ccccc3)C(=O)[C@@H]3C[C@]3(C)C4)ccn2)cc1F]

A solution of 45-fluoro-4-methoxycyclohexa-1,4-diene-1-carboxylic acid (247 mg, 1.45 mmol) and HATU (552 mg, 1.45 mmol) in DMA (5 mL) was added to a mixture of rel-(4aR,5aR)-2-(2-Aminopyridin-4-yl)-3-anilino-5a-methyl-4a,5,5a,6-tetrahydrocyclopropa[f]indol-4(1H)-one (26; 200 mg, 581 μmol) and DIPEA (354 μL, 1.45 mmol) in DMA (5 mL) and stirred for 16 h at 50° C. The mixture was concentrated and purified by Biotage (SNAP 50 g, EtOH: DCM) to give the title compound (99 mg, 33%).

N-{4-[(4aR,5aR)-3-anilino-5a-methyl-4-oxo-1,4,4a,5,5a,6-hexahydrocyclopropa[f]indol-2-yl]pyridin-2-yl}-3-fluoro-4-methoxybenzamide

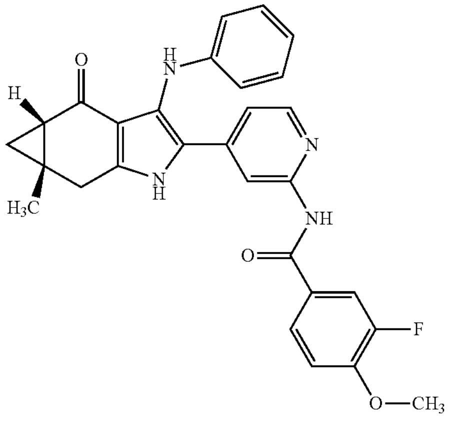

or

-continued

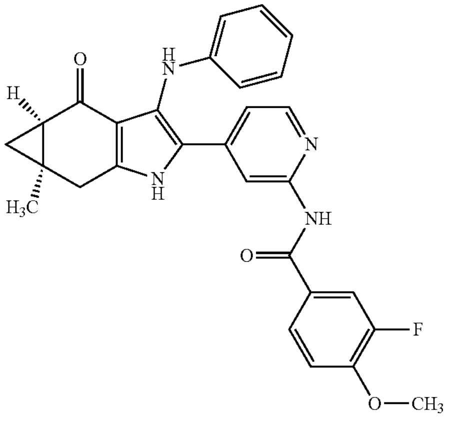

N-{4-[rel-(4aR,5aR)-3-anilino-5a-methyl-4-oxo-1,4,4a,5,5a,6-hexahydrocyclopropa[f]indol-2-yl]pyridin-2-yl}-3-fluoro-4-methoxybenzamide (50-1; 95 mg, 191 μmol) were separated by preparative HPLC (chiral method) to give the title compound (23 mg, 23%).

$^1$H-NMR (400 MHz, DMSO-d6), δ [ppm]=0.80 (1H), 1.12 (1H), 1.30 (3H), 1.52 (1H), 2.99 (1H), 3.24 (1H), 3.92 (3H), 6.54 (2H), 6.59 (1H), 7.01 (2H), 7.23 (1H), 7.30 (1H), 7.37 (1H), 7.89-7.95 (2H), 8.15 (1H), 8.29 (1H), 10.62 (1H), 11.86 (1H).

Example 51

N-{4-[[(4aS,5aS) or (4aR,5aR)]-3-anilino-5a-methyl-4-oxo-1,4,4a,5,5a,6-hexahydrocyclopropa[f]indol-2-yl]pyridin-2-yl}-3-fluoro-4-methoxybenzamide

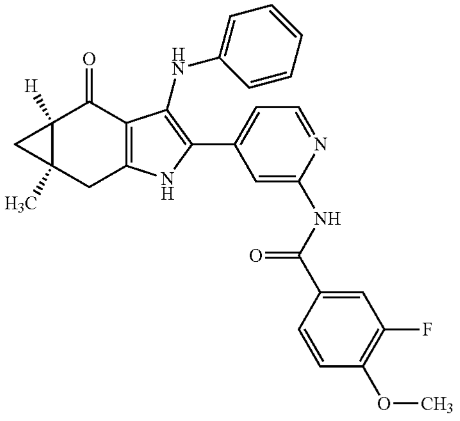

or

-continued

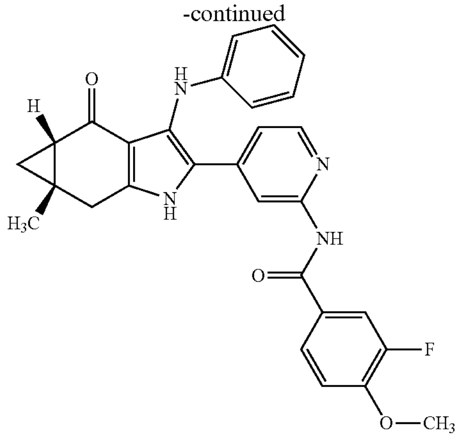

N-{4-[rel-(4aR,5aR)-3-anilino-5a-methyl-4-oxo-1,4,4a,5,5a,6-hexahydrocyclopropa[f]indol-2-yl]pyridin-2-yl}-3-fluoro-4-methoxybenzamide (50-1; 95 mg, 191 μmol) were separated by preparative HPLC (chiral method) to give the title compound (29 mg, 29%).

$^1$H-NMR (400 MHz, DMSO-d6), δ [ppm]=0.80 (1H), 1.12 (1H), 1.30 (3H), 1.52 (1H), 2.99 (1H), 3.24 (1H), 3.92 (3H), 6.54 (2H), 6.59 (1H), 7.01 (2H), 7.23 (1H), 7.30 (1H), 7.37 (1H), 7.89-7.95 (2H), 8.15 (1H), 8.29 (1H), 10.62 (1H), 11.86 (1H).

Biological Investigations

The following assays can be used to illustrate the commercial utility of the compounds according to the present invention.

Examples were tested in selected biological assays one or more times. When tested more than once, data are reported as either average values or as median values, wherein the average value, also referred to as the arithmetic mean value, represents the sum of the values obtained divided by the number of times tested and the median value represents the middle number of the group of values when ranked in ascending or descending order. If the number of values in the data set is odd, the median is the middle value. If the number of values in the data set is even, the median is the arithmetic mean of the two middle values.

Examples were synthesized one or more times. When synthesized more than once, data from biological assays represent average values calculated utilizing data sets obtained from testing of one or more synthetic batch.

Bub1 Kinase Assay

Bub1-inhibitory activities of compounds described in the present invention were quantified using a time-resolved fluorescence energy transfer (TR-FRET) kinase assay which measures phosphorylation of the synthetic peptide Biotin-Ahx-VLLPKKSFAEPG (SEQ ID No. 1) (C-terminus in amide form), purchased from e.g. Biosyntan (Berlin, Germany) by the (recombinant) catalytic domain of human Bub1 (amino acids 704-1085), expressed in Hi5 insect cells with an N-terminal His6-tag and purified by affinity-(Ni-NTA) and size exclusion chromatography.

In a typical assay 11 different concentrations of each compound (0.1 nM, 0.33 nM, 1.1 nM, 3.8 nM, 13 nM, 44 nM, 0.15 μM, 0.51 μM, 1.7 μM, 5.9 μM and 20 μM) were tested in duplicate within the same microtiter plate. To this end, 100-fold concentrated compound solutions (in DMSO) were previously prepared by serial dilution (1:3.4) of 2 mM stocks in a clear low volume 384-well source microtiter plate (Greiner Bio-One, Frickenhausen, Germany), from which 50 nl of compounds were transferred into a black low volume test microtiter plate from the same supplier. Subsequently, 2 μL of Bub1 (the final concentration of Bub1 was adjusted depending on the activity of the enzyme lot in order to be within the linear dynamic range of the assay: typically ~200 ng/mL were used) in aqueous assay buffer [50 mM Tris/HCl pH 7.5, 10 mM magnesium chloride ($MgCl_2$), 200 mM potassium chloride (KCl), 1.0 mM dithiothreitol (DTT), 0.1 mM sodium ortho-vanadate, 1% (v/v) glycerol, 0.01% (w/v) bovine serum albumine (BSA), 0.005% (v/v) Trition X-100 (Sigma), 1× Complete EDTA-free protease inhibitor mixture (Roche)] were added to the compounds in the test plate and the mixture was incubated for 15 min at 22° C. to allow pre-equilibration of the putative enzyme-inhibitor complexes before the start of the kinase reaction, which was initiated by the addition of 3 μL 1.67-fold concentrated solution (in assay buffer) of adenosine-tri-phosphate (ATP, 10 μM final concentration) and peptide substrate (1 μM final concentration). The resulting mixture (5 μL final volume) was incubated at 22° C. during 60 min. and the reaction w as stopped by the addition of 5 μL of an aqueous EDTA-solution (50 mM EDTA, in 100 mM HEPES pH 7.5 and 0.2% (w/v) bovine serum albumin) which also contained the TR-FRET detection reagents (0.2 μM streptavidin-XL665 [Cisbio Bioassays, Codolet, France] and 1 nM anti-phosho-Serine antibody [Merck Millipore, cat. #35-002] and 0.4 nM LANCE EU-W1024 labeled anti-mouse IgG antibody [Perkin-Elmer, product no. AD0077, alternatively a Terbium-cryptate-labeled anti-mouse IgG antibody from Cisbio Bioassays can be used]). The stopped reaction mixture was further incubated 1 h at 22° C. in order to allow the formation of complexes between peptides and detection reagents. Subsequently, the amount of product was evaluated by measurement of the resonance energy transfer from the Eu-chelate-antibody complex recognizing the Phosphoserine residue to the streptavidin-XL665 bound to the biotin moiety of the peptide. To this end, the fluorescence emissions at 620 nm and 665 nm after excitation at 330-350 nm were measured in a TR-FRET plate reader, e.g. a Rubystar or Pherastar (both from BMG Labtechnologies, Offenburg, Germany) or a Viewlux (Perkin-Elmer) and the ratio of the emissions (665 nm/622 nm) was taken as indicator for the amount of phosphorylated substrate. The data were normalised using two sets of control wells for high-(=enzyme reaction without inhibitor=0%=Minimum inhibition) and low-(=all assay components without enzyme=100%=Maximum inhibition) Bub1 activity. IC50 values were calculated by fitting the normalized inhibition data to a 4-parameter logistic equation (Minimum, Maximum, IC50, Hill; Y=Max+(Min−Max)/(1+(X/IC50)Hill)).

TABLE 1

Inhibition of Bub1 kinase

| Example Nr. | $IC_{50}$ [nM] |
|---|---|
| 1 | 146 |
| 2 | 1160 |
| 3 | 648 |
| 4 | 2930 |
| 5 | 115 |
| 6 | 63 |
| 7 | 68 |
| 8 | 375 |
| 9 | 240 |
| 10 | 35 |
| 11 | 19 |

TABLE 1-continued

| Inhibition of Bub1 kinase | |
|---|---|
| Example Nr. | $IC_{50}$ [nM] |
| 12 | 7 |
| 13 | 19 |
| 14 | 4 |
| 15 | 6 |
| 16 | 6 |
| 17 | 5 |
| 18 | 6 |
| 19 | 8 |
| 20 | 36 |
| 21 | 8 |
| 22 | 6 |
| 23 | 26 |
| 24 | 25 |
| 25 | 7 |
| 26 | nd |
| 27 | 630 |
| 28 | nd |
| 29 | 133 |
| 30 | 17 |
| 31 | 52 |
| 32 | 30 |
| 33 | 110 |
| 34 | 35 |
| 35 | 71 |
| 36 | 16 |
| 37 | 11 |
| 38 | 27 |
| 39 | 5 |
| 40 | 22 |
| 41 | 53 |
| 42 | 11 |
| 43 | 22 |
| 44 | 5 |
| 45 | 18 |
| 46 | 4 |
| 47 | 7 |
| 48 | nd |
| 49 | nd |
| 50 | 13 |
| 51 | 12 |

nd: not yet determined

The invention claimed is:

1. A compound of formula (I), (I)

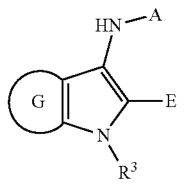

wherein:

G is a group selected from the group consisting of:

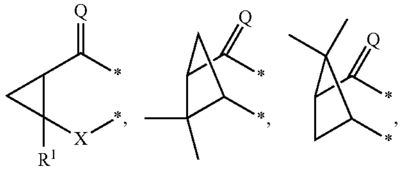

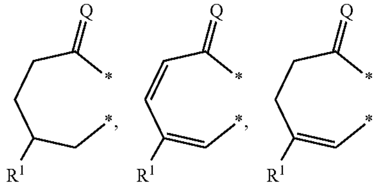

and

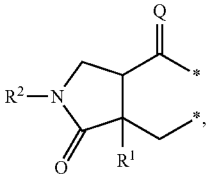

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Valine modified by
Biotin-Aminocaproic acid (Biotin-Ahx-Val)
<220> FEATURE:
<221> NAME/KEY: AMIDATION
<222> LOCATION: 12

<400> SEQUENCE: 1

```
Xaa Leu Leu Pro Lys Lys Ser Phe Ala Glu Pro Gly
1               5                   10
```

wherein * indicates the points of attachment of said group with the rest of the molecule;

X is $CH_2$, $CHOR^x$, or C═O;

$R^x$ is hydrogen or $C_1$-$C_6$-alkyl;

$R^1$ is hydrogen or $C_1$-$C_6$-alkyl;

$R^2$ is hydrogen, $C_1$-$C_6$-alkyl, $R^{10}$—O—C(O)— or $R^7R^8N$—C(O)—;

$R^3$ is hydrogen or $C_1$-$C_6$-alkyl;

A is a group selected from the group consisting of:

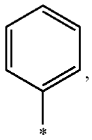, 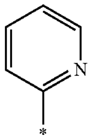 and 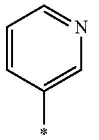

wherein * indicates the point of attachment of said group to the rest of the molecule and said group is optionally substituted, one or more times, independently from each other, with $R^4$;

$R^4$ is halogen, hydroxy, nitro, cyano, $C_1$-$C_4$-alkyl, $C_1$-$C_4$-alkoxy, $C_1$-$C_4$-haloalkyl, $C_1$- $C_4$-haloalkoxy, $C_1$-$C_4$-hydroxyalkyl, $C_1$-$C_4$-alkyl-C(O)—, $R^{10}$—O—C(O)—, $R^7R^8N$—C(O)—, $C_1$-$C_4$-alkyl-C(O)—NH—, $R^7R^8N$—, or $R^7R^8N$—$SO_2$—;

E is a group

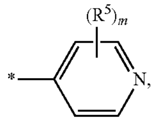

wherein * indicates the point of attachment of said group to the rest of the molecule;

each $R^5$ is independently halogen, hydroxy, nitro, cyano, $R^9R^{10}N$—, ($R^{13}$—C(O)—)($R^{14}$—C(O)—)N—, $C_1$-$C_4$-alkyl, $C_3$-$C_6$-cycloalkyl, $C_1$-$C_6$-alkoxy, $C_1$-$C_4$-haloalkyl, $C_1$-$C_6$-haloalkoxy, $R^6$—C(O)—$NR^9$—, $R^6$—O—C(O)—$NR^9$—, $R^6$—$SO_2$—$NR^9$— or $R^7R^8N$—C(O)—$NR^9$—;

Q is O or N—OH;

each $R^6$ is independently $C_1$-$C_6$-alkyl, $C_3$-$C_6$-cycloalkyl, 4- to 6-membered heterocycloalkyl, phenyl or heteroaryl, wherein said $C_1$-$C_6$-alkyl is optionally substituted, one or more times, independently from each other, with halogen, hydroxy, nitro, cyano, $C_1$-$C_4$-alkoxy, $C_1$-$C_4$-haloalkoxy, $C_3$-$C_6$-cycloalkyl, $R^7R^8N$— or phenyl optionally substituted, one or more times, independently from each other, with $R^4$, wherein said $C_3$-$C_6$-cycloalkyl, 4- to 6-membered heterocycloalkyl, phenyl or heteroaryl groups are optionally substituted, one or more times, independently from each other, with halogen, hydroxy, nitro, cyano, $C_1$-$C_6$-alkyl, $C_1$-$C_4$-alkoxy, $C_1$-$C_4$-haloalkyl, $R^{10}$—O—C(O)— or $C_1$-$C_4$-haloalkoxy;

$R^7$ and $R^8$ are independently hydrogen, $C_1$-$C_6$-alkyl, $C_3$-$C_6$-cycloalkyl, $R^{10}$—O—C(O)— or phenyl, wherein said $C_1$-$C_6$-alkyl is optionally substituted, one or more times, independently from each other, with halogen, hydroxy, $C_1$-$C_4$-alkoxy, $C_1$-$C_4$-haloalkoxy, $C_3$-$C_6$-cycloalkyl optionally substituted one time with hydroxy, 4- to 6-membered heterocycloalkyl, heteroaryl, or $R^9R^{10}N$—, wherein said phenyl group is optionally substituted, one or more times, independently from each other, with $R^4$;

or, $R^7$ and $R^8$ together with the nitrogen atom to which they are attached form a 4- to 7-membered nitrogen containing heterocyclic ring, optionally containing one additional heteroatom selected from the group consisting of O, $NR^9$ and S, and which may be optionally substituted one or more times, independently from each other, with $R^{12}$;

whereby when two $R^{12}$ substituents are attached to the same ring carbon atom, together with the carbon atom to which they are attached, can be linked to one another in such a way that they jointly form a cyclobutane, azetidine, or oxetane group;

said azetidine being optionally substituted one time with $C_1$-$C_3$-alkyl, or, $R^7$ and $R^8$ together with the nitrogen atom to which they are attached form a group selected from:

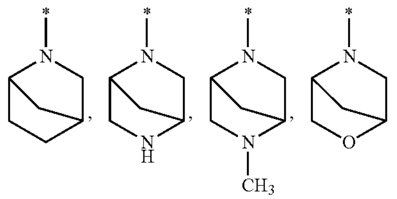

wherein * indicates the point of attachment of said group to the rest of the molecule, $R^9$ is hydrogen, or $C_1$-$C_6$-alkyl;

$R^{10}$ is hydrogen, $C_1$-$C_6$-alkyl or $C_3$-$C_6$-cycloalkyl;

$R^{12}$ is halogen, hydroxy, $C_1$-$C_4$-alkyl, $C_1$-$C_4$-alkoxy, $C_1$-$C_4$-haloalkyl, $C_1$-$C_4$-haloalkoxy, or $R^9R^{10}N$—;

$R^{13}$ and $R^{14}$ are independently $C_1$-$C_4$-alkyl, or $C_3$-$C_6$-cycloalkyl, wherein said $C_3$-$C_6$-cycloalkyl is optionally substituted, one or more times, independently from each other, with halogen; and m is 0, 1 or 2, or an N-oxide, a salt, a tautomer or a stereoisomer of said compound, or a salt of said N-oxide, tautomer or stereoisomer.

2. The compound of formula (I) according to claim 1, wherein:

G is a group selected from the group consisting of:

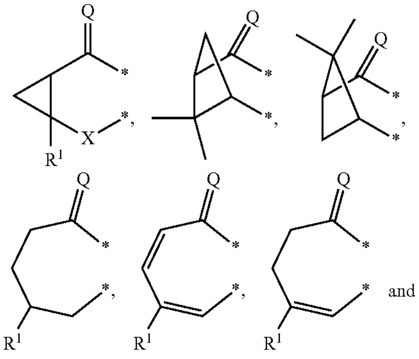 and

-continued

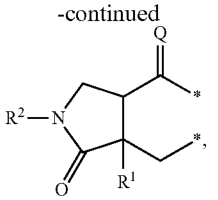

wherein * indicates the points of attachment of said group to the rest of the molecule;

X is $CH_2$ or C═O;

$R^1$ is hydrogen or $C_1$-$C_4$-alkyl;

$R^2$ is hydrogen, $C_1$-$C_4$-alkyl, $R^{10}$—O—C(O)—, or $R^7R^8N$—C(O)—;

$R^3$ is hydrogen or $C_1$-$C_4$-alkyl;

A is a group selected from:

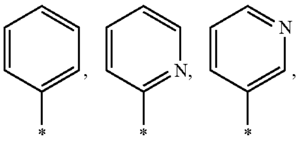

wherein * indicates the point of attachment of said group to the rest of the molecule and said group is optionally substituted, one or more times, independently from each other, with $R^4$;

$R^4$ is halogen, hydroxy, nitro, cyano, $C_1$-$C_4$-alkyl, $C_1$-$C_4$-alkoxy, $C_1$-$C_4$-haloalkyl, $C_1$-$C_4$-haloalkoxy, $C_1$-$C_4$-hydroxyalkyl, $C_1$-$C_4$-alkyl-C(O)—, or $R^{10}$—O—C(O)—;

E is a group

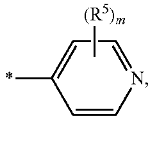

wherein * indicates the point of attachment of said group to the rest of the molecule;

each $R^5$ is independently halogen, hydroxy, nitro, cyano, $R^9R^{10}N$—, ($R^{13}$—C(O)—)($R^{14}$—C(O)—)N—, $C_1$-$C_3$-alkyl, $C_3$-$C_4$-cycloalkyl, $C_1$-$C_3$-alkoxy, $C_1$-$C_3$-haloalkyl, $C_1$-$C_3$-haloalkoxy, $R^6$—C(O)—$NR^9$—, $R^6$—O—C(O)—$NR^9$—, $R^6$—$SO_2$—$NR^9$—, or $R^7R^8N$—C(O)—$NR^9$—, Q is O;

each $R^6$ is independently $C_1$-$C_6$-alkyl, $C_3$-$C_6$-cycloalkyl, 4- to 6-membered heterocycloalkyl, phenyl, or heteroaryl, wherein said $C_1$-$C_6$-alkyl is optionally substituted, one or more times, independently from each other, with halogen, hydroxy, nitro, cyano, $C_1$-$C_4$-alkoxy, $C_1$-$C_4$-haloalkoxy, $C_3$-$C_6$-cycloalkyl, $R^7R^8N$— or phenyl optionally substituted, one or more times, independently from each other, with $R^4$, wherein said $C_3$-$C_6$-cycloalkyl, 4- to 6-membered heterocycloalkyl, phenyl or heteroaryl groups are optionally substituted, one or more times, independently from each other, with halogen, hydroxy, nitro, cyano, $C_1$-$C_6$-alkyl, $C_1$-$C_4$-alkoxy, $C_1$-$C_4$-haloalkyl, $R^{10}$—O—C(O)—, or $C_1$-$C_4$-haloalkoxy;

$R^7$ and $R^8$ are independently hydrogen, $C_1$-$C_6$-alkyl, $C_3$-$C_6$-cycloalkyl, $R^{10}$—O—C(O)—, or phenyl, wherein said $C_1$-$C_6$-alkyl is optionally substituted, one or more times, independently from each other, with halogen, hydroxy, $C_1$-$C_4$-alkoxy, $C_1$-$C_4$-haloalkoxy, $C_3$-$C_6$-cycloalkyl optionally substituted one time with hydroxy, 4- to 6-membered heterocycloalkyl, heteroaryl, or $R^9R^{10}N$—, wherein said phenyl group is optionally substituted, one or more times, independently from each other, with $R^4$;

or, $R^7$ and $R^8$ together with the nitrogen atom to which they are attached form a 5- to 6-membered nitrogen containing heterocyclic ring, optionally containing one additional heteroatom selected from the group consisting of O and $NR^9$;

$R^9$ is hydrogen or $C_1$-$C_4$-alkyl;

$R^{10}$ is hydrogen, $C_1$-$C_4$-alkyl, or $C_3$-$C_4$-cycloalkyl;

$R^{13}$ and $R^{14}$ are independently $C_1$-$C_3$-alkyl, or $C_3$-$C_4$-cycloalkyl, wherein said $C_3$-$C_4$-cycloalkyl is optionally substituted, one or more times, independently from each other, with halogen; and m is 0, 1 or 2, or an N-oxide, a salt, a tautomer or a stereoisomer of said compound, or a salt of said N-oxide, tautomer or stereoisomer.

3. The compound of formula (I) according to claim 1, wherein:

G is a group selected from the group consisting of:

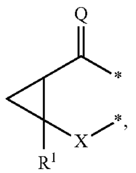
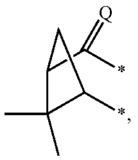
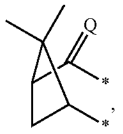
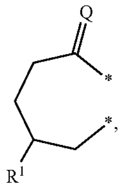
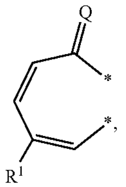
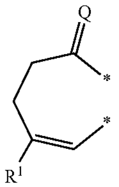
and
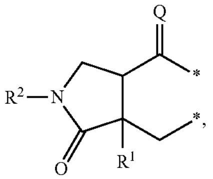

wherein * indicates the points of attachment of said group to the rest of the molecule;

X is $CH_2$ or C═O;

$R^1$ is hydrogen or $C_1$-$C_4$-alkyl;

$R^2$ is hydrogen, or $C_1$-$C_3$-alkyl;

$R^3$ is hydrogen or $C_1$-$C_2$-alkyl;

A is a group selected from:

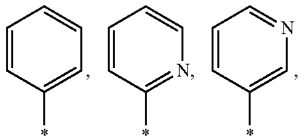

wherein * indicates the point of attachment of said group to the rest of the molecule and said group is optionally substituted, one or more times, independently from each other, with $R^4$;

$R^4$ is halogen, hydroxy, nitro, cyano, $C_1$-$C_2$-alkyl, $C_1$-$C_2$-alkoxy, $C_1$-$C_2$-haloalkyl, $C_1$-$C_2$-haloalkoxy, or $C_1$-$C_2$-hydroxyalkyl;

E is a group

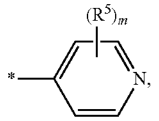

wherein * indicates the point of attachment of said group to the rest of the molecule;

each $R^5$ is independently halogen, hydroxy, nitro, cyano, $R^9R^{10}N$—, $C_1$-alkyl, $C_3$-cycloalkyl, $C_1$-alkoxy, $C_1$-haloalkyl, $C_1$-haloalkoxy, $R^6$—C(O)—$NR^9$—, $R^6$—O—C(O)—$NR^9$—, $R^6$—$SO_2$—$NR^9$— or $R^7R^8N$—C(O)—$NR^9$—;

Q is O;

each $R^6$ is independently $C_1$-$C_4$-alkyl, $C_3$-$C_4$-cycloalkyl, 5- to 6-membered heterocycloalkyl, phenyl, or heteroaryl, wherein said $C_1$-$C_4$-alkyl is optionally substituted, one or more times, independently from each other, with halogen, hydroxy, $C_1$-alkoxy, or $C_1$-haloalkoxy, wherein said $C_3$-$C_4$-cycloalkyl, 5- to 6-membered heterocycloalkyl, phenyl or heteroaryl groups are optionally substituted, one or more times, independently from each other, with halogen, hydroxy, $C_1$-alkyl, $C_1$-alkoxy, or $C_1$-haloalkyl;

$R^7$ and $R^8$ are independently hydrogen, $C_1$-$C_4$-alkyl, or $C_3$-$C_4$-cycloalkyl, wherein said $C_1$-$C_4$-alkyl is optionally substituted, one or more times, independently from each other, with halogen, hydroxy, $C_1$-alkoxy, $C_1$-haloalkoxy, $C_3$-$C_4$-cycloalkyl optionally substituted one time with hydroxy, 5- to 6-membered heterocycloalkyl, heteroaryl, or $R^9R^{10}N$—, $R^9$ is hydrogen or $C_1$-alkyl;

$R^{10}$ is hydrogen or $C_1$-alkyl; and m is 0 or 1, or an N-oxide, a salt, a tautomer or a stereoisomer of said compound, or a salt of said N-oxide, tautomer or stereoisomer.

4. The compound of formula (I) according to claim 1, wherein:

G is a group selected from the group consisting of:

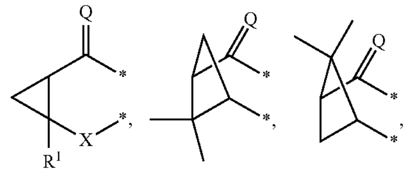

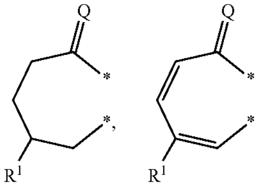

and

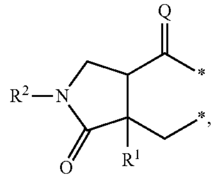

wherein * indicates the points of attachment of said group to the rest of the molecule;

X is $CH_2$ or C═O;

$R^1$ is hydrogen or $C_1$-alkyl;

$R^2$ is $C_1$-alkyl;

$R^3$ is hydrogen;

A is a group:

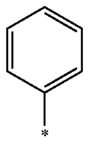

wherein * indicates the point of attachment of said group to the rest of the molecule;

E is a group

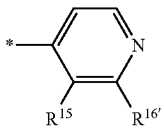

wherein * indicates the point of attachment of said group to the rest of the molecule;

Q is O;

each $R^6$ is independently $C_1$-$C_3$-alkyl, $C_3$-cycloalkyl, phenyl, or heteroaryl, wherein said $C_1$-$C_3$-alkyl is optionally substituted, one or more times, with fluoro, wherein said $C_3$-cycloalkyl, phenyl or heteroaryl groups are optionally substituted, one or two times, independently from each other, with fluoro, $C_1$-alkyl, or $C_1$-alkoxy;

$R^7$ and $R^8$ are independently hydrogen, $C_1$-$C_2$-alkyl, or $C_3$-cycloalkyl;

$R^9$ is hydrogen;

$R^{10}$ is hydrogen;

$R^{15}$ is a hydrogen or a fluorine atom; and $R^{16}$ is hydrogen, $R^9R^{10}N$—, $R^6$—C(O)—$NR^9$—, $R^6$—O—C(O)—$NR^9$—, $R^6$—$SO_2$—$NR^9$—, or $R^7R^8N$—C(O)—$NR^9$—, or an N-oxide, a salt, a tautomer or a stereoisomer of said compound, or a salt of said N-oxide, tautomer or stereoisomer.

5. The compound according to claim 1, which is selected from the group consisting of:

rel-(5R,7S)-6,6-dimethyl-3-(phenylamino)-2-(pyridin-4-yl)-1,5,6,7-tetrahydro-4H-5,7-methanoindol-4-one, rel-(5R,7S)-2-(2-aminopyridin-4-yl)-6,6-dimethyl-3-(phenylamino)-1,5,6,7-tetrahydro-4H-5,7-methanoindol-4-one, (5R,7S)-2-(2-aminopyridin-4-yl)-6,6-dimethyl-3-(phenylamino)-1,5,6,7-tetrahydro-4H-5,7-methanoindol-4-one, (5S,7R)-2-(2-aminopyridin-4-yl)-6,6-dimethyl-3-(phenylamino)-1,5,6,7-tetrahydro-4H-5,7-methanoindol-4-one, N-4-[rel-(5R,7S)-6,6-dimethyl-4-oxo-3-(phenylamino)-4,5,6,7-tetrahydro-1H-5,7-methanoindol-2-yl]pyridin-2-ylacetamide, N-4-[rel-(5R,7S)-6,6-dimethyl-4-oxo-3-(phenylamino)-4,5,6,7-tetrahydro-1H-5,7-methanoindol-2-yl]pyridin-2-ylcyclopropanecarboxamide, methyl 4-[rel-(5R,7S)-6,6-dimethyl-4-oxo-3-(phenylamino)-4,5,6,7-tetrahydro-1H-5,7-methanoindol-2-yl]pyridin-2-ylcarbamate, 1-4-[rel-(5R,7S)-6,6-dimethyl-4-oxo-3-(phenylamino)-4,5,6,7-tetrahydro-1H-5,7-methanoindol-2-yl]pyridin-2-yl-3-ethylurea, 1-cyclopropyl-3-4-[rel-(5R,7S)-6,6-dimethyl-4-oxo-3-(phenylamino)-4,5,6,7-tetrahydro-1H-5,7-methanoindol-2-yl]pyridin-2-ylurea, rel-(5R,7S)-2-(3-fluoropyridin-4-yl)-6,6-dimethyl-3-(phenylamino)-1,5,6,7-tetrahydro-4H-5,7-methanoindol-4-one, rel-(4aR,7aS)-6-methyl-3-(phenylamino)-2-(pyridin-4-yl)-1,4a,5,6,7a,8-hexahydropyrrolo[3,4-f]indole-4,7-dione, rel-(4aR,5aR)-3-(phenylamino)-2-(pyridin-4-yl)-4a,5,5a,6-tetrahydrocyclopropa[f]indol-4(1H)-one, (4aR,5aR)-3-(phenylamino)-2-(pyridin-4-yl)-4a,5,5a,6-tetrahydrocyclopropa[f]indol-4(1H)-one, (4aS,5aS)-3-(phenylamino)-2-(pyridin-4-yl)-4a,5,5a,6-tetrahydrocyclopropa[f]indol-4(1H)-one, rel-(4aR,5aR)-N-4-[4-oxo-3-(phenylamino)-1,4,4a,5,5a,6-hexahydrocyclopropa[f]indol-2-yl]pyridin-2-ylacetamide, rel-(4aR,5aR)-5a-methyl-3-(phenylamino)-2-(pyridin-4-yl)-4a,5,5a,6-tetrahydrocyclopropa[f]indol-4(1H)-one, (4aR,5aR)-5a-methyl-3-(phenylamino)-2-(pyridin-4-yl)-4a,5,5a,6-tetrahydrocyclopropa[f]indol-4(1H)-one, (4aS,5aS)-5a-methyl-3-(phenylamino)-2-(pyridin-4-yl)-4a,5,5a,6-tetrahydrocyclopropa[f]indol-4(1H)-one, N-4-[(4aR,5aR)-5a-methyl-4-oxo-3-(phenylamino)-1,4,4a,5,5a,6-hexahydrocyclopropa[f]indol-2-yl]pyridin-2-ylacetamide, N-4-[(4aS,5aS)-5a-methyl-4-oxo-3-(phenylamino)-1,4,4a,5,5a,6-hexahydrocyclopropa[f]indol-2-yl]pyridin-2-ylacetamide, 3-(phenylamino)-2-(pyridin-4-yl)cyclohepta[b]pyrrol-4(1H)-one, 3-(phenylamino)-2-(pyridin-4-yl)-5,6,7,8-tetrahydrocyclohepta[b]pyrrol-4(1H)-one, 2-(2-aminopyridin-4-yl)-7-methyl-3-(phenylamino)cyclohepta[b]pyrrol-4(1H)-one, (7RS)-2-(2-aminopyridin-4-yl)-7-methyl-3-(phenylamino)-5,6,7,8-tetrahydrocyclohepta[b]pyrrol-4(1H)-one, N-{4-[(7RS)-3-anilino-7-methyl-4-oxo-1,4,5,6,7,8-hexahydrocyclohepta[b]pyrrol-2-yl]pyridin-2-yl}acetamide, rel-(4aR,5aR)-2-(2-aminopyridin-4-yl)-3-anilino-5a-methyl-4a,5,5a,6-tetrahydrocyclopropa[f]indol-4(1H)-one, N-{4-[rel-(4aR,5aR)-3-anilino-5a-methyl-4-oxo-1,4,4a,5,5a,6-hexahydrocyclopropa[f]indol-2-yl]pyridin-2-yl}methanesulfonamide, N-[4-(3-anilino-7-methyl-4-oxo-1,4-dihydrocyclohepta[b]pyrrol-2-yl)pyridin-2-yl]methanesulfonamide, 1-fluoro-N-4-[rel-(4aS,5aR)-5a-methyl-4,6-dioxo-3-(phenylamino)-1,4,4a,5,5a,6-hexahydrocyclopropa[f]indol-2-yl]pyridin-2-ylcyclopropanecarboxamide, 1-fluoro-N-4-[(4aS,5aS)-5a-methyl-4-oxo-3-(phenylamino)-1,4,4a,5,5a,6-hexahydrocyclopropa[f]indol-2-yl]pyridin-2-ylcyclopropanecarboxamide, 1-fluoro-N-4-[(4aR,5aR)-5a-methyl-4-oxo-3-(phenylamino)-1,4,4a,5,5a,6-hexahydrocyclopropa[f]indol-2-yl]pyridin-2-ylcyclopropanecarboxamide, N-4-[rel-(4aS,5aR)-5a-methyl-4,6-dioxo-3-(phenylamino)-1,4,4a,5,5a,6-hexahydrocyclopropa[f]indol-2-yl]pyridin-2-ylcyclopropanecarboxamide, N-{4-[rel-(4aR,5aS)-3-Anilino-5a-methyl-4,6-dioxo-1,4,4a,5,5a,6-hexahydrocyclopropa[f]indol-2-yl]pyridin-2-yl}-1-methylcyclopropanecarboxamide, 1-methyl-N-4-[rel-(4aS,5aR)-5a-methyl-4,6-dioxo-3-(phenylamino)-1,4,4a,5,5a,6-hexahydrocyclopropa[f]indol-2-yl]pyridin-2-yl-1H-pyrazole-3-carboxamide, 4-fluoro-3-methoxy-N-4-[rel-(4aS,5aR)-5a-methyl-4,6-dioxo-3-(phenylamino)-1,4,4a,5,5a,6-hexahydrocyclopropa[f]indol-2-yl]pyridin-2-ylbenzamide, (1S,2S)-2-fluoro-N-4-[(4aS,5aS)-5a-methyl-4-oxo-3-(phenylamino)-1,4,4a,5,5a,6-hexahydrocyclopropa[f]indol-2-yl]pyridin-2-ylcyclopropanecarboxamide, (1S,2S)-2-fluoro-N-4-[(4aR,5aR)-5a-methyl-4-oxo-3-(phenylamino)-1,4,4a,5,5a,6-hexahydrocyclopropa[f]indol-2-yl]pyridin-2-ylcyclopropanecarboxamide, N-4-[(7S)-7-methyl-4-oxo-3-(phenylamino)-1,4,5,6,7,8-hexahydrocyclohepta[b]pyrrol-2-yl]pyridin-2-ylacetamide, N-4-[(7R)-7-methyl-4-oxo-3-(phenylamino)-1,4,5,6,7,8-hexahydrocyclohepta[b]pyrrol-2-yl]pyridin-2-ylacetamide, 2-fluoro-2-methyl-N-4-[(4aS,5aS)-5a-methyl-4-oxo-3-(phenylamino)-1,4,4a,5,5a,6-hexahydrocyclopropa[f]indol-2-yl]pyridin-2-ylpropanamide, 2-fluoro-2-methyl-N-4-[(4aR,5aR)-5a-methyl-4-oxo-3-(phenylamino)-1,4,4a,5,5a,6-hexahydrocyclopropa[f]indol-2-yl]pyridin-2-ylpropanamide, 1-methyl-N-4-[(4aS,5aS)-5a-methyl-4-oxo-3-(phenylamino)-1,4,4a,5,5a,6-hexahydrocyclopropa[f]indol-2-yl]pyridin-2-yl-1H-pyrazole-5-carboxamide, 1-methyl-N-4-[(4aR,5aR)-5a-methyl-4-oxo-3-(phenylamino)-1,4,4a,5,5a,6-hexahydrocyclopropa[f]indol-2-yl]pyridin-2-yl-1H-pyrazole-5-carboxamide, N-4-[(4aS,5aS)-5a-methyl-4-oxo-3-(phenylamino)-1,4,4a,5,5a,6-hexahydrocyclopropa[f]indol-2-yl]pyridin-2-yl-1H-pyrazole-3-carboxamide, N-4-[(4aR,5aR)-5a-methyl-4-oxo-3-(phenylamino)-1,4,4a,5,5a,6-hexahydrocyclopropa[f]indol-2-yl]pyridin-2-yl-1H-pyrazole-3-carboxamide, N-{4-[(4aR,5aR)-3-anilino-5a-methyl-4-oxo-1,4,4a,5,5a,6-hexahydrocyclopropa[f]indol-2-yl]pyridin-2-yl}-2,6-difluorobenzamide, N-{4-[(4aS,5aS)-3-anilino-5a-methyl-4-oxo-1,4,4a,5,5a,6-hexahydrocyclopropa[f]indol-2-yl]pyridin-2-yl}-2,6-difluorobenzamide, N-{4-[(4aR,5aR)-3-anilino-5a-methyl-4-oxo-1,4,4a,5,5a,6-hexahydrocyclopropa[f]indol-2-yl]pyridin-2-yl}-4-fluoro-2-methylbenzamide, N-{4-[(4aS,5aS)-3-anilino-5a-methyl-4-oxo-1,4,4a,5,5a,6-hexahydrocyclopropa[f]indol-2-yl]pyridin-2-yl}-4-fluoro-2-methylbenzamide, N-{4-[(4aR,5aR)-3-anilino-5a-methyl-4-oxo-1,4,4a,5,5a,6-hexahydrocyclopropa[f]indol-2-yl]pyridin-2-yl}-3-fluoro-4-methoxybenzamide, and N-{4-[(4aS,5aS)-3-anilino-5a-methyl-4-oxo-1,4,4a,5,5a,6-hexahydrocyclopropa[f]indol-2-yl]pyridin-2-yl}-3-fluoro-4-methoxybenzamide, or an N-oxide, a salt, a tautomer or a stereoisomer of said compound, or a salt of said N-oxide, tautomer or stereoisomer.

6. A method for the treatment of a haematological tumor, solid tumor, and/or matastases thereof, comprising administering to a patient in need thereof a therapeutically effective amount of a compound according to claim 1, wherein the tumor is a cervical tumor, a breast tumor, a non-small cell lung tumor, a prostate tumor, a colon tumor, or a melanoma tumor and/or metastases thereof.

7. A pharmaceutical composition comprising at least one compound according to claim 1, together with at least one pharmaceutically acceptable auxiliary.

8. A method for the treatment of a haematological tumor, solid tumor, and/or matastases thereof, comprising administering to a patient in need thereof a therapeutically effective amount of a pharmaceutical composition according to claim 7, wherein the tumor is a cervical tumor, a breast tumor, a non-small cell lung tumor, a prostate tumor, a colon tumor, or a melanoma tumor and/or metastases thereof.

* * * * *